United States Patent
Dunn et al.

(10) Patent No.: US 9,962,295 B2
(45) Date of Patent: May 8, 2018

(54) NEGATIVE PRESSURE WOUND CLOSURE DEVICE

(71) Applicants: Smith & Nephew, Inc., Memphis, TN (US); University of Massachusetts, Boston, MA (US)

(72) Inventors: Raymond M Dunn, Shrewsbury, MA (US); Victoria Jody Hammond, Hull (GB); Edward Yerbury Hartwell, Hull (GB); John Kenneth Hicks, York (GB); Elizabeth Mary Huddleston, York (GB); Andrew Kelly, Hitchin (GB); Andrew Linton, York (GB); Mark Richardson, Grimsby (GB); Carl Saxby, Brough (GB); Tim Stern, Belper (GB)

(73) Assignees: Smith & Nephew, Inc., Memphis, TN (US); University of Massachusetts, Boston, MA (US)

( * ) Notice: Subject to any disclaimer, the term of this patent is extended or adjusted under 35 U.S.C. 154(b) by 630 days.

(21) Appl. No.: 14/415,539

(22) PCT Filed: Jul. 16, 2013

(86) PCT No.: PCT/US2013/050619
§ 371 (c)(1),
(2) Date: Jan. 16, 2015

(87) PCT Pub. No.: WO2014/014871
PCT Pub. Date: Jan. 23, 2014

(65) Prior Publication Data
US 2015/0196431 A1    Jul. 16, 2015

Related U.S. Application Data

(60) Provisional application No. 61/672,225, filed on Jul. 16, 2012, provisional application No. 61/771,732, (Continued)

(51) Int. Cl.
*A61M 35/00* (2006.01)
*A61M 1/00* (2006.01)
(Continued)

(52) U.S. Cl.
CPC ..... *A61F 13/00068* (2013.01); *A61M 1/0088* (2013.01); *A61F 2013/00178* (2013.01); *A61F 2013/00536* (2013.01)

(58) Field of Classification Search
CPC ........ A61M 35/00; A61M 1/00; A61M 27/00; A61F 13/00; A61F 13/02
See application file for complete search history.

(56) References Cited

U.S. PATENT DOCUMENTS 3,194,239 A    7/1965  Sullivan
3,789,851 A    2/1974  LeVeen
(Continued)

FOREIGN PATENT DOCUMENTS

CN    1438904        8/2003
CN    101112326 A    1/2008
(Continued)

OTHER PUBLICATIONS

Hougaard, et al., "The open abdomen: temporary closure with a modified negative pressure therapy technique", International Wound Journal, (2014), ISSN 1742-4801, pp. 13-16.
(Continued)

*Primary Examiner* — Michele Kidwell
*Assistant Examiner* — Ilya Treyger
(74) *Attorney, Agent, or Firm* — Knobbe, Martens, Olson & Bear LLP

(57) ABSTRACT

The present invention relates to a negative pressure wound closure system and methods for using such a system. Preferred embodiments of the invention facilitate closure of the wound by preferentially contracting to provide for movement of the tissue. Preferred embodiments can utilize tissue grasping elements to apply a wound closing force to the tissue.

17 Claims, 73 Drawing Sheets

Related U.S. Application Data filed on Mar. 1, 2013, provisional application No. 61/780,629, filed on Mar. 13, 2013.

(51) Int. Cl.
*A61F 13/00* (2006.01)
*A61M 27/00* (2006.01)
*A61F 13/02* (2006.01)

(56) References Cited

U.S. PATENT DOCUMENTS

| | | |
|---|---|---|
| 4,467,805 A | 8/1984 | Fukuda |
| 4,815,468 A | 3/1989 | Annand |
| 5,409,472 A | 4/1995 | Rawlings et al. |
| 5,415,715 A | 5/1995 | Delage et al. |
| 5,423,857 A | 6/1995 | Rosenman et al. |
| 5,512,041 A | 4/1996 | Bogart |
| 5,584,859 A | 12/1996 | Brotz |
| 5,636,643 A | 6/1997 | Argenta et al. |
| 5,695,777 A | 12/1997 | Donovan et al. |
| 5,960,497 A | 10/1999 | Castellino et al. |
| 6,080,168 A | 6/2000 | Levin et al. |
| 6,086,591 A | 7/2000 | Bojarski |
| 6,142,982 A | 11/2000 | Hunt et al. |
| 6,176,868 B1 | 1/2001 | Detour |
| 6,548,727 B1 | 4/2003 | Swenson |
| 6,553,998 B2 | 4/2003 | Heaton et al. |
| 6,566,575 B1 | 5/2003 | Stickels et al. |
| 6,685,681 B2 | 2/2004 | Lockwood et al. |
| 6,695,823 B1 | 2/2004 | Lina et al. |
| 6,712,830 B2 | 3/2004 | Esplin |
| 6,767,334 B1 | 7/2004 | Randolph |
| 6,770,794 B2 | 8/2004 | Fleischmann |
| 6,776,769 B2 | 8/2004 | Smith |
| 6,787,682 B2 | 9/2004 | Gilman |
| 6,814,079 B2 | 11/2004 | Heaton et al. |
| 6,893,452 B2 | 5/2005 | Jacobs |
| 6,936,037 B2 | 8/2005 | Bubb |
| 6,951,553 B2 | 10/2005 | Bubb et al. |
| 6,977,323 B1 | 12/2005 | Swenson |
| 6,994,702 B1 | 2/2006 | Johnson |
| 7,004,915 B2 | 2/2006 | Boynton et al. |
| 7,025,755 B2 | 4/2006 | Epstein |
| 7,070,584 B2 | 7/2006 | Johnson et al. |
| 7,117,869 B2 | 10/2006 | Heaton et al. |
| 7,128,735 B2 | 10/2006 | Weston |
| 7,144,390 B1 | 12/2006 | Hannigan et al. |
| 7,153,312 B1 | 12/2006 | Torrie et al. |
| 7,156,862 B2 | 1/2007 | Jacobs et al. |
| 7,172,615 B2 | 2/2007 | Morriss et al. |
| 7,189,238 B2 | 3/2007 | Lombardo et al. |
| 7,196,054 B1 | 3/2007 | Drohan et al. |
| 7,198,046 B1 | 4/2007 | Argenta et al. |
| 7,216,651 B2 | 5/2007 | Argenta et al. |
| D544,092 S | 6/2007 | Lewis |
| 7,262,174 B2 | 8/2007 | Jiang et al. |
| 7,279,612 B1 | 10/2007 | Heaton et al. |
| 7,315,183 B2 | 1/2008 | Hinterscher |
| 7,351,250 B2 | 4/2008 | Zamierowski |
| 7,361,184 B2 | 4/2008 | Joshi |
| 7,367,342 B2 | 5/2008 | Butler |
| 7,381,211 B2 | 6/2008 | Zamierowski |
| 7,381,859 B2 | 6/2008 | Hunt et al. |
| 7,413,571 B2 | 8/2008 | Zamierowski |
| 7,438,705 B2 | 10/2008 | Karpowicz et al. |
| 7,494,482 B2 | 2/2009 | Orgill et al. |
| 7,534,240 B1 | 5/2009 | Johnson |
| 7,540,848 B2 | 6/2009 | Hannigan et al. |
| 7,553,306 B1 | 6/2009 | Hunt et al. |
| 7,553,923 B2 | 6/2009 | Williams et al. |
| 7,569,742 B2 | 8/2009 | Haggstrom et al. |
| 7,578,532 B2 | 8/2009 | Schiebler |
| D602,583 S | 10/2009 | Pidgeon et al. |
| 7,611,500 B1 | 11/2009 | Lina et al. |
| 7,615,036 B2 | 11/2009 | Joshi et al. |
| 7,618,382 B2 | 11/2009 | Vogel et al. |
| 7,625,362 B2 | 12/2009 | Boehringer et al. |
| 7,645,269 B2 | 1/2010 | Zamierowski |
| 7,651,484 B2 | 1/2010 | Heaton et al. |
| 7,670,323 B2 | 3/2010 | Hunt et al. |
| 7,678,102 B1 | 3/2010 | Heaton |
| 7,683,667 B2 | 3/2010 | Kim |
| 7,699,823 B2 | 4/2010 | Haggstrom et al. |
| 7,699,830 B2 | 4/2010 | Martin |
| 7,699,831 B2 | 4/2010 | Bengtson et al. |
| 7,700,819 B2 | 4/2010 | Ambrosio et al. |
| 7,708,724 B2 | 5/2010 | Weston |
| 7,713,743 B2 | 5/2010 | Villanueva et al. |
| 7,722,528 B2 | 5/2010 | Arnal et al. |
| 7,723,560 B2 | 5/2010 | Lockwood et al. |
| 7,754,937 B2 | 7/2010 | Boehringer et al. |
| 7,776,028 B2 | 8/2010 | Miller et al. |
| 7,777,522 B2 | 8/2010 | Yang |
| 7,779,625 B2 | 8/2010 | Joshi et al. |
| D625,801 S | 10/2010 | Pidgeon et al. |
| 7,815,616 B2 | 10/2010 | Boehringer et al. |
| 7,820,453 B2 | 10/2010 | Heylen et al. |
| 7,846,141 B2 | 12/2010 | Weston |
| 7,857,806 B2 | 12/2010 | Karpowicz et al. |
| 7,896,856 B2 | 3/2011 | Petrosenko et al. |
| 7,909,805 B2 | 3/2011 | Weston |
| 7,931,774 B2 | 4/2011 | Hall et al. |
| 7,942,866 B2 | 5/2011 | Radl et al. |
| 7,951,124 B2 | 5/2011 | Boehringer et al. |
| 7,964,766 B2 | 6/2011 | Blott et al. |
| 7,976,519 B2 | 7/2011 | Bubb et al. |
| 7,976,524 B2 | 7/2011 | Kudo et al. |
| 7,981,098 B2 | 7/2011 | Boehringer et al. |
| 8,030,534 B2 | 10/2011 | Radl et al. |
| 8,062,272 B2 | 11/2011 | Weston |
| 8,062,295 B2 | 11/2011 | McDevitt et al. |
| 8,062,331 B2 | 11/2011 | Zamierowski |
| 8,070,773 B2 | 12/2011 | Zamierowski |
| 8,080,702 B2 | 12/2011 | Blott et al. |
| 8,100,887 B2 | 1/2012 | Weston et al. |
| 8,114,126 B2 | 2/2012 | Heaton et al. |
| 8,123,781 B2 | 2/2012 | Zamierowski |
| 8,128,615 B2 | 3/2012 | Blott et al. |
| 8,129,580 B2 | 3/2012 | Wilkes et al. |
| 8,142,419 B2 | 3/2012 | Heaton et al. |
| 8,162,909 B2 | 4/2012 | Blott et al. |
| 8,172,816 B2 | 5/2012 | Kazala, Jr. et al. |
| 8,182,413 B2 | 5/2012 | Browning |
| 8,187,237 B2 | 5/2012 | Seegert |
| 8,188,331 B2 | 5/2012 | Barta et al. |
| 8,192,409 B2 | 6/2012 | Hardman et al. |
| 8,197,467 B2 | 6/2012 | Heaton et al. |
| 8,207,392 B2 | 6/2012 | Haggstrom et al. |
| 8,235,955 B2 | 8/2012 | Blott et al. |
| 8,246,590 B2 | 8/2012 | Hu et al. |
| 8,257,328 B2 | 9/2012 | Augustine et al. |
| 8,273,105 B2 | 9/2012 | Cohen et al. |
| 8,353,931 B2 | 1/2013 | Stopek et al. |
| 8,376,972 B2 | 2/2013 | Fleischmann |
| 8,399,730 B2 | 3/2013 | Kazala et al. |
| 8,444,392 B2 | 5/2013 | Turner et al. |
| 8,447,375 B2 | 5/2013 | Shuler |

(56) References Cited

U.S. PATENT DOCUMENTS

| | | |
|---|---|---|
| 8,454,990 B2 | 6/2013 | Canada et al. |
| 8,460,255 B2 | 6/2013 | Joshi et al. |
| 8,460,257 B2 | 6/2013 | Locke et al. |
| 8,481,804 B2 | 7/2013 | Timothy |
| 8,486,032 B2 | 7/2013 | Seegert et al. |
| 8,500,704 B2 | 8/2013 | Boehringer et al. |
| 8,500,776 B2 | 8/2013 | Ebner |
| 8,523,832 B2 | 9/2013 | Seegert |
| 8,535,296 B2 | 9/2013 | Blott et al. |
| 8,562,576 B2 | 10/2013 | Hu et al. |
| 8,608,776 B2 | 12/2013 | Coward et al. |
| 8,622,981 B2 | 1/2014 | Hartwell et al. |
| 8,628,505 B2 | 1/2014 | Weston |
| 8,632,523 B2 | 1/2014 | Eriksson et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,708,984 B2 | 4/2014 | Robinson et al. |
| 8,715,256 B2 | 5/2014 | Greener |
| 8,721,629 B2 | 5/2014 | Hardman et al. |
| 8,746,662 B2 | 6/2014 | Poppe |
| 8,747,375 B2 | 6/2014 | Barta et al. |
| 8,764,732 B2 | 7/2014 | Hartwell |
| 8,791,315 B2 | 7/2014 | Lattimore et al. |
| 8,791,316 B2 | 7/2014 | Greener |
| 8,802,916 B2 | 8/2014 | Griffey et al. |
| 8,814,842 B2 | 8/2014 | Coulthard et al. |
| 8,821,535 B2 | 9/2014 | Greener |
| 8,843,327 B2 | 9/2014 | Vernon-Harcourt et al. |
| 8,882,730 B2 | 11/2014 | Zimnitsky et al. |
| 8,936,618 B2 | 1/2015 | Sealy et al. |
| 8,945,030 B2 | 2/2015 | Weston |
| 8,951,235 B2 | 2/2015 | Allen et al. |
| 9,061,095 B2 | 6/2015 | Adie et al. |
| 9,084,845 B2 | 7/2015 | Adie et al. |
| 9,180,231 B2 | 11/2015 | Greener |
| 9,220,822 B2 | 12/2015 | Hartwell et al. |
| 9,301,742 B2 | 4/2016 | Dunn |
| 9,408,755 B2 | 8/2016 | Larsson et al. |
| 9,421,132 B2 | 8/2016 | Dunn |
| 2001/0029956 A1 | 10/2001 | Argenta |
| 2001/0034499 A1 | 10/2001 | Sessions et al. |
| 2002/0022861 A1 | 2/2002 | Jacobs et al. |
| 2002/0077661 A1 | 6/2002 | Saadat |
| 2002/0161346 A1 | 10/2002 | Lockwood et al. |
| 2003/0065360 A1 | 4/2003 | Jacobs et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0220660 A1 | 11/2003 | Kortanbach et al. |
| 2004/0006319 A1 | 1/2004 | Lina et al. |
| 2004/0010275 A1 | 1/2004 | Jacobs et al. |
| 2004/0054346 A1 | 3/2004 | Zhu et al. |
| 2004/0064132 A1 | 4/2004 | Boehringer et al. |
| 2004/0147465 A1 | 7/2004 | Jiang et al. |
| 2004/0162512 A1 | 8/2004 | Liedtke et al. |
| 2004/0267312 A1 | 12/2004 | Kanner et al. |
| 2005/0119694 A1 | 6/2005 | Jacobs et al. |
| 2005/0182445 A1 | 8/2005 | Zamierowski |
| 2005/0222613 A1 | 10/2005 | Ryan |
| 2005/0258887 A1 | 11/2005 | Ito |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0064124 A1 | 3/2006 | Zhu et al. |
| 2006/0069357 A1 | 3/2006 | Marasco |
| 2006/0079599 A1 | 4/2006 | Arthur |
| 2006/0135921 A1 | 6/2006 | Wiercinski et al. |
| 2006/0213527 A1 | 9/2006 | Argenta et al. |
| 2006/0257457 A1 | 11/2006 | Gorman et al. |
| 2006/0259074 A1 | 11/2006 | Kelleher et al. |
| 2007/0032755 A1 | 2/2007 | Walsh |
| 2007/0032763 A1 | 2/2007 | Vogel |
| 2007/0038172 A1 | 2/2007 | Zamierowski |
| 2007/0052144 A1 | 3/2007 | Knirck et al. |
| 2007/0118096 A1 | 5/2007 | Smith et al. |
| 2007/0123816 A1 | 5/2007 | Zhu et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0185463 A1 | 8/2007 | Mulligan |
| 2007/0213597 A1 | 9/2007 | Wooster |
| 2007/0219513 A1 | 9/2007 | Lina et al. |
| 2007/0282309 A1 | 12/2007 | Bengtson et al. |
| 2007/0282374 A1 | 12/2007 | Sogard et al. |
| 2007/0299541 A1 | 12/2007 | Chernomorsky et al. |
| 2008/0041401 A1 | 2/2008 | Casola et al. |
| 2008/0108977 A1 | 5/2008 | Heaton et al. |
| 2008/0275409 A1 | 11/2008 | Kane et al. |
| 2008/0287973 A1 | 11/2008 | Aster et al. |
| 2009/0005716 A1 | 1/2009 | Abuzaina et al. |
| 2009/0005744 A1 | 1/2009 | Karpowicz et al. |
| 2009/0018578 A1 | 1/2009 | Wilke et al. |
| 2009/0018579 A1 | 1/2009 | Wilke et al. |
| 2009/0043268 A1 | 2/2009 | Eddy et al. |
| 2009/0069760 A1 | 3/2009 | Finklestein |
| 2009/0069904 A1 | 3/2009 | Picha |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0131888 A1 | 5/2009 | Joshi |
| 2009/0137973 A1 | 5/2009 | Karpowicz et al. |
| 2009/0227938 A1 | 9/2009 | Fasching et al. |
| 2009/0246238 A1 | 10/2009 | Gorman et al. |
| 2009/0299303 A1 | 12/2009 | Seegert |
| 2010/0022972 A1 | 1/2010 | Lina et al. |
| 2010/0022990 A1 | 1/2010 | Karpowicz et al. |
| 2010/0028407 A1 | 2/2010 | Del Priore et al. |
| 2010/0030132 A1 | 2/2010 | Niezgoda et al. |
| 2010/0036333 A1 | 2/2010 | Schenk, III et al. |
| 2010/0081983 A1 | 4/2010 | Zocher et al. |
| 2010/0106184 A1 | 4/2010 | Coward et al. |
| 2010/0121286 A1 | 5/2010 | Locke et al. |
| 2010/0121287 A1 | 5/2010 | Smith et al. |
| 2010/0137775 A1 | 6/2010 | Hu et al. |
| 2010/0137890 A1 | 6/2010 | Martinez et al. |
| 2010/0150991 A1 | 6/2010 | Bernstein |
| 2010/0160874 A1 | 6/2010 | Robinson et al. |
| 2010/0160901 A1 | 6/2010 | Hu et al. |
| 2010/0179515 A1 | 7/2010 | Swain et al. |
| 2010/0198128 A1 | 8/2010 | Turnlund et al. |
| 2010/0211030 A1 | 8/2010 | Turner et al. |
| 2010/0256672 A1 | 10/2010 | Weinberg et al. |
| 2010/0262126 A1 | 10/2010 | Hu et al. |
| 2010/0280468 A1 | 11/2010 | Haggstrom et al. |
| 2010/0292717 A1 | 11/2010 | Petier-Puchner et al. |
| 2010/0305490 A1 | 12/2010 | Coulthard et al. |
| 2011/0004173 A1 | 1/2011 | Hu et al. |
| 2011/0015594 A1 | 1/2011 | Hu et al. |
| 2011/0021965 A1 | 1/2011 | Karp et al. |
| 2011/0022082 A1 | 1/2011 | Burke et al. |
| 2011/0054283 A1 | 3/2011 | Shuler |
| 2011/0066096 A1 | 3/2011 | Svedman |
| 2011/0077605 A1 | 3/2011 | Karpowicz et al. |
| 2011/0082480 A1 | 4/2011 | Viola |
| 2011/0105963 A1 | 5/2011 | Hu et al. |
| 2011/0106026 A1 | 5/2011 | Wu et al. |
| 2011/0110996 A1 | 5/2011 | Schoenberger et al. |
| 2011/0112458 A1 | 5/2011 | Holm et al. |
| 2011/0130774 A1 | 6/2011 | Criscuolo et al. |
| 2011/0172760 A1 | 7/2011 | Anderson |
| 2011/0178451 A1 | 7/2011 | Robinson et al. |
| 2011/0224631 A1 | 9/2011 | Simmons |
| 2011/0224632 A1 | 9/2011 | Zimitsky et al. |
| 2011/0224634 A1 | 9/2011 | Locke et al. |
| 2011/0236460 A1 | 9/2011 | Stopek et al. |
| 2011/0238026 A1 | 9/2011 | Zhang et al. |
| 2011/0238095 A1 | 9/2011 | Browning |
| 2011/0238110 A1 | 9/2011 | Wilke et al. |
| 2011/0245682 A1 | 10/2011 | Robinson et al. |
| 2011/0245788 A1 | 10/2011 | Marquez Canada |

(56) References Cited

U.S. PATENT DOCUMENTS

| | | |
|---|---|---|
| 2011/0264138 A1 | 10/2011 | Avelar et al. |
| 2011/0282136 A1 | 11/2011 | Browning |
| 2011/0282310 A1 | 11/2011 | Boehringer et al. |
| 2011/0313374 A1 | 12/2011 | Lockwood et al. |
| 2012/0004631 A9 | 1/2012 | Hartwell |
| 2012/0010637 A1 | 1/2012 | Stopek et al. |
| 2012/0016321 A1 | 1/2012 | Wu et al. |
| 2012/0016322 A1 | 1/2012 | Goulthard |
| 2012/0029449 A1 | 2/2012 | Khosrowshahi |
| 2012/0029455 A1 | 2/2012 | Perez-Foullerat et al. |
| 2012/0035560 A1 | 2/2012 | Eddy et al. |
| 2012/0041402 A1 | 2/2012 | Greener |
| 2012/0059399 A1 | 3/2012 | Hoke et al. |
| 2012/0059412 A1 | 3/2012 | Fleischmann |
| 2012/0065664 A1 | 3/2012 | Avitable et al. |
| 2012/0071841 A1 | 3/2012 | Bengtson |
| 2012/0083755 A1 | 4/2012 | Lina et al. |
| 2012/0095426 A1 | 4/2012 | Visscher et al. |
| 2012/0109188 A1 | 5/2012 | Viola |
| 2012/0121556 A1 | 5/2012 | Fraser et al. |
| 2012/0123358 A1 | 5/2012 | Hall et al. |
| 2012/0130327 A1 | 5/2012 | Marquez Canada |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0143158 A1 | 6/2012 | Yang et al. |
| 2012/0144989 A1 | 6/2012 | De Plessis et al. |
| 2012/0150133 A1 | 6/2012 | Heaton et al. |
| 2012/0172778 A1 | 7/2012 | Rastegar et al. |
| 2012/0172926 A1 | 7/2012 | Hotter |
| 2012/0191054 A1 | 7/2012 | Kazala, Jr. et al. |
| 2012/0191132 A1 | 7/2012 | Sargeant |
| 2012/0197415 A1 | 8/2012 | Montanari et al. |
| 2012/0203189 A1 | 8/2012 | Barta et al. |
| 2012/0209226 A1 | 8/2012 | Simmons et al. |
| 2012/0209227 A1 | 8/2012 | Dunn |
| 2012/0220968 A1 | 8/2012 | Confalone et al. |
| 2012/0222687 A1 | 9/2012 | Czajka, Jr. et al. |
| 2012/0277773 A1 | 11/2012 | Sargeant et al. |
| 2012/0302440 A1 | 11/2012 | Theliander et al. |
| 2013/0096518 A1 | 4/2013 | Hall et al. |
| 2013/0131564 A1 | 5/2013 | Locke et al. |
| 2013/0138054 A1 | 5/2013 | Fleischmann |
| 2013/0150814 A1 | 6/2013 | Buan |
| 2013/0197457 A1 | 8/2013 | Kazala et al. |
| 2013/0253401 A1 | 9/2013 | Locke et al. |
| 2013/0331757 A1 | 12/2013 | Belson |
| 2014/0068914 A1 | 3/2014 | Coward et al. |
| 2014/0088455 A1 | 3/2014 | Christensen et al. |
| 2014/0094730 A1 | 4/2014 | Greener |
| 2014/0163415 A1 | 6/2014 | Zaiken et al. |
| 2014/0194836 A1 | 7/2014 | Kazala et al. |
| 2014/0194837 A1 | 7/2014 | Robinson et al. |
| 2014/0213994 A1 | 7/2014 | Hardman et al. |
| 2014/0228789 A1 | 8/2014 | Wilkes et al. |
| 2015/0005722 A1 | 1/2015 | Hu et al. |
| 2015/0025484 A1 | 1/2015 | Simmons et al. |
| 2015/0065968 A1 | 3/2015 | Sealy et al. |
| 2015/0080947 A1 | 3/2015 | Greener |
| 2015/0112311 A1 | 4/2015 | Hammond et al. |
| 2015/0119837 A1 | 4/2015 | Thompson, Jr. et al. |
| 2015/0148760 A1 | 5/2015 | Dodd et al. |
| 2015/0150729 A1 | 6/2015 | Dagger et al. |
| 2015/0157758 A1 | 6/2015 | Blucher et al. |
| 2015/0159066 A1 | 6/2015 | Hartwell et al. |
| 2015/0190288 A1 | 7/2015 | Dunn |
| 2015/0320602 A1 | 11/2015 | Locke et al. |

FOREIGN PATENT DOCUMENTS

| | | |
|---|---|---|
| CN | 101123930 | 2/2008 |
| CN | 101208115 | 6/2008 |
| CN | 101257938 | 9/2008 |
| CN | 101588836 | 11/2009 |
| CN | 102046117 | 5/2011 |
| CN | 102196830 | 9/2011 |
| CN | 102256637 | 11/2011 |
| CN | 102781380 | 11/2012 |
| CN | 104768474 A | 7/2015 |
| CN | 104812343 A | 7/2015 |
| DE | 2 949 920 | 3/1981 |
| DE | 10 2005 007016 | 8/2006 |
| EP | 1 320 342 A1 | 6/2003 |
| EP | 2 279 016 A1 | 2/2011 |
| EP | 2 366 721 A1 | 9/2011 |
| EP | 2 368 523 A1 | 9/2011 |
| EP | 2 404 626 A2 | 1/2012 |
| EP | 2 341 955 B1 | 12/2012 |
| EP | 2 567 682 A1 | 3/2013 |
| EP | 2 567 717 A1 | 3/2013 |
| EP | 2 594 299 A2 | 5/2013 |
| EP | 2 601 984 A2 | 6/2013 |
| EP | 2 623 137 A2 | 8/2013 |
| EP | 2 367 517 A4 | 9/2013 |
| EP | 2 759 265 A2 | 7/2014 |
| EP | 2 829 287 A1 | 1/2015 |
| EP | 2 872 085 A1 | 5/2015 |
| GB | 2389794 A | 12/2003 |
| GB | 2423019 A | 8/2006 |
| GB | 2489947 | 10/2012 |
| GB | 2496310 A | 5/2013 |
| JP | H09-503923 | 4/1997 |
| JP | 2007-505678 | 3/2007 |
| JP | 2007-531567 | 11/2007 |
| JP | 2008-529618 | 8/2008 |
| JP | 2009-536851 | 10/2009 |
| JP | 2010-526597 | 8/2010 |
| JP | 2011-500170 | 1/2011 |
| JP | 2011-523575 | 8/2011 |
| JP | 2013-526938 | 6/2013 |
| MX | A/2015/000715 | 9/2015 |
| WO | WO 2001/89392 | 11/2001 |
| WO | WO 2002/05737 | 1/2002 |
| WO | WO 2003/003948 | 1/2003 |
| WO | WO 2004/018020 | 3/2004 |
| WO | WO 2004/037334 | 5/2004 |
| WO | WO 2005/046761 | 5/2005 |
| WO | WO 2006/041496 | 4/2006 |
| WO | WO 2006/046060 | 5/2006 |
| WO | WO 2007/030601 | 3/2007 |
| WO | WO 2008/104609 | * 3/2007 |
| WO | WO 2007/133618 | 11/2007 |
| WO | WO 2008/064502 | 6/2008 |
| WO | WO 2008/104609 | 9/2008 |
| WO | WO 2010/075180 | * 12/2008 |
| WO | WO 2009/019495 | 2/2009 |
| WO | WO 2009/071926 | 6/2009 |
| WO | WO 2009/071933 | 6/2009 |
| WO | WO 2009/112062 | 9/2009 |
| WO | WO 2009/112848 | 9/2009 |
| WO | WO 2009/114624 | 9/2009 |
| WO | WO 2009/156709 | 12/2009 |
| WO | WO 2009/158132 | 12/2009 |
| WO | WO 2010/033725 | 3/2010 |
| WO | WO 2010/059612 | 5/2010 |
| WO | WO 2010/075180 | 7/2010 |
| WO | WO 2010/078349 | 7/2010 |
| WO | WO 2010/092334 | 8/2010 |
| WO | WO 2010/097570 | 9/2010 |
| WO | WO 2011/023384 | 3/2011 |
| WO | WO 2011/087871 | 7/2011 |
| WO | WO 2011/091169 | 7/2011 |
| WO | WO 2011/106722 | 9/2011 |
| WO | WO 2011/115908 | 9/2011 |
| WO | WO 2011/135286 | 11/2011 |
| WO | WO 2011/135287 | 11/2011 |
| WO | WO 2011/137230 | 11/2011 |
| WO | WO 2012/021553 | 2/2012 |
| WO | WO 2012/038727 | 3/2012 |
| WO | WO 2012/082716 | 6/2012 |
| WO | WO 2012/082876 | 6/2012 |
| WO | WO 2012/087376 | 6/2012 |
| WO | WO 2012/112204 | 8/2012 |
| WO | WO 2012/136707 | 10/2012 |

(56) References Cited

FOREIGN PATENT DOCUMENTS

| WO | WO 2012/142473 | 10/2012 |
| WO | WO 2012/156655 | 11/2012 |
| WO | WO 2012/168678 | 12/2012 |
| WO | WO 2013/007973 | 1/2013 |
| WO | WO 2013/012381 | 1/2013 |
| WO | WO 2013/043258 | 3/2013 |
| WO | WO 2013/071243 | 5/2013 |
| WO | WO 2013/079947 | 6/2013 |
| WO | WO 2013/136181 | 11/2013 |
| WO | WO 2013/175309 | 11/2013 |
| WO | WO 2013/175310 | 11/2013 |
| WO | WO 2014/013348 | 1/2014 |
| WO | WO 2014/014842 | 1/2014 |
| WO | WO 2014/014871 | 1/2014 |
| WO | WO 2014/014922 | 1/2014 |
| WO | WO 2014/024048 | 2/2014 |
| WO | WO 2014/140578 | 9/2014 |
| WO | WO 2014/158526 | 10/2014 |
| WO | WO 2014/165275 | 10/2014 |
| WO | WO 2015/008054 | 1/2015 |
| WO | WO 2015/061352 | 4/2015 |
| WO | WO 2015/109359 | 7/2015 |
| WO | WO 2015/110409 | 7/2015 |
| WO | WO 2015/110410 | 7/2015 |
| WO | WO 2016/176513 | 11/2016 |

OTHER PUBLICATIONS

International Preliminary Report on Patentability and Written Opinion, re PCT Application No. PCT/US2013/050619, dated Jan. 20, 2015.
International Search Report and Written Opinion, re PCT Application No. PCT/US2013/050619, dated Oct. 14, 2013.
International Search Report and Written Opinion, re PCT Application No. PCT/US2013/050698, dated Oct. 14, 2013.
International Preliminary Report on Patentability and Written Opinion, re PCT Application No. PCT/US2013/050698, dated Jan. 20, 2015.
Kapischke, et al., "Self-fixating mesh for the Lichtenstein procedure—a prestudy", Langenbecks Arch Surg (2010), 395 pp. 317-322.
Definition of "Adhere", The Free Dictionary, accessed Mar. 23, 2017, in 6 pages. URL: http://www.thefreedictionary.com/adhere.
Definition of "Throughout", Merriam-Webster Dictionary, accessed Aug. 29, 2017, in 11 pages. URL: https://www.merriam-webster.com/dictionary/throughout.

* cited by examiner

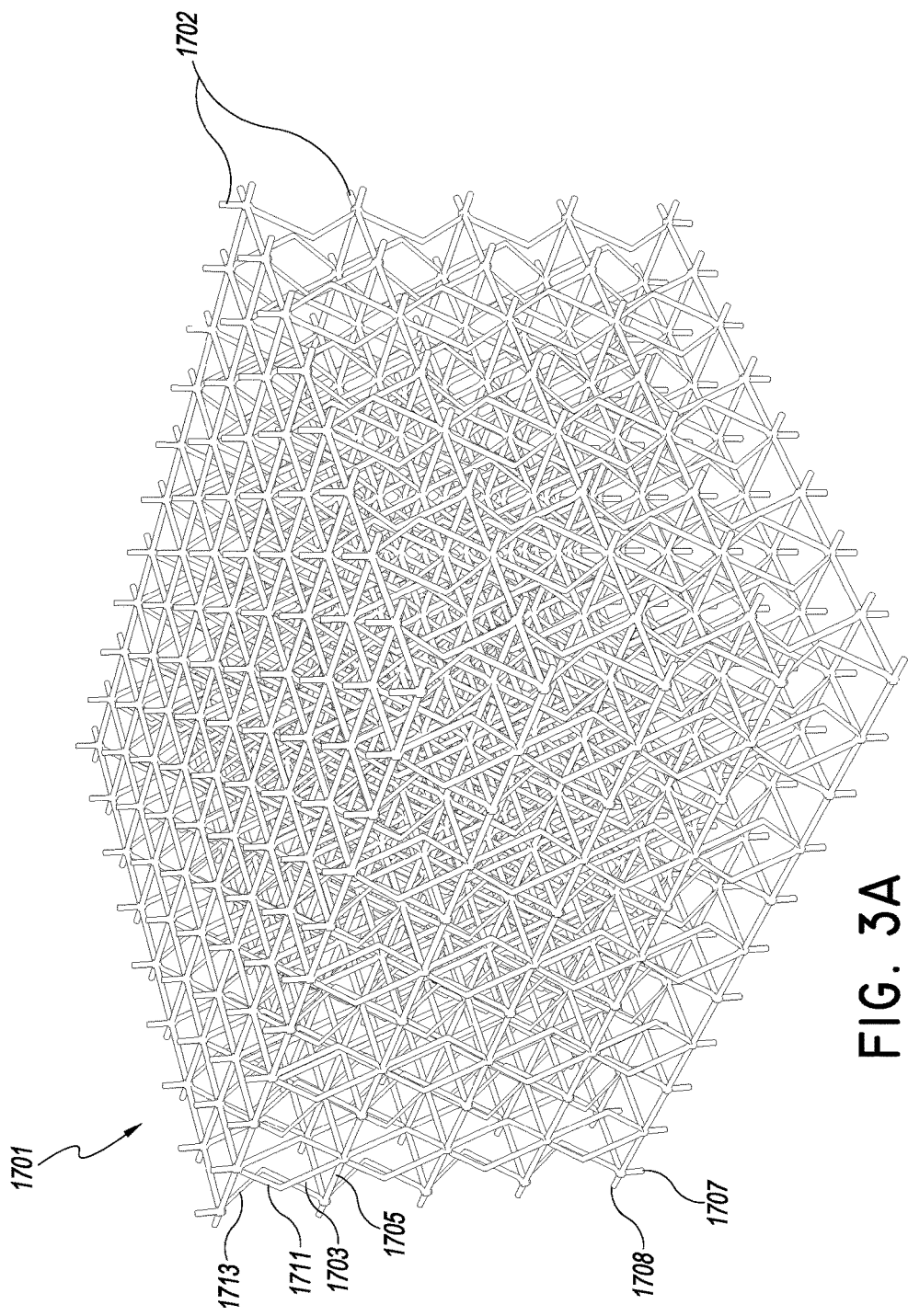

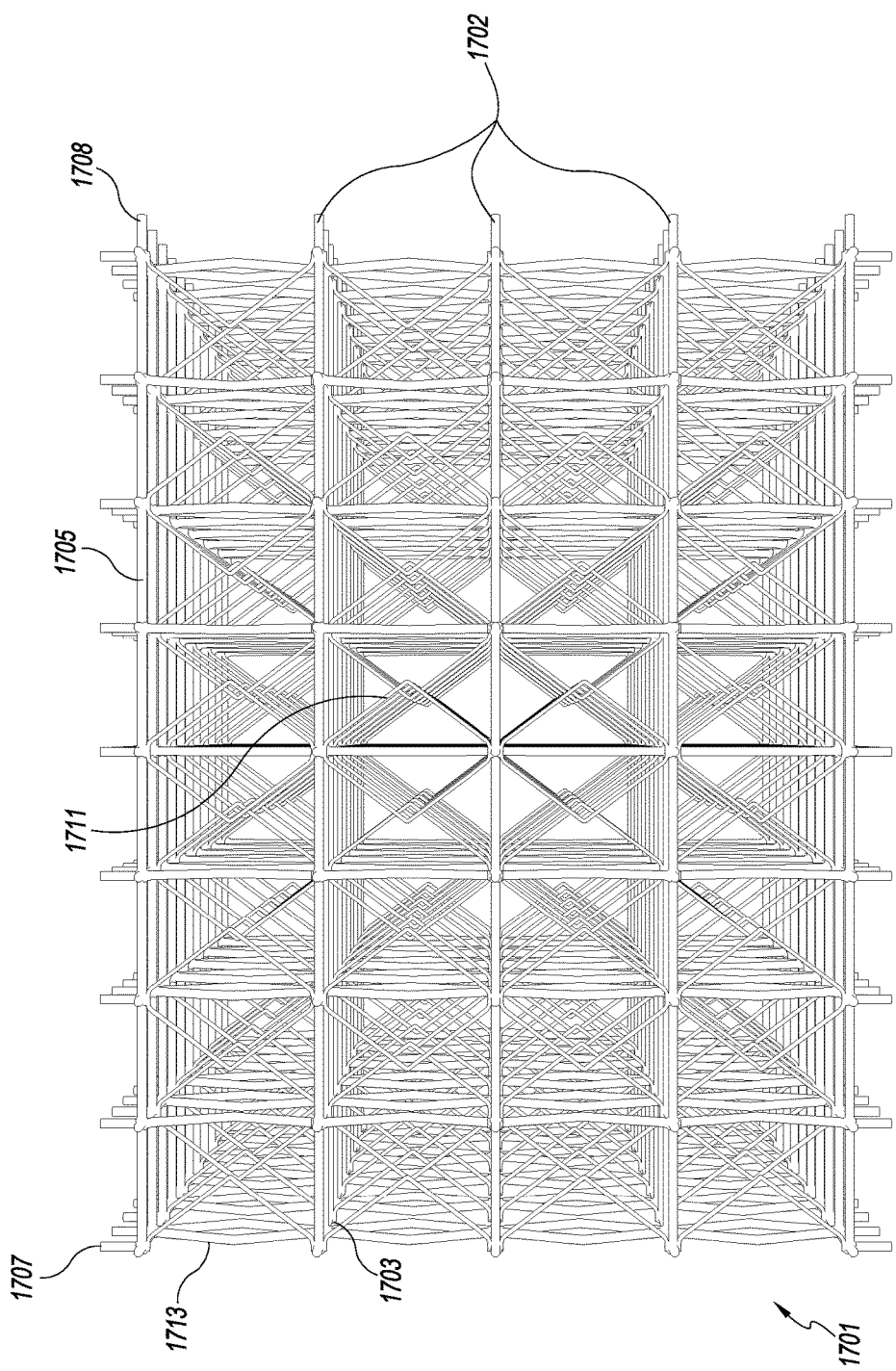

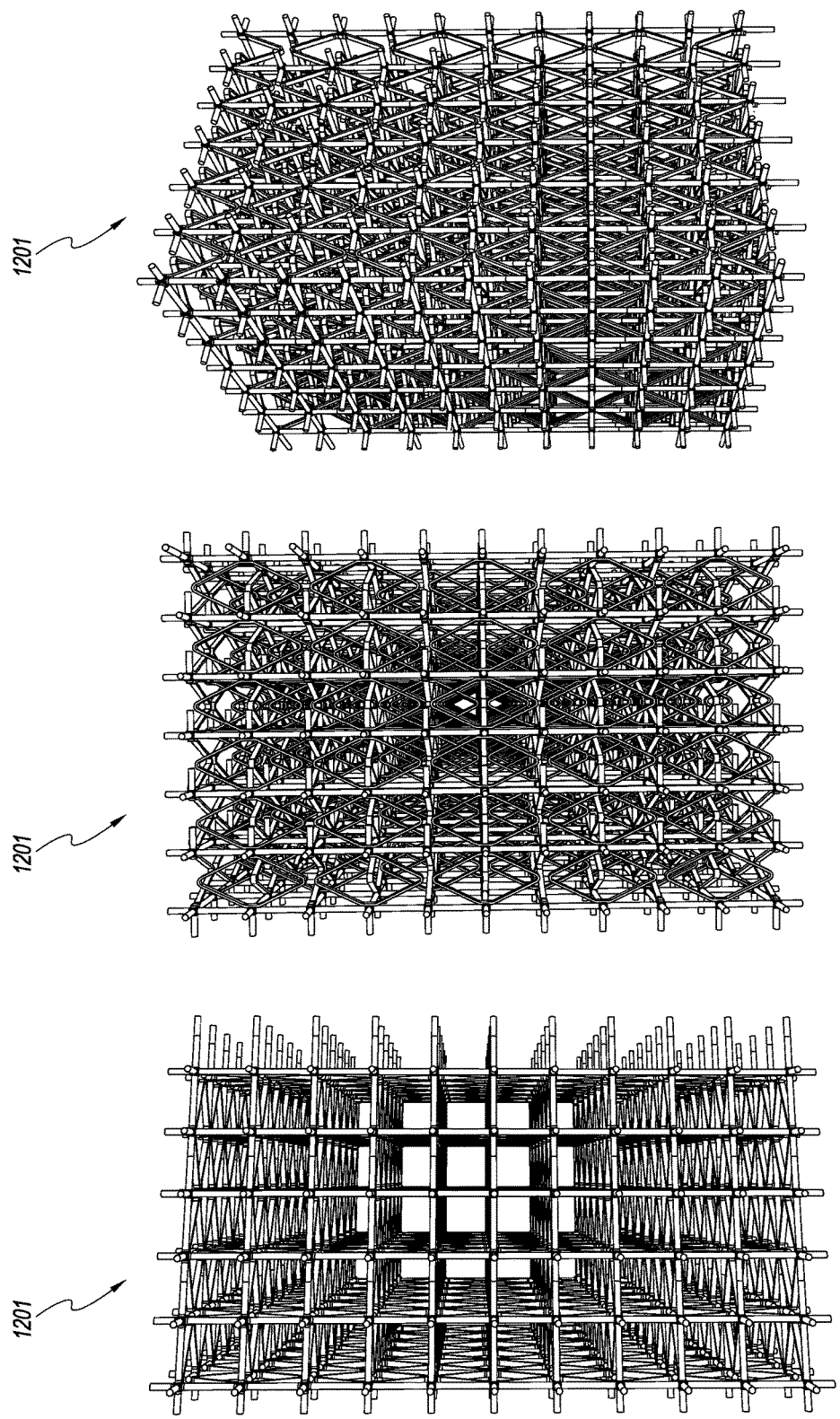

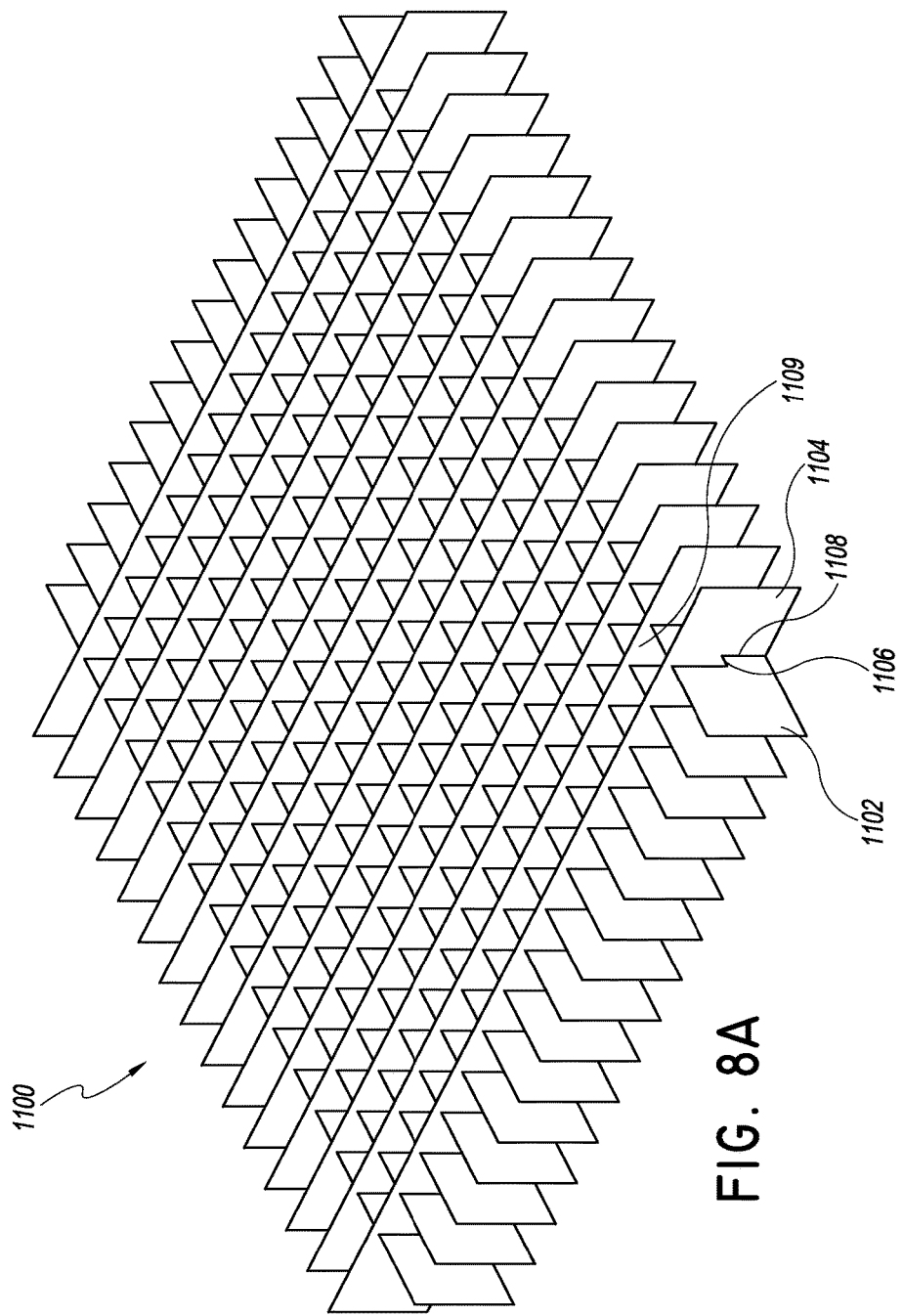

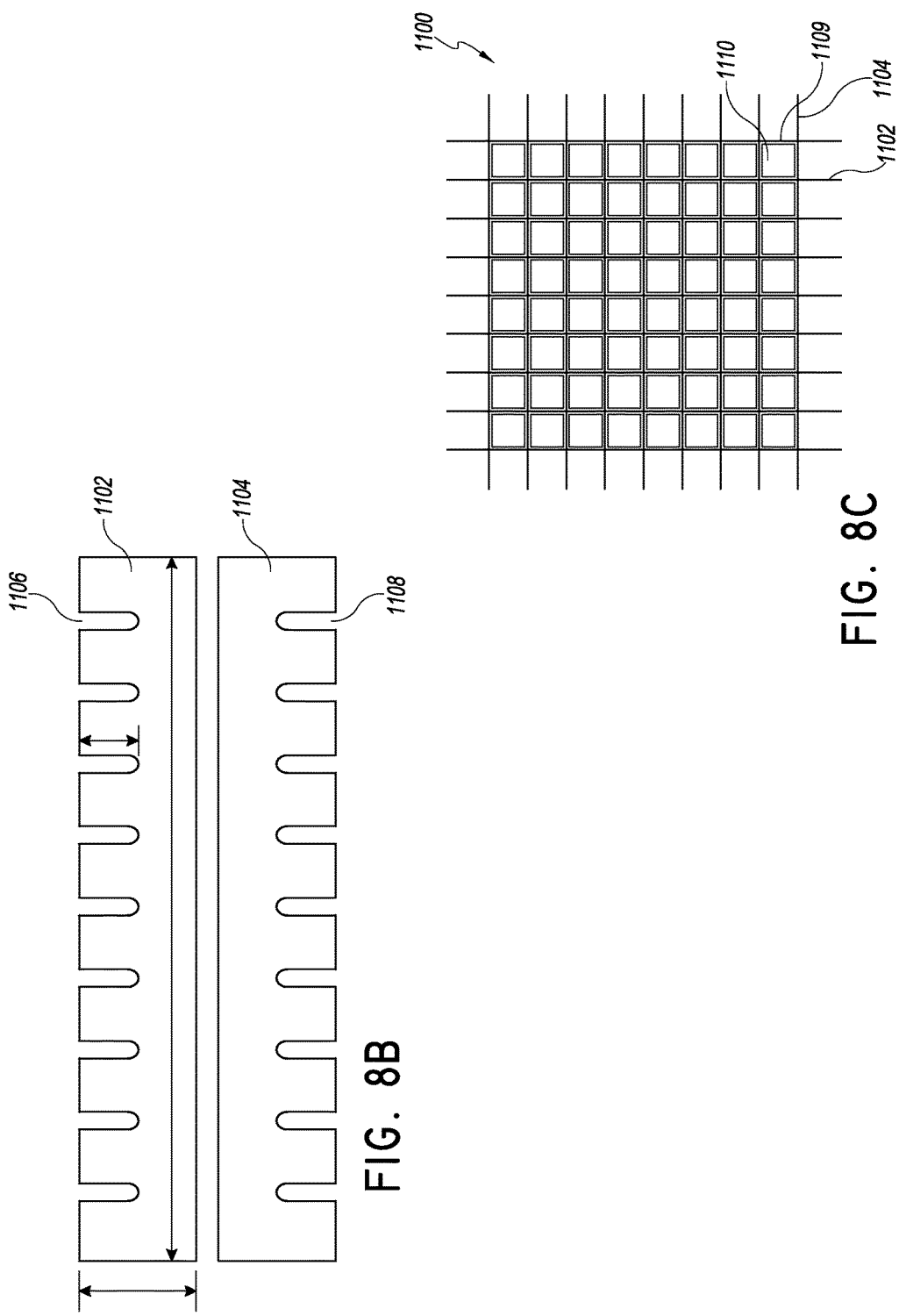

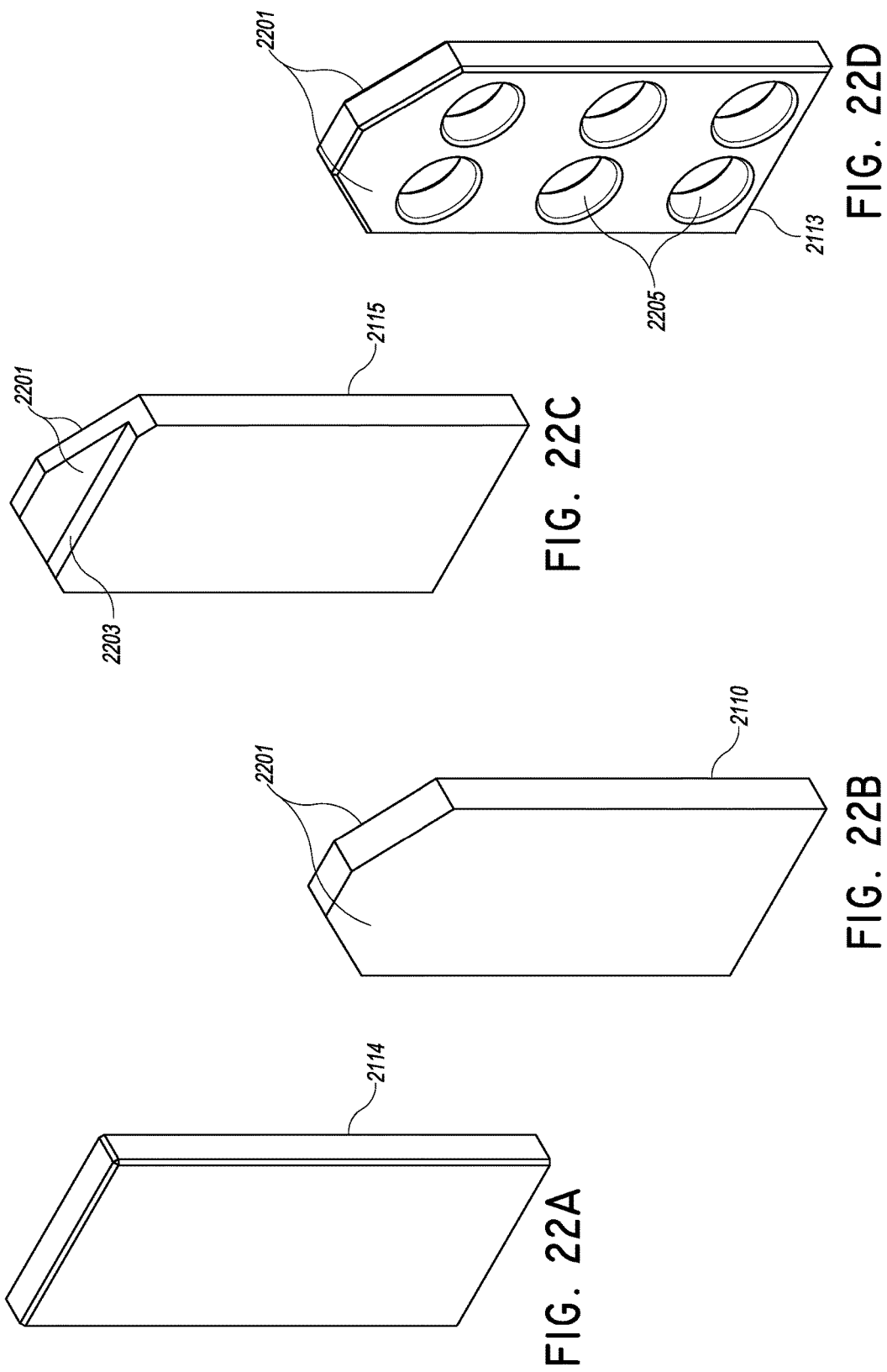

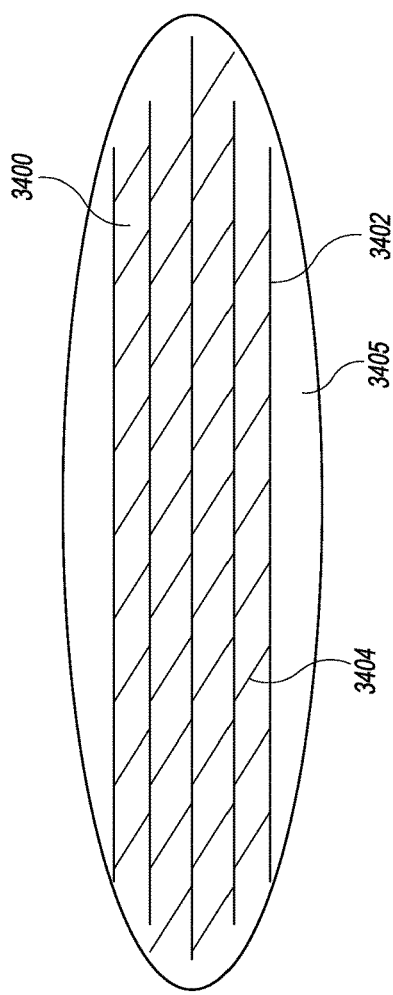
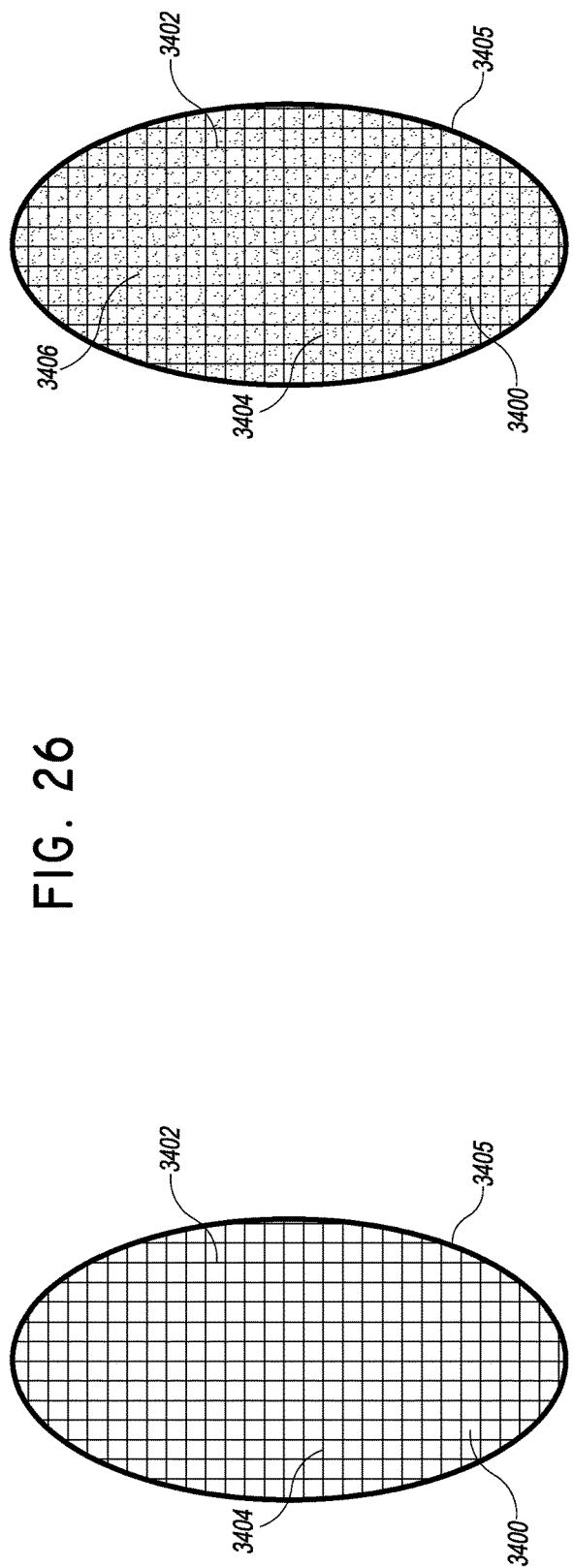
FIG. 26
FIG. 27A
FIG. 27B

NEGATIVE PRESSURE WOUND CLOSURE DEVICE

CROSS-REFERENCE TO RELATED APPLICATIONS

This application is a U.S. National Phase of PCT International Application No. PCT/US2013/050619, filed Jul. 16, 2013, entitled NEGATIVE PRESSURE WOUND CLOSURE DEVICE, which claims the benefit of U.S. Provisional Application No. 61/672,225, filed Jul. 16, 2012, entitled NEGATIVE PRESSURE WOUND CLOSURE DEVICE, U.S. Provisional Application No. 61/771,732, filed Mar. 1, 2013, entitled NEGATIVE PRESSURE WOUND CLOSURE DEVICE, and U.S. Provisional Application No. 61/780,629, filed Mar. 13, 2013, entitled NEGATIVE PRESSURE WOUND CLOSURE DEVICE. The contents of the aforementioned applications are hereby incorporated by reference in their entireties as if fully set forth herein. The benefit of priority to the foregoing applications is claimed under the appropriate legal basis, including, without limitation, under 35 U.S.C. §119(e).

BACKGROUND OF THE INVENTION

Field of the Invention

This application describes embodiments of apparatuses, methods, and systems for the treatment of wounds, specifically to aid in the closure of large wounds, in conjunction with the administration of negative pressure.

Description of the Related Art

Negative pressure wound therapy has been used in the treatment of wounds, and in many cases can improve the rate of healing while also removing exudates and other deleterious substances from the wound site.

Abdominal compartment syndrome is caused by fluid accumulation in the peritoneal space due to edema and other such causes, and results in greatly increased intra-abdominal pressure that may cause organ failure eventually resulting in death. Causes may include sepsis or severe trauma. Treatment of abdominal compartment syndrome may require an abdominal incision to permit decompression of the abdominal space, and as such, a large wound may be created onto the patient. Closure of this wound, while minimizing the risk of secondary infections and other complications, and after the underlying edema has subsided, then becomes a priority.

Other large or incisional wounds, either as a result of surgery, trauma, or other conditions, may also require closure. For example, wound resulting from sterniotomies, fasciotomies, and other abdominal wounds may require closure. Wound dehiscence of existing wounds is another complication that may arise, possibly due to incomplete underlying fascial closure, or secondary factors such as infection.

Existing negative pressure treatment systems, while permitting eventual wound closure, still require lengthy closure times. Although these may be combined with other tissue securement means, such as sutures, there is also a risk that underlying muscular and tissue fascial tissue is not appropriately reapproximated so as to permit complete wound closure. Further, when foam or other wound fillers are inserted into the wound, the application of negative pressure to the wound and the foam may cause atmospheric pressure to bear down onto the wound, compressing the foam downward and outward against the margins of the wound. This downward compression of the wound filler slows the healing process and slows or prevents the joining of wound margins.

Accordingly, there is a need to provide for an improved apparatus, method, and system for the treatment and closure of wounds.

SUMMARY OF THE INVENTION

Embodiments of the present invention relate to negative pressure wound closure devices, methods, and systems that facilitate closure of a wound. The devices, methods, and systems may operate to reduce the need for repetitive replacement of wound filler material currently employed and can advance the rate of healing. The devices, methods, and systems may be simultaneously used with negative pressure to remove wound fluids.

In one embodiment, a wound closure device comprises:
a stabilizing structure comprising a plurality of planar support structures, each planar support structure comprising a first plurality of beams intersecting with a second plurality of beams, the plurality of planar support structures being arranged parallel to one another;
a plurality of spring elements joining adjacent planar support structures, the plurality of spring elements providing for compression of the stabilizing structure so that the planar support structures come closer to one another.

In some embodiments, the beams are rigid. In some embodiments, the first plurality of beams intersects with the second plurality of beams at a right angle. Some embodiments may provide for each planar support structure to be substantially rigid within the plane of the support structure. In further embodiments, the planar support structure comprises one or more standoffs located on an outer plane or perimeter. In further embodiments, the standoffs are provided with one or more tissue anchors configured to engage tissue placed into contact with the device. In some embodiments, a first plurality of spring elements is located in a first plane perpendicular to the planar support structures, and a second plurality of spring elements is located in a second plane perpendicular to both the first plane and to the planar support structures. Some embodiments may provide for the first plurality of spring elements being located in a first plurality of parallel planes, the first plurality of parallel planes including the first plurality of rigid beams, and wherein the second plurality of spring elements are located in a second plurality of parallel planes, the second plurality of parallel planes including the second plurality of rigid beams. Some embodiments may provide spring elements comprising V-shaped members. In some embodiments, each planar support structure is identical. In some embodiments, a porous material such as foam surrounds one or more of the planar support structures. In further embodiments, the porous material surrounds the entire device. In some embodiments, the stabilizing structure comprises 2, 3, 4, 5 or more parallel planar support structures, with spring elements provided between each. In some embodiments, there may be an identical arrangement of spring elements between each of the planar support structures.

Another embodiment provides for a stabilizing structure comprising a plurality of cells provided side-by-side in a plane, each cell defined by one or more walls, each cell having a top end and a bottom end with an opening extending through the top and bottom ends in the direction perpendicular to the plane; wherein the stabilizing structure is configured to collapse significantly more within the plane than along the direction perpendicular to the plane.

In some embodiments, the stabilizing structure is constructed from a material selected from the group consisting of silicone, rigid plastics, and foam. In some embodiments, the cells are identical; in other embodiments, one or more of the cells are differently shaped from the remaining ones. The plane may extend in a horizontal direction. In some embodiments the walls may extend in a vertical direction. In some embodiments, the walls adjoin to adjacent cells. In some embodiments, the shape of each cell is selected from the group consisting of square, diamond, oblong, oval, and parallelepiped. In some embodiments, at least one wall of each cell includes a notch or a hole. In some embodiments, at least one wall of each cell is configured to fold against another wall of the cell. Further embodiments may provide for each cell to be connected to an adjacent cell by a joint, wherein the joints are more flexible than the walls. Some joints may be more flexible than other joints in the same cell. The stabilizing structure may comprise cells that are more collapsible in a first direction along the plane than in a second direction at an angle to the first direction along the same plane. Sometimes the second direction may be perpendicular to the first direction. The stabilizing structure may comprise a plurality of first strips extending in a first direction, and a plurality of intersecting strips extending in a second direction perpendicular to the first direction, wherein the structure is collapsible in the first and second directions.

In some embodiments, the one or more walls further comprise an insert disposed therein. The insert may be more rigid than the one or more walls, and may be insertable into a preformed pocket within the one or more walls. In some embodiments, the stabilizing structure comprises one or more inserts, and wherein each of the one or more walls are molded around an individual insert. The insert may have a rectangular configuration. The insert may have a rectangular configuration with two notches formed thereupon. In some embodiments, the insert comprises one or more longitudinal grooves extending in the direction of the plane. The insert may further comprise one or more holes disposed therethrough. In some embodiments, the holes are arranged in a 6×6 pattern. The one or more holes may be disposed on an edge of the insert.

In other embodiments, a stabilizing structure sized to be inserted into a wound, comprises:
at least one top strip extending in a first direction, the top strip comprising at least one notch extending partly therethrough and opening on a bottom side of the top strip;
at least one bottom strip extending in a second direction, the bottom strip comprising at least one notch extending partly therethrough and opening on a top side of the bottom strip;
wherein the at least one top strip and bottom strip are configured to be movably interlocked together by placing the notch on the top strip over the notch on the bottom strip, and
wherein the at least one top strip and the at least one bottom strip are configured to preferentially collapse along a first plane defined by the first and second directions, while remaining movably interlocked and substantially not collapsing along a third direction perpendicular to the first plane.

Additional embodiments provide for the at least one notch on the top strip and the at least one notch on the bottom strip to be dimensioned such that, when movably interlocked together, the top strip does not extend substantially above the bottom strip in the third direction. In further embodiments, the stabilizing structure comprises at least two top strips and at least two bottom strips so as to form at least one quadrilateral space bounded by two top strips and two bottom strips.

Embodiments of the wound closure device disclosed herein may also comprise a porous material surrounding the entire stabilizing structure. The porous material may be foam. In some embodiments, porous materials may surround or be within each cell, quadrilateral space or other interior portions of the stabilizing structure. In some embodiments, the stabilizing structure may be insertable into a sock or enclosure formed of porous material such that the porous material covers at least a portion of an outer perimeter of the stabilizing structure. In some embodiments, separate porous material layers may be provided above, below, or on both upper and lower layers of the stabilizing structure.

In other embodiments, a stabilizing structure for insertion into a wound comprises:
at least one top strip extending in a first direction;
at least one bottom strip extending in a second direction;
wherein the at least one top strip and bottom strip are configured to be movably interlocked using an interlock mechanism, and
wherein the at least one top strip and the at least one bottom strip are configured to preferentially collapse along a first plane defined by the first and second directions, while remaining movably interlocked and substantially not collapsing along a third direction perpendicular to the first plane.

In some embodiments, the interlock mechanism comprises: one of the at least one top strip or bottom strip comprising two parallel clasps extending in the third direction; the other of the at least one top strip or bottom strip comprising a projection extending in the third direction; and wherein the two parallel clasps rotatably engage with the projection so as to rotate about the projection in the first plane while remaining substantially fixed in the third direction. In some embodiments, the interlock mechanism comprises: one of the top strip or the bottom strip comprising a projection with an enlarged distal end, the other of the top strip or bottom strip comprising a cup-shaped member configured to receive the enlarged distal end of the projection therein; and wherein the top strip and bottom strips are rotatably engaged so as to rotate about the projection in the first plane without disengaging in the third direction. In some embodiments, the interlock mechanism comprises: one of the at least one top strip or bottom strip comprising four clasps disposed at perpendicular angles to each other extending in the third direction; the other of the at least one top strip or bottom strip comprises a projection extending in the third direction; and wherein the two parallel clasps rotatably engage with the projection so as to rotate about the projection in the first plane while remaining substantially fixed in the third direction. Some embodiments may also comprise an uncompressed volume defined by the height of the stabilizing structure and the area of the stabilizing structure in the first plane when the first and second directions defined by the at least one top strip and bottom strip are at perpendicular angles to each other, and wherein the stabilizing structure, when compressed, defines a compressed volume that is at least 15% smaller than the uncompressed area.

Additional embodiments provide for the top strip comprising at least one notch extending partly therethrough and opening on a bottom side of the top strip, and the bottom strip comprising at least one notch extending partly therethrough and opening on a top side of the bottom strip. In such an embodiment, the interlock mechanism places the notch on the top strip over the notch on the bottom strip. In some embodiments, the at least one notch on the top strip and the at least one notch on the bottom strip to be dimensioned such that, when movably interlocked together, the top strip does not extend substantially above the bottom strip in the third direction. In further embodiments, the stabilizing structure comprises at least two top strips and at least two bottom strips so as to form at least one quadrilateral space bounded by two top strips and two bottom strips.

In some embodiments, a stabilizing structure is provided for insertion into a wound, comprising a plurality of elongate strips arranged in parallel (or generally in parallel), and a plurality of intervening members connecting the elongate strips, wherein the plurality of intervening members are configured to pivot relative to the strips to allow the plurality of elongate strips to collapse relative to one another; wherein the intervening members between a first strip and a second strip are configured to pivot independently of the intervening members between a second strip and a third strip.

In certain embodiments, the intervening members are connected to the elongate strips via at least one joint. In particular embodiments, the joint is a hinge. In some embodiments, the hinges are configured to collapse in one direction. In particular embodiments, the joints are configured to restrict the movement of the intervening members. In certain embodiments, the elongate strips are rigid. In certain embodiments, the elongate strips are configured to bend along their length. In some embodiments, the elongate strips can be constructed from a material selected from the group consisting of silicone, rigid plastics, semi-rigid plastics, biocompatible materials, flexible plastic materials, composite materials, and foam. In some embodiments, the intervening members are constructed from a material selected from the group consisting of silicone, rigid plastics, semi-rigid plastics, biocompatible materials, flexible plastic materials, composite materials, and foam.

In some embodiments, the stabilizing structure comprises a plurality of intervening members between adjacent elongate strips to define a row of cells between each pair of adjacent elongate strips. In some embodiments, the cells are in the shape of a diamond. In particular embodiments, the cells in a row between adjacent elongate strips are configured to collapse together as the adjacent strips collapse relative to one another. In some embodiments, the rows of cells between adjacent strips are configured to collapse in a first direction, and one or more rows of cells between adjacent strips are configured to collapse in a second direction opposite the first direction. In some embodiments, all of the rows of cells of the stabilizing structure are configured to collapse in the same direction.

In some embodiments, the intervening members between the first strip and the second strip are offset relative to intervening members between the second strip and the third strip. In certain embodiments, foam surrounds the elongate strips and the intervening members. In some embodiments, foam is contained between adjacent elongate strips.

In certain embodiments, the intervening members comprise panels. In other embodiments, the intervening members comprise a plurality of bars configured to pivot relative to the elongate strips, and a plurality of pins connecting the elongate strips to the bars. In some embodiments, a plurality of stops is configured to restrict the rotational movement of the pins.

The embodiments disclosed herein may also comprise a drape configured to be placed over the wound closure device or stabilizing structure once inserted into a wound so as to create a fluid-tight seal on the skin surrounding the wound. Embodiments may also comprise a source of negative configured to be connected to the wound, and other associated apparatuses.

Further embodiments provide for methods of closing a wound, comprising:
 placing a wound closure device or stabilizing structure such as described herein within a wound;
 sealing the wound with a fluid-tight drape;
 fluidically connecting the wound to a source of negative pressure; and
 applying negative pressure to the wound via the source of negative pressure.

Further embodiments may provide for removing fluid from the wound site. In some embodiments, the wound closure device or stabilizing structure is placed into the wound such that the direction of collapse or compression of the wound closure device or stabilizing structure is parallel or substantially parallel with the surface of the skin. In some embodiments, the application of negative pressure causes the wound closure device or stabilizing structure to at least partly collapse. Further, the wound closure device or stabilizing structure may be at least partly collapsed or compressed prior to inserting the stabilizing structure into the wound. In some embodiments, the wound closure device or stabilizing structure is capable of collapse or compression to 40% or less, 30% or less, 20% or less, 10% or less or even 5% or less of one of its original dimensions (e.g., along one of its lengths). Some embodiments provide for reducing the wound area by at least 50% upon the application of negative pressure.

Additional embodiments of a negative pressure wound closure system may comprise:
 a stabilizing structure such as described herein;
 a drape sized and configured to be placed over the stabilizing structure and to form a substantially fluid-tight seal against a region of skin surrounding the wound; and
 a source of negative pressure in fluid communication with the wound.

Other embodiments of wound closure devices, stabilizing structures and associated apparatuses are described below.

BRIEF DESCRIPTION OF THE DRAWINGS

Other features and advantages of the present invention will be apparent from the following detailed description of the invention, taken in conjunction with the accompanying drawings of which:

FIGS. 3A-D illustrate different views of embodiments of a wound closure device comprising a stabilizing structure.

FIGS. 4A-E illustrate different views and photographs of embodiments of a wound closure device comprising a stabilizing structure.

FIGS. 8A-E illustrate additional embodiments of a wound closure device comprising a stabilizing structure.

FIGS. 21A-E are photographs of various embodiments of stabilizing structures comprising inserts disposed therein.

FIGS. 22A-F illustrate various embodiments of inserts that may be used in stabilizing structures.

FIG. 26 schematically illustrates an embodiment of a stabilizing structure.

FIG. 27A illustrates a top view of an embodiment of an oval shaped stabilizing structure.

FIG. 27B illustrates a top view of an embodiment of an oval shaped stabilizing structure with foam.

DETAILED DESCRIPTION OF THE PREFERRED EMBODIMENTS

Figure 1:
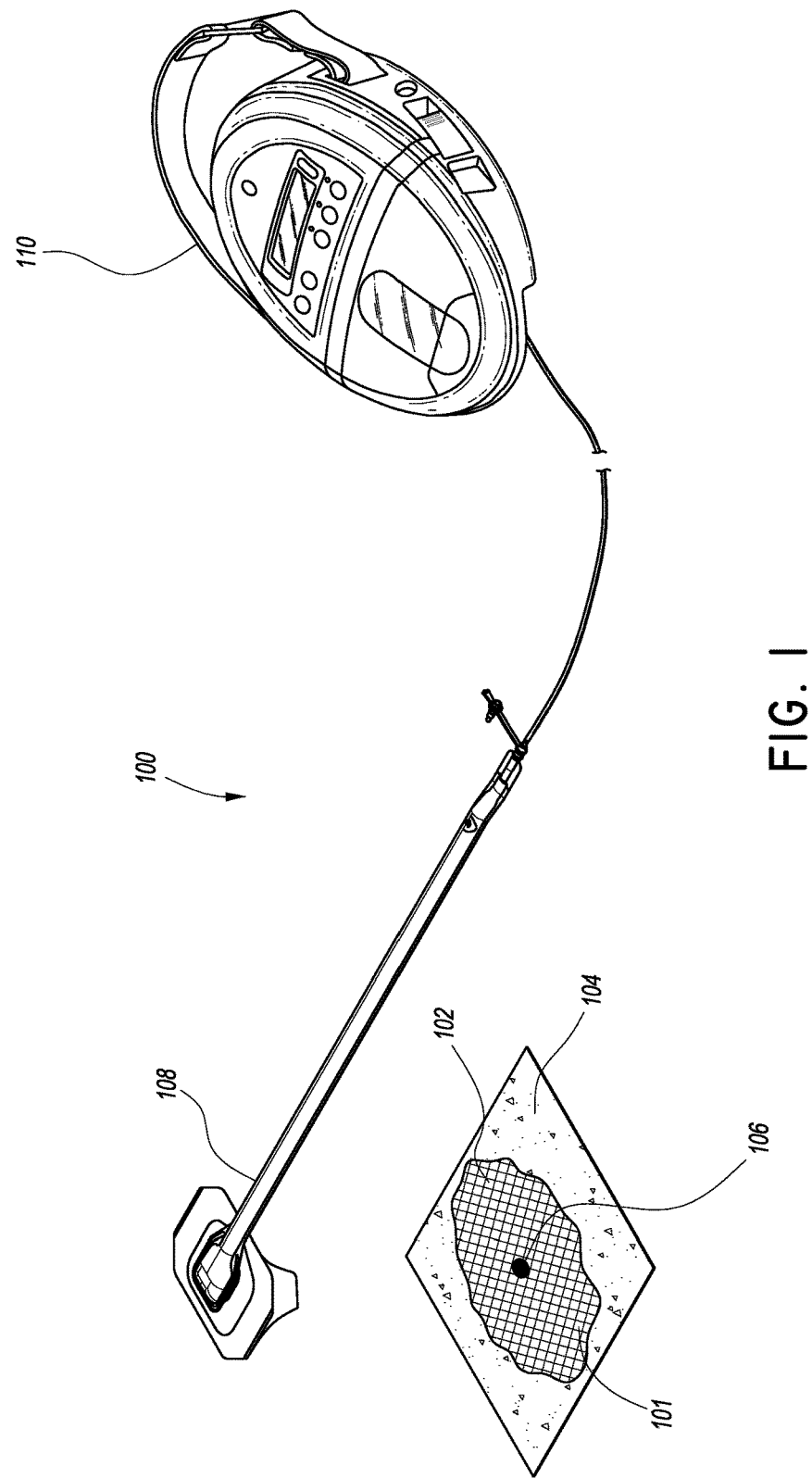
FIG. 1 illustrates an embodiment of a negative pressure treatment system.

Embodiments disclosed herein relate to apparatuses and methods of treating a wound with reduced pressure, including pump and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

As is used herein, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −20 mmHg and −200 mmHg. Note that these pressures are relative to normal ambient atmospheric pressure. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include application Ser. No. 11/919,355, titled "Wound treatment apparatus and method," filed Oct. 26, 2007, published as US 2009/0306609; and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described herein may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227.

It will be understood that throughout this specification in some embodiments reference is made to an elongate, elongated or longitudinal strip or strips. It is to be understood that these terms are to be broadly construed and refer in some embodiments to an elongate material having two parallel or substantially parallel faces, where in cross-section a thickness of the material as measured perpendicular to the faces is relatively smaller than a height of the material measured parallel to the faces. While in some embodiments the strips may be constructed from discrete lengths of material, in other embodiments the strips may simply refer to elongate portions of an overall structure having two parallel or substantially parallel faces. The strips in some embodiments have a rectangular or generally rectangular-shaped faces, wherein a length of the face is longer than the height of the face. In some embodiments, the length of the face may be more than 2 times, 4 times, 6 times, 8 times or 10 times greater than the height of the face.

As used herein, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal," and "lateral" may also be used to describe the stabilizing structures and wound closure devices described throughout this specification. When describing these structures or devices, these terms should not be construed to require that the structures or devices necessarily be placed into a wound in a certain orientation, though in certain embodiments, it may be preferable to do so.

FIG. 1 illustrates an embodiment of a negative pressure treatment system 100 that comprises a wound packer 102 inserted into a wound 101. The wound packer 102 may comprise porous materials such as foam, and in some embodiments may comprise one or more embodiments of wound closure devices described in further detail herein. In some embodiments, the perimeter or top of any wound closure device inserted into the wound 101 may also be covered with foam or other porous materials. A drape 104 may be placed over the wound 101, and is preferably adhered or sealed to the skin on the periphery of the wound 101 so as to create a fluid-tight seal. An aperture 106 may be made through the drape 104—which can be manually made or preformed into the drape 104—so as to provide a fluidic connection from the wound 101 to a source of negative pressure such as a pump 110. Preferably, the fluidic connection between the aperture 106 and the pump 110 is made via a conduit 108. In some embodiments, the conduit 108 may comprise a RENASYS® Soft Port™, manufactured by Smith & Nephew. Of course, in some embodiments, the drape 104 may not necessarily comprise an aperture 106, and the fluidic connection to the pump 110 may be made by placing the conduit 108 below the drape. In some wounds, particularly larger wounds, multiple conduits 108 may be used, fluidically connected via one or more apertures 106.

In some embodiments, the drape 104 may be provided with one or more corrugations or folds. Preferably, the corrugations are aligned along the longitudinal axis of the wound, and as such may support closure of the wound by preferentially collapsing in a direction perpendicular to the longitudinal axis of the wound. Such corrugations may aid in the application of contractile forces parallel to the wound surface and in the direction of wound closure. Examples of such drapes may be found in application Ser. No. 12/922,118, titled "Vacuum Closure Device," filed Nov. 17, 2010 (published as US 2011/0054365), which is hereby incorporated by reference in its entirety.

In use, the wound 101 is prepared and cleaned. In some cases, such as abdominal wounds, a non- or minimally-adherent organ protection layer (not illustrated) may be applied over any exposed viscera. The wound packer 102 is then inserted into the wound, and is covered with the drape 104 so as to form a fluid-tight seal. A first end of the conduit 108 is then placed in fluidic communication with the wound, for example via the aperture 106. The second end of the conduit 108 is connected to the pump 110. The pump 110 may then be activated so as to supply negative pressure to the wound 101 and evacuate wound exudate from the wound 101. As will be described in additional detail below and in relation to the embodiments of the foregoing wound closure devices, negative pressure may also aid in promoting closure of the wound 101, for example by approximating opposing wound margins.

Example 1

By means of a non-limiting example, an experiment was conducted to determine the effectiveness of an embodiment of the wound closure devices described above, with testing being performed on a cadaveric model. A midline incision was made through the peritoneum and into the abdominal cavity of the cadaver, which was then filled with two saline bags with a total capacity of approximately 2 L so as to provide upward tension to simulate the effects of abdominal edema and organ swelling that may be seen, for example, in abdominal compartment syndrome. These bags, together with the intestines, were placed into the wound cavity underneath an organ protection layer, as provided in the Renasys® A/B treatment kit (Smith & Nephew).

Figure 2:
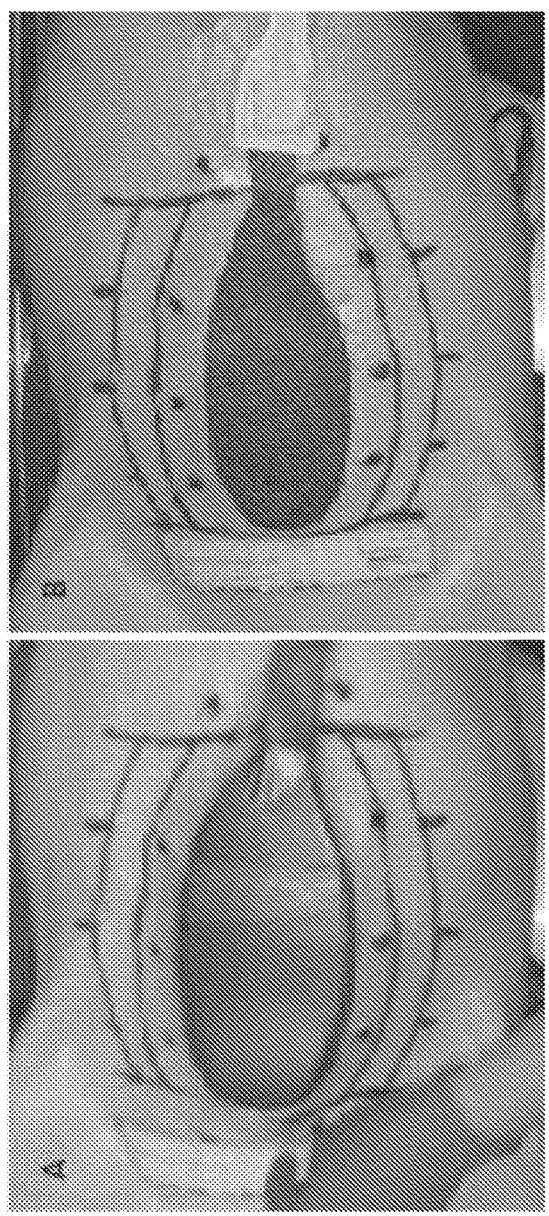
FIGS. 2A-B are before and after photographs of experiments performed to determine the efficacy of embodiments of wound closure devices.

With reference to FIG. 2A, a piece of black foam was inserted into the abdominal incision, sealed with a drape, and connected to a source of negative pressure via a fluidic connection (here, a Soft Port™ suction port assembly manufactured by Smith & Nephew). FIG. 2B illustrates the area of the wound after activation of the source of negative pressure. Negative pressure was then applied at 80, 120, and 180 mmHg. With all three of these negative pressure levels, there was no significant difference to the amount of wound margin contraction achieved, although vacuum levels below 80 mmHg did not appear to contract the wound margins as much. This was true in all of the other subsequent experiments described herein.

Wound area measurements were taken before and after activation of the negative pressure source. In this example, the size of the wound area before and after application of negative pressure decreased from 167 $mm^2$ to 126 $mm^2$. This is a difference of 25%.

Stabilizing Structures and Wound Closure Devices
of FIGS. 3A-4E

FIGS. 3A-D illustrate different views of an embodiment of a wound closure device comprising a stabilizing structure 1701. Here, the stabilizing structure 1701 comprises a first set of beams 1703 that are rigidly or semi-rigidly attached or bonded to a second set of intersecting beams 1705. These beams 1703, 1705 form a planar support structure 1702 that is preferably substantially rigid within a plane. The beams 1703, 1705 may meet at right angles to each other (although other configurations, e.g., honeycombs are possible). Two or more planar support structures 1702 may be joined together to form the stabilizing structure 1701, and each planar support structure 1702 is preferably separated from the other by spring elements 1711 and 1713, described in further detail below. The number of planar support structures 1702 used in the stabilizing structure may be tailored in relation to the size of the wound. For example, there may be 2, 3, 4, 5 or more planar support structures 1702 arranged parallel or substantially parallel to one another. The spring elements 1711, 1713 are preferably arranged so as to allow for compression of the stabilizing structure 1701 in one direction so as to bring the planar support structures 1702 closer together. In a preferred embodiment, the stabilizing structure 1701 may collapse to 40% or less of its original size, preferably 30% or less of its original size; more preferably, 20% or less of its original size; even more preferably, 10% or less of its original size. In some embodiments, the stabilizing structure 1701 may collapse to 5% or less of its original size.

The spring elements 1711, 1713 are preferably resiliently flexible and biased to be resiliently collapsible along a direction perpendicular to the plane defined by the planar support structure 1702. In some embodiments, the elements 1711, 1713 may be inelastic, and retain their shape when collapsed. In such embodiments, the spring elements or the stabilizing structure may be constructed with a ratchet mechanism that maintains the spring elements 1711, 1713 in their collapsed configuration.

Figure 3B:
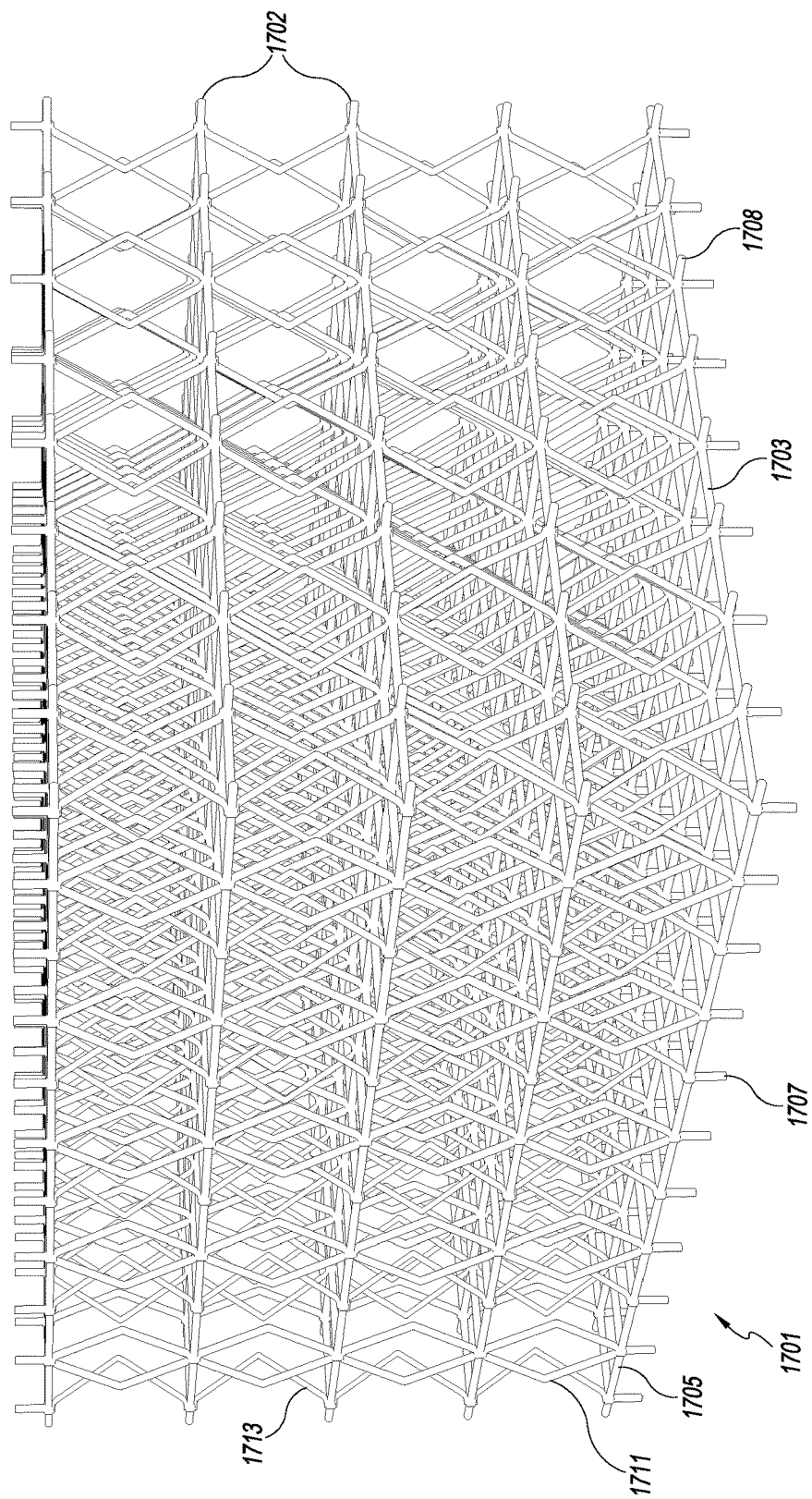
Figure 3D:
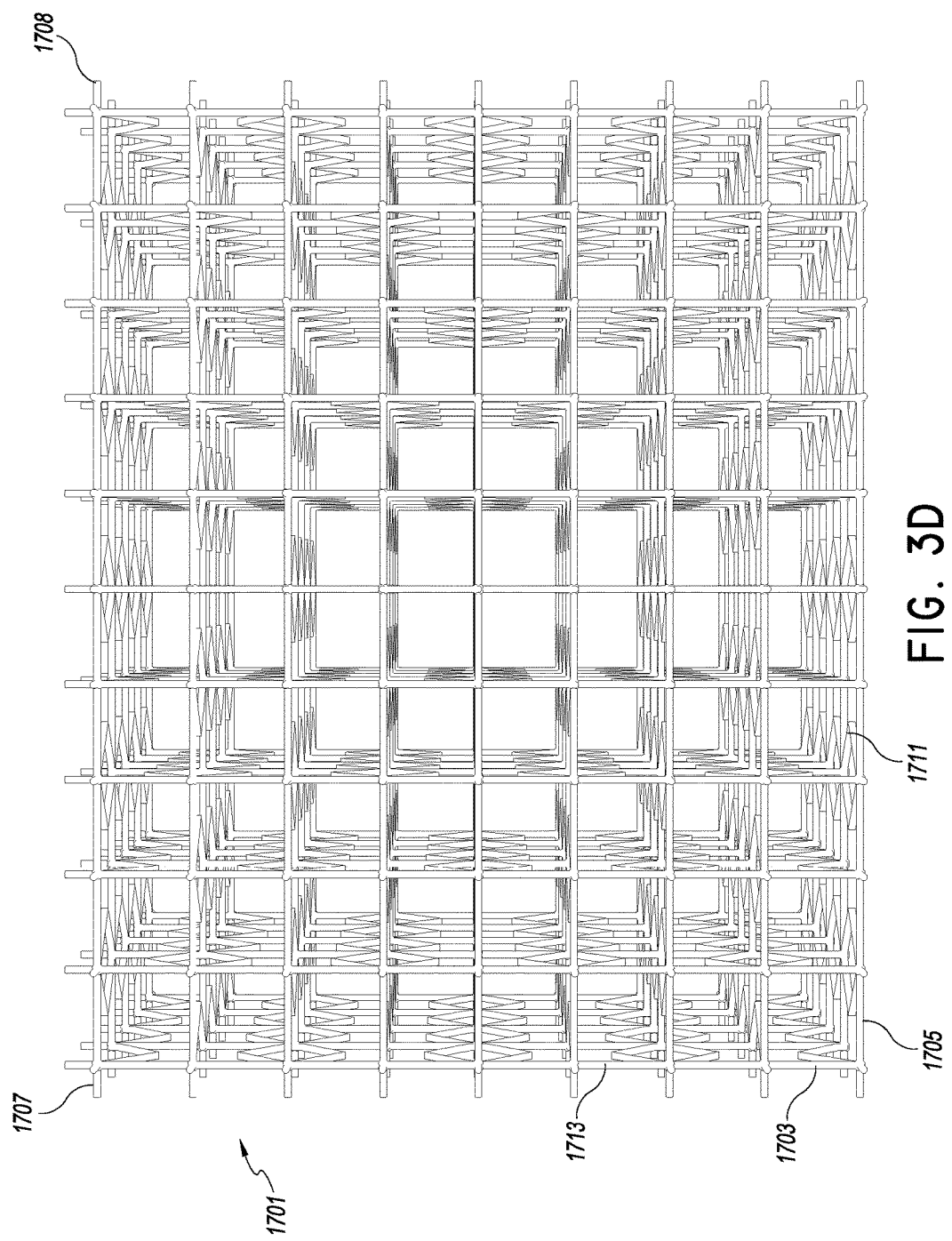
Figure 4A:
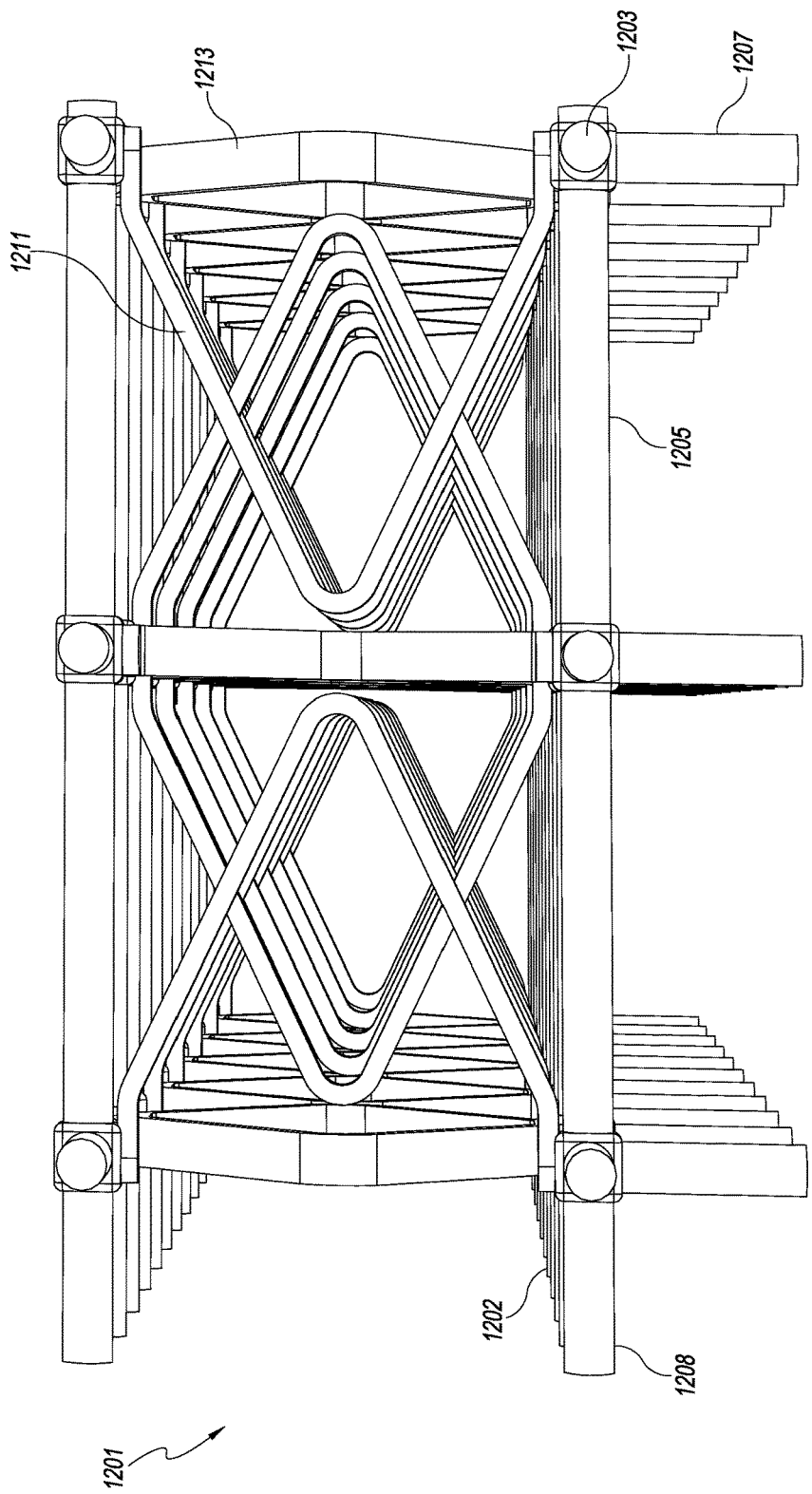
Figure 4B:
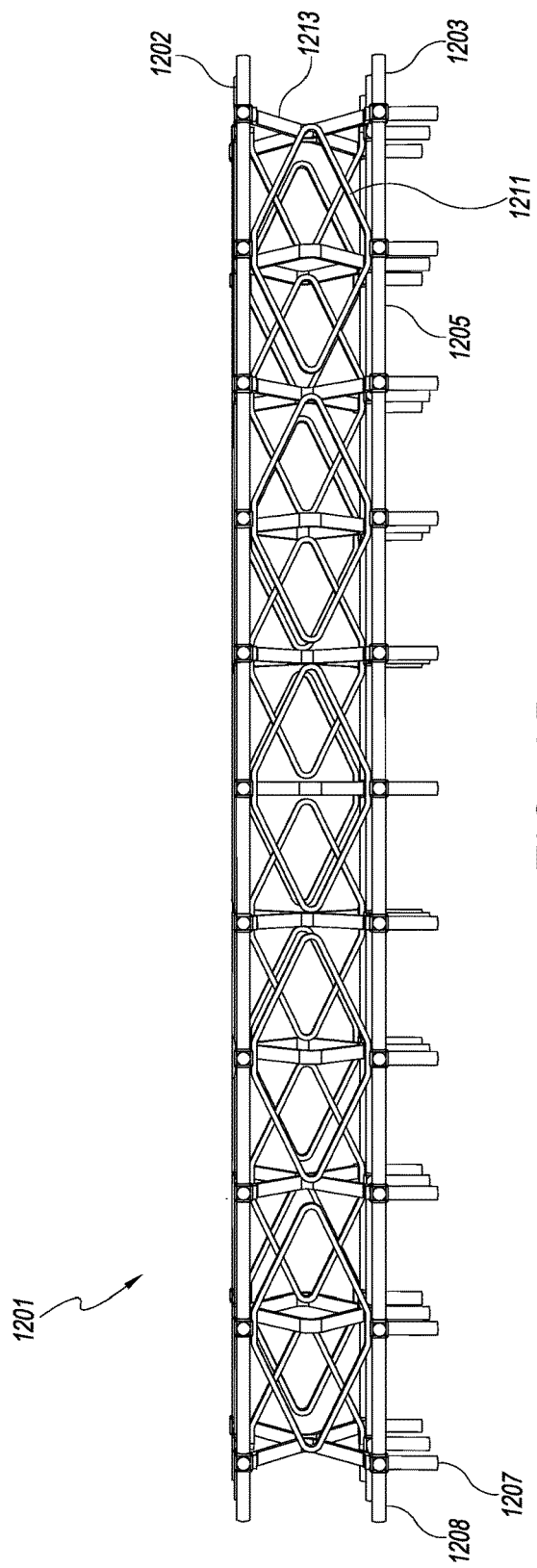
Figure 4C:
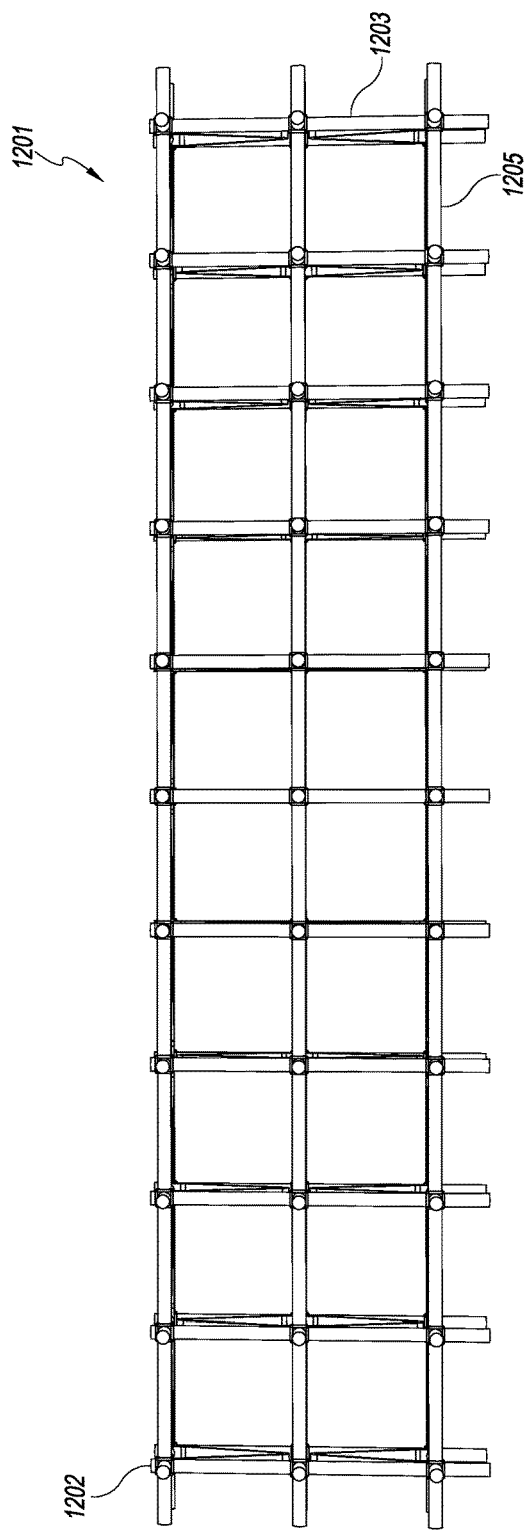
Figure 4D:
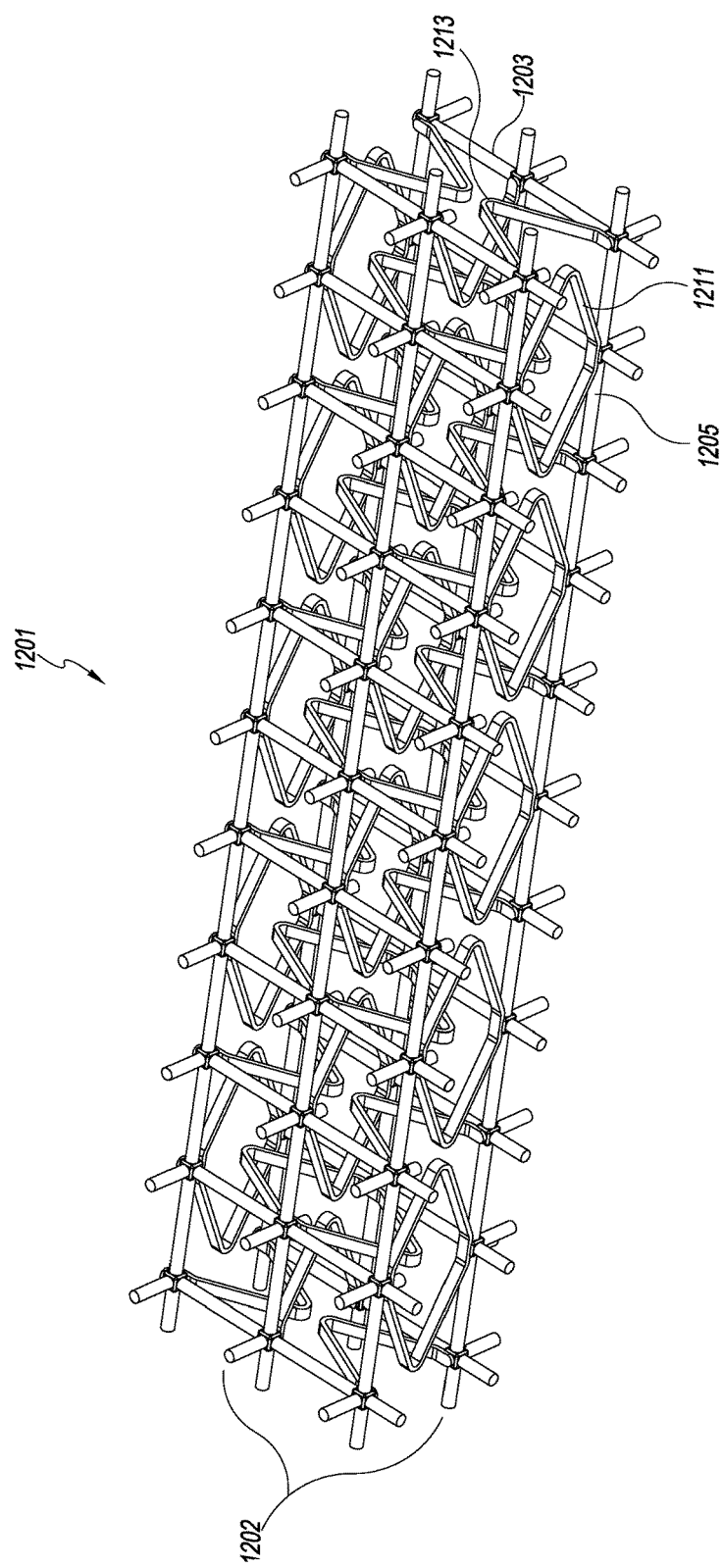

In a preferred embodiment, these spring elements 1711, 1713 may be V- or U-shaped. Each spring element may comprise two elongate portions that are bent relative to each other and form an obtuse angle (as shown in FIGS. 3A-3C), or an acute angle (as shown in FIG. 4A). Spring elements 1711 preferably run in a plane parallel to beam 1705, and may be attached to either the beam 1703 or 1705. Similarly, spring elements 1713 preferably run in a plane parallel to beam 1703, and may be attached to either the beam 1703 or 1705. For both spring elements 1711, 1713, a preferred attachment point is at the junction between beams 1703 and 1705. Preferably, the spring elements 1711 are arranged in a first plurality of parallel planes, which run parallel to the direction of the beam 1705, and the spring elements 1713 are arranged in a second plurality of parallel planes which run parallel to the direction of the beam 1703. The spring elements 1711 located between two adjacent planar support structures 1702 may be arranged in a repeating pattern within the first plurality of parallel planes. The spring elements 1713 located between two adjacent planar support structures 1702 may be arranged in a repeating pattern within the second plurality of parallel planes. In one embodiment as illustrated in FIGS. 3A and 3C, adjacent spring elements 1711 and 1713 form a diamond shape. However, different patterns, arrangements and numbers of spring elements may be employed. In some embodiments, the spring elements 1711, 1713 may have a spring constant ranging between 10 and 30 N/m, more preferably between 15 and 25 N/m, and even more preferably 23 N/m. In some preferred embodiments, the force required to compress seven spring elements by 15 mm equals 250 g. In some embodiments, the force required to compress the same seven springs by the same distance ranges between 180 and 230 g. In some embodiments, there are a total of four spring elements 1711, 1713 per 10 cm$^3$. Of course, one will recognize that factors such as the spring constants and/or number of springs may be tailored to the particular tissue type and wound closure desired, and that higher or lower spring constants or numbers of springs may be used.

Standoffs 1707 and 1708 may be provided at the edges or along the outer faces of the structure 1701, and which may be configured to contact the wound. In some embodiments, the standoffs 1707, 1708 may be extensions of the beams 1703, 1705, or may be provided separately. In some embodiments, the standoffs 1707, 1708 may be provided with hook or anchor elements configured to anchor tissue placed into contact with them. Additionally or alternatively, hook or anchor elements attached to the structure 1701 may be provided separately from or instead of the standoffs 1707, 1708. Such hook or anchor elements may be useful to enhance fascial tissue closure by ensuring that different tissue layers (e.g., muscle tissue, fat tissue) are closed at approximately the same rate. Preferably, the hook or anchor elements are configured so as to be have a release force (once engaged into tissue) that causes no or minimal pain to the patient while permitting sufficient pulling force to be applied thereto so as to allow for wound closure. In some embodiments, different anchor elements may be used to engage different types of tissue. For example, the release force to release an anchor element from subcutaneous fatty tissue may be lower than the force needed to release another anchor element from muscle tissue.

Further, the anchor elements, by virtue of their attachment to the surrounding tissue, may be useful in helping prevent a drape or other materials placed over the wound from going into the edges between the skin and the structure 1701. In some embodiments, the anchor elements may be broken off, which may aid in sizing the device as described below so as to fit into a wound. Additionally, all or part of the structure 1701 may be covered or embedded within a porous wound filler material. In such configurations, the standoffs 1707, 1708 may be used to provide additional securement to any such wound filler material.

In use, the stabilizing structure 1701 may be cut to size as appropriate to fit the wound. Optionally, a porous material such as foam may be placed around the perimeter of the structure 1701, and may be secured using one or more of the standoffs 1707, 1708. The porous material may also surround or envelop the entire device, for example by using a foam enclosure. Foam may also be added into the entire structure 1701, including its interior portions, and if this is done during manufacturing, the structure 1701 is preferably capable of withstanding a reticulation process. Such a device comprising foam will have composite tensile structures that are to be considered when inserting the device into the wound. When inserting the device into the wound, the stabilizing structure 1701 is preferably oriented such that the planar support structures 1702 are aligned such that they are perpendicular or substantially perpendicular to the general direction of wound closure, or perpendicular substantially perpendicular to the patient's skin. Optionally, an organ protection layer, which may comprise a polymer sheet or other flexible material, optionally provided with apertures, may be placed into contact with at least the bottom portion of the wound. A drape may be sealed over the skin surrounding the wound, and a source of negative pressure may be placed into fluid communication with the wound so as to effectuate wound closure. Further details regarding the drape, the application of negative pressure, and other apparatuses and methods that may be used with these stabilizing structures, are described below with respect to other embodiments.

FIGS. 4A-E illustrate different views and photographs of embodiments of a wound closure device comprising a stabilizing structure 1201. This embodiment is similar in some respects and in function to the embodiment described above in relation to FIGS. 3A-D, and share similar elements. The device comprises beams 1203 and 1205 that form a planar support structure 1202 separated by spring elements 1211 and 1213. Standoffs 1207 and 1208 may also be provided. Here, however, the spring elements 1211 and 1213 are thicker and have portions that are bent relative to each other at acute angles. Additionally, compared to FIGS. 3A-D, the structure 1201 has a greater volume and greater number of spring elements 1211, 1213. As illustrated best in FIG. 4D, the spring elements 1211 form a repeating diamond pattern within a first plurality of parallel planes, with the diamond location being staggered between adjacent parallel planes. A corresponding pattern is employed for spring elements 1213 with a second plurality of parallel planes. A similar configuration may be seen in FIGS. 3A-3D.

Example 2

Figure 5:
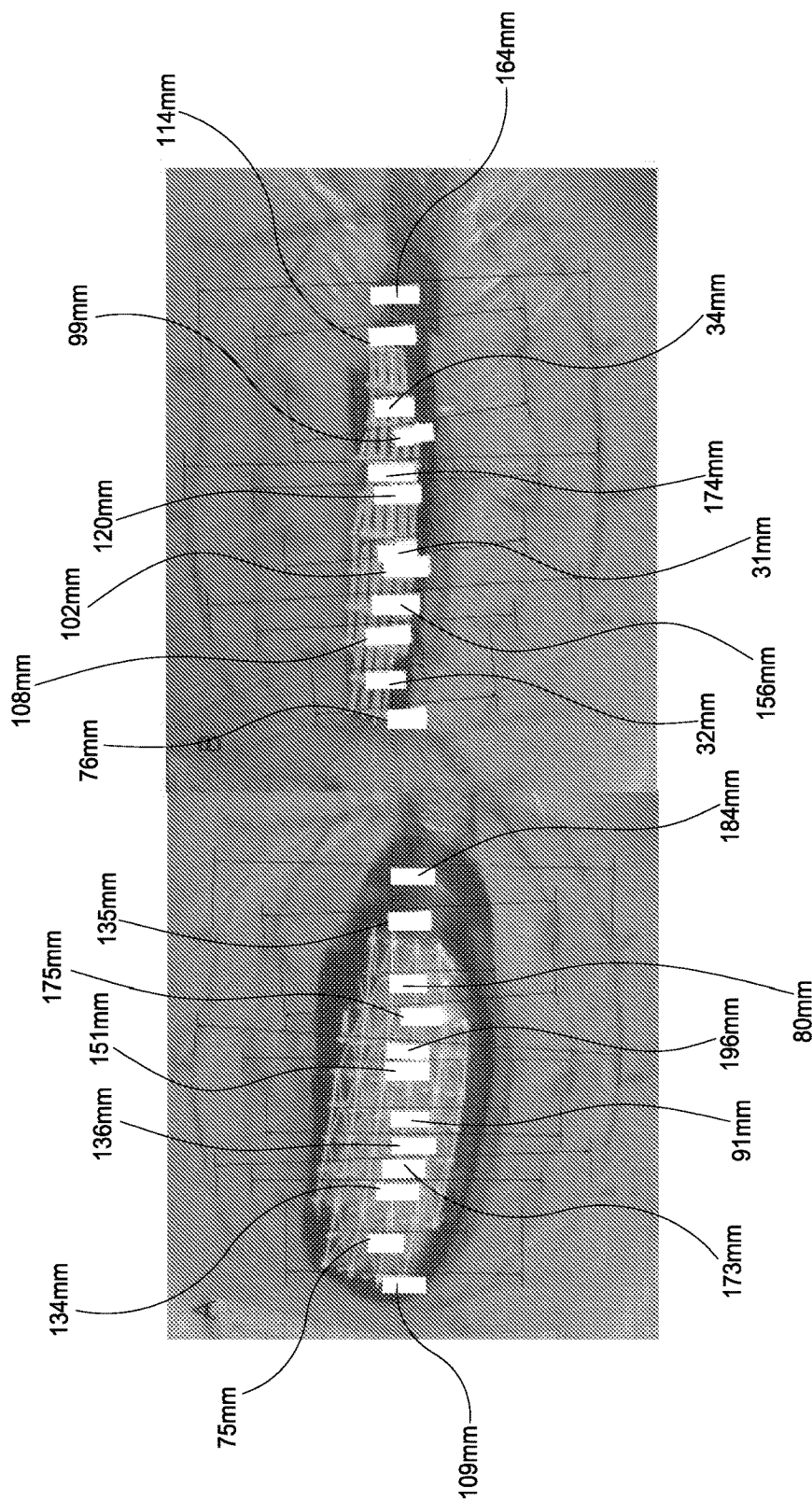
FIGS. 5A-B, 6A-B, and 7A-B are before and after photographs of experiments performed to determine the efficacy of certain embodiments of wound closure devices.

By means of a non-limiting example, an experiment was conducted to determine the effectiveness of an embodiment of the wound closure devices described above, with testing being performed on a cadaveric model. FIGS. 5A-B illustrate the results where a structure with foam, similar to the embodiments of FIGS. 4A-E, was placed into a wound. The perimeter of the structure was wrapped in a layer of foam.

Wound area measurements before and after application of negative pressure indicated that the wound area decreased by 64%, from 152 $mm^2$ to 55 $mm^2$.

Example 3

Figure 6:
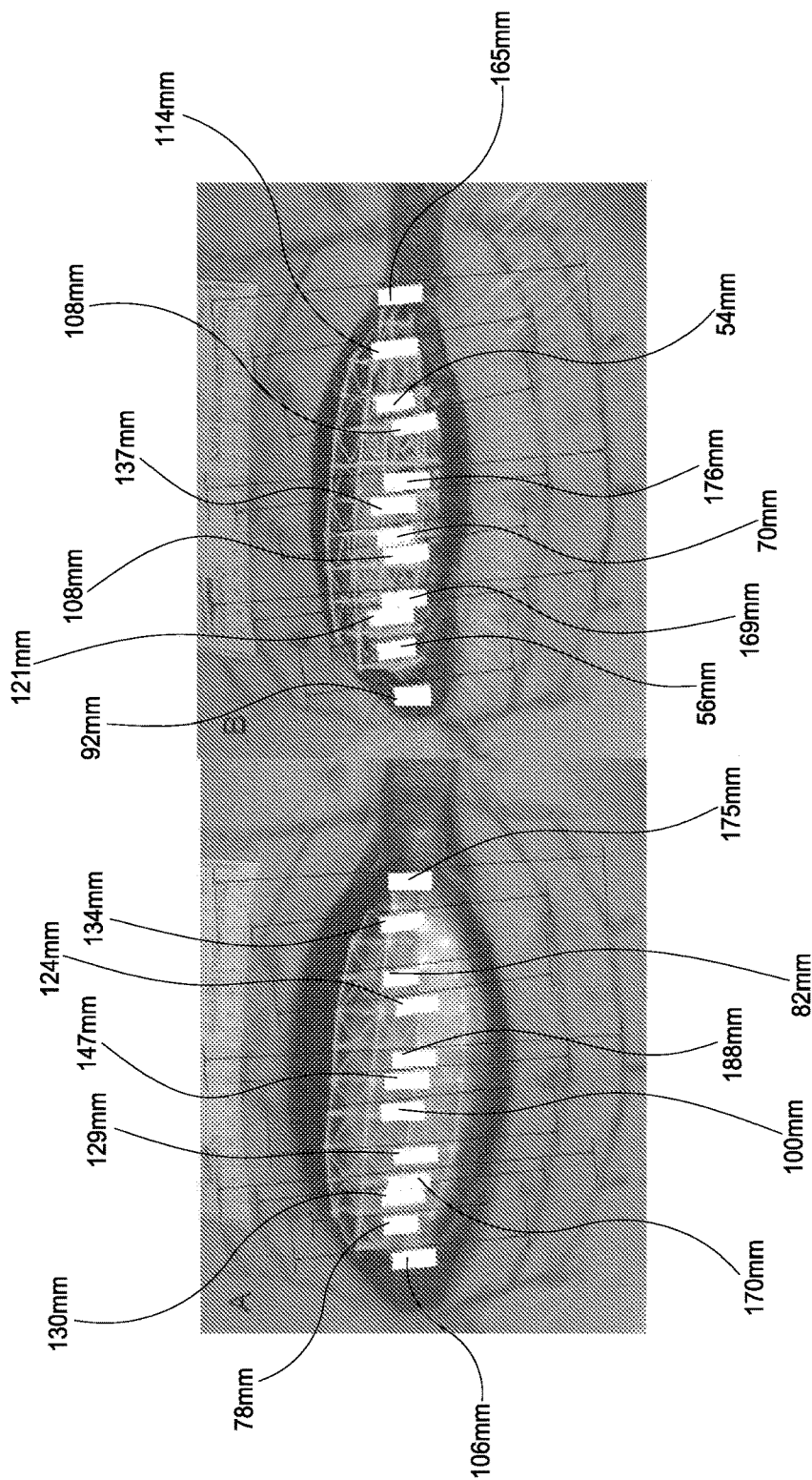

This non-limiting experiment tested a structure wrapped in foam and prestretched along its width and held in place by bendable plastic strips, but otherwise similar to the embodiments of FIGS. 4A-E. FIGS. 6A-B illustrate the wound size before and after application of negative pressure. Here, the wound area measured 154 $mm^2$ before the application of negative pressure, and 101 $mm^2$ afterwards, for a 34% reduction in wound area.

Example 4

Figure 7:
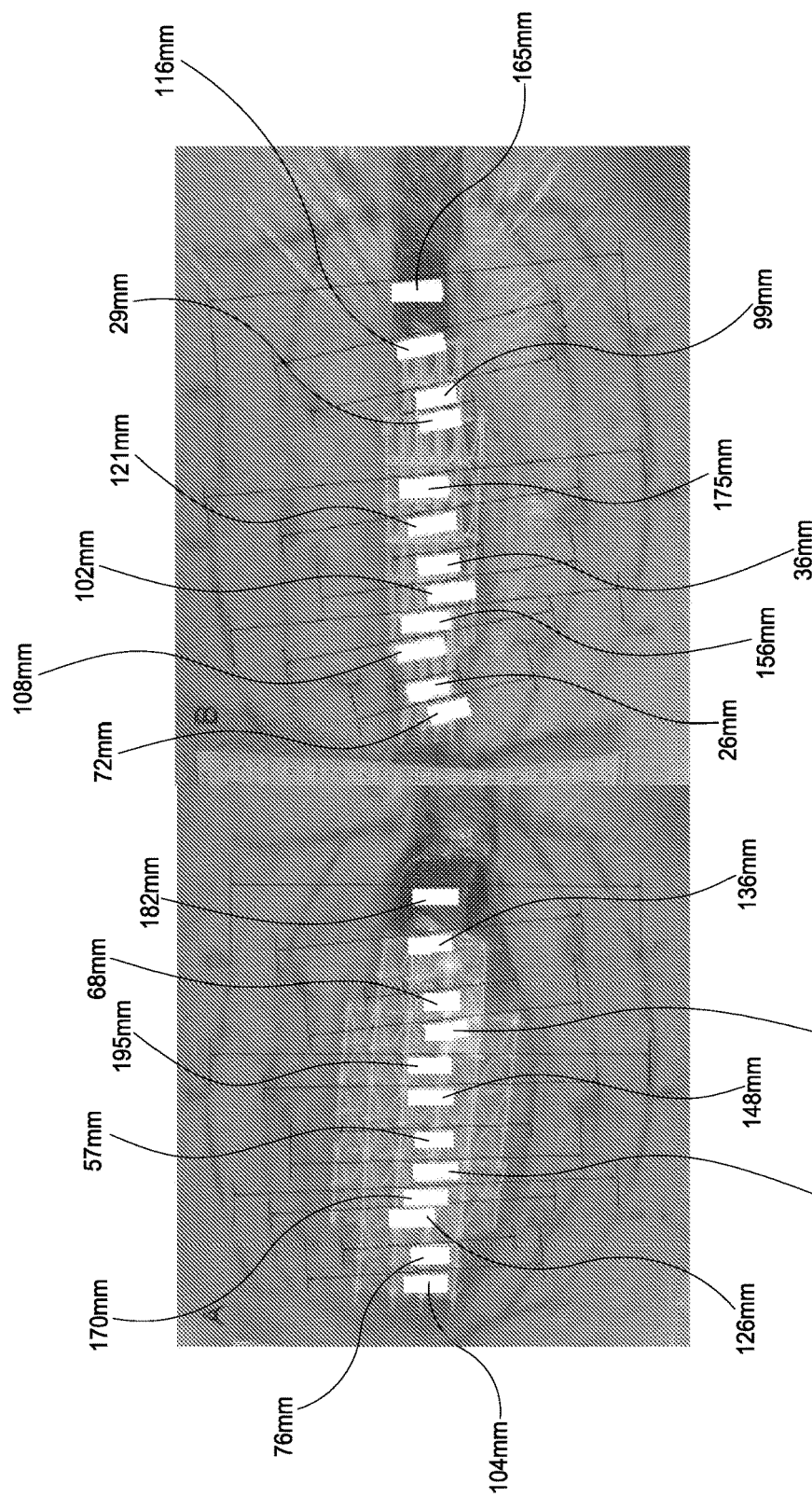

FIGS. 7A-B illustrate the non-limiting results of an experiment where a structure similar to the embodiment of FIGS. 4A-E was placed into a wound without any foam wrapping. The experiment was performed similarly to the other examples described herein, and here, the wound area measured 126 $mm^2$ before application of negative pressure, and 53 $mm^2$ afterwards, for a 58% reduction in wound area.

Stabilizing Structures and Wound Closure Devices of FIGS. 8A-16B 19-20B and 32

FIGS. 8A-E illustrate additional embodiments of a wound closure device comprising a stabilizing structure 1100. FIG. 2A shows a perspective view of an embodiment of a stabilizing structure 1100. Here, the stabilizing structure 1100 is preferably comprised of two or more interlocking strips (described below in more detail with relation to FIG. 8B) that extend in directions approximately perpendicular to each other when in a substantially uncollapsed configuration. The stabilizing structure is preferably configured to collapse in one direction or along a first plane while remaining relatively rigid and collapse-resistant in a direction perpendicular to the first direction or plane.

FIG. 8B illustrates side views of a bottom strip 1102 and a top strip 1104 that may be used to make a stabilizing structure 1100 such as the embodiment illustrated in FIG. 8A. Each of the top and bottom strips 1102, 1104 are preferably configured to movably interlock with each other, for example via matching notches 1106 and 1108. One or more notches 1106 may be provided on a top side of bottom strip 1102, and similarly, one or more notches 1108 may be provided on a bottom side of top strip 1104. When assembled together, the one or more top and bottom strips 1102, 1104 may be positioned so that the notches 1106, 1108 line up. Preferably, the top and bottom strips 1102, 1104 are positioned at substantially perpendicular angles to each other, thereby permitting the notches 1106, 1108 to slot together so as to create a movably interlocking structure. Typically, the number of notches 1106 on the bottom strip 1102 will equal the number of top strips 1108 that will form the stabilizing structure 1100, and vice versa. The notches 1106, 1108 are preferably shaped with a width that permits the strips 1102, 1104 to move from approximately perpendicular angles to angles far from perpendicular (i.e., close to parallel) to each other, thus permitting the stabilizing structure 1100 to articulate and collapse along one direction or plane.

In a preferred embodiment, the strips 1102, 1104 are constructed from a rigid or semi-rigid material, such as a polymer. Examples of suitable polymers include polyethylene, polypropylene, polyurethane, poly vinylchloride, polystyrene, polyacrylate, polymethyl methacrylate, PEEK, silicone, polycarbonate, composites and laminates, or combinations thereof. In some embodiments, the material may include compressed or "felted" reticulated foam. Of course, other materials, such as cardboard or metal may be used. Preferably, the materials may be at least partially porous so as to permit fluid to flow through the material. Further, such properties may aid in distributing negative pressure through the device and to the wound, and may aid in removing fluid from the wound dressing. Such materials may include, for example, low density polypropylene, foamed material, or sintered material. The material used does not necessarily need to be strong along the length of the strips 1102, 1104, but should preferably be able to withstand pressure applied to a top or bottom edge. Preferably, the material is capable of withstanding the pressure from atmospheric pressure exerted on a drape when up to 200 mmHg negative pressure is applied to the wound. In some embodiments, the material can withstand a force of 5 psi applied to a top or bottom edge.

In a preferred embodiment, each strip 1102, 1104 measures 180 mm long by 30 mm high. The thickness of the strips 1102, 1104 may range, for example, between 1.50 to 2.40 mm, although the thickness will be selected at least partly based on the ability of the material to withstand pressure being applied along its edge. The thickness is preferably balanced between keeping the material thin enough to minimize the compressed thickness of the stabilizing structure 1000, while keeping the material thick enough to avoid causing excessive localized pressure upon the wound bed. The notches 1106, 1108 may measure approximately 15 mm in height, and may be spaced apart from other notches by 18 mm. Although the notches 1106, 1108 are shown with rounded bottoms, these may also be cut with squared-off or triangular bottoms. In some embodiments, the rounded edges reduce stresses onto the strips 1102, 1104 so as to prevent fracture and crack propagation, and may also increase the springiness of the stabilizing structure 1100.

It will be understood that the interlocking strips 1102, 1104 may not necessarily need to be joined together via notches. Hinges or other devices could be used to provide the articulation or movable interlocking ability illustrated above. In some embodiments, hinges may be constructed from thinner areas of the same material used to construct the strips 1102, 1104, and are configured to flex or bend to a predetermined position. The stabilizing structure 1100 could also be molded as a single piece such that the interlocking strips 1102, 1104 form a single unit.

Returning to FIG. 8A, the perspective view illustrates an example of a stabilizing structure 1100 configuration with multiple interlocking top and bottom strips 1102, 1104 movably interlocked via multiple notches 1106, 1108. The intersections of two top strips 1102 and two bottom strips 1104 form a quadrilateral-shaped boundary space 1109. When the top and bottom strips 1102, 1104 are at perpendicular angles to each other, the space 1109 will be square or rectangular. However, as the stabilizing structure 1100 collapses along a direction or plane, the space 1109 will become more diamond- or parallelogram-shaped. The stabilizing structure 1100 will preferably comprise multiple spaces 1109, which form cells defined by the walls of the top and bottom strips and with openings on top and bottom ends.

FIG. 8C illustrates a top view of an embodiment of the stabilizing structure 1100 where a porous wound filler material 1110 has been placed into the quadrilateral-shaped boundary space 1109. Here, the porous wound filler material 1110 used is preferably soft and conformable so as to be able to adapt to the any change in the configuration of the stabilizing structure 1100 if it collapses. Preferably, the porous wound filler material is a foam, such as a polyurethane foam. This porous wound filler material may be cast around the stabilizing structure 1100 so as to completely encapsulate it. When used, the resulting stabilizing structure 1100 may be cut to size so as to fit into a wound. Such porous wound filler material 1110 may be used to aid in the fluid transmission or wicking of fluid from within a wound, and may also, when in contact with the wound (e.g., when used in negative pressure wound therapy), aid in the healing of the wound.

Figure 8D:
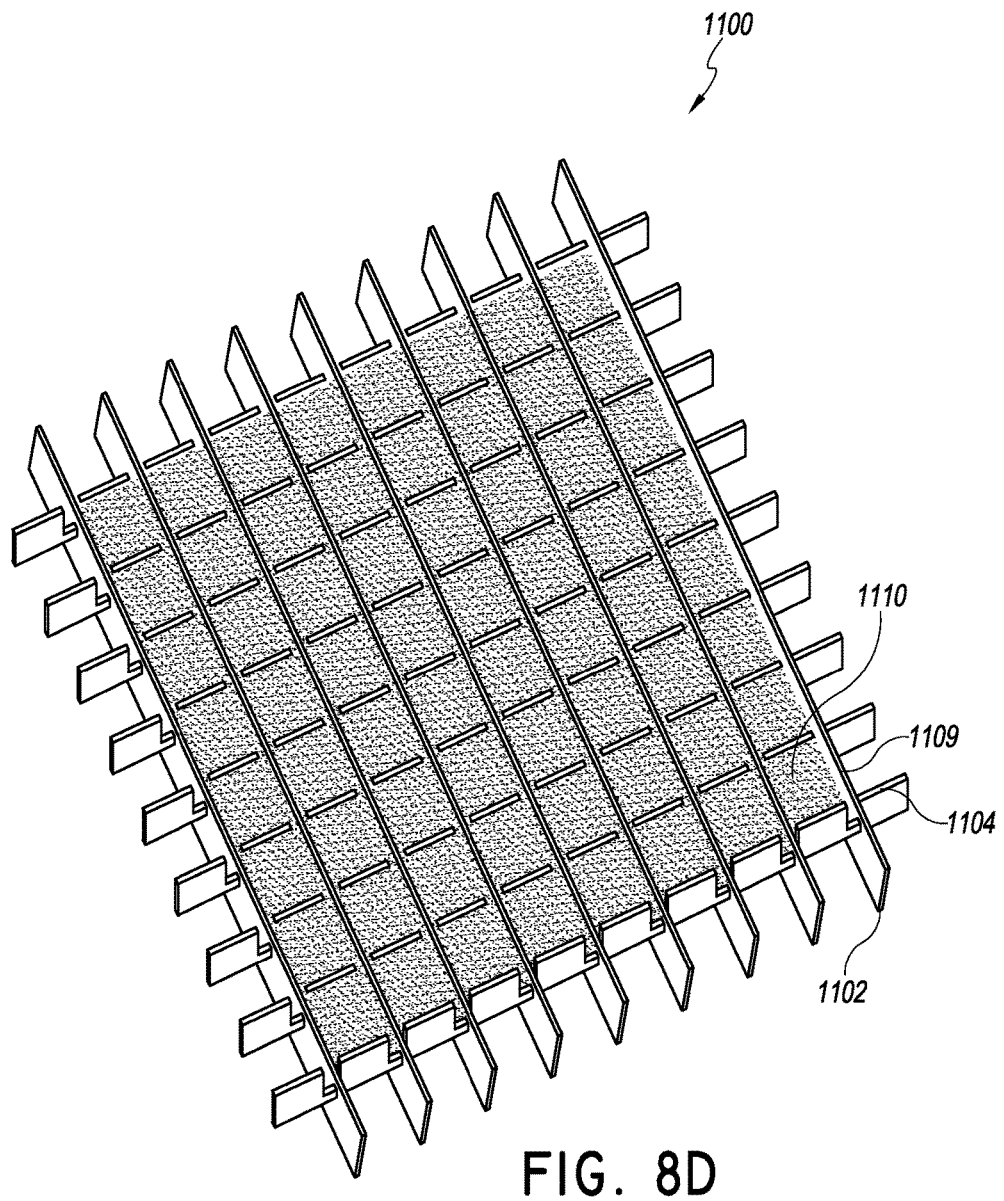

FIG. 8D illustrates a perspective photograph of an embodiment of the stabilizing structure 1100 with a porous wound filler material 1110 inserted into the spaces 1109. In some embodiments, additional porous wound filler material may also be used to encapsulate or surround the structure 1100. For example, a sock or wrap may be fitted around the structure 1100, and may for example be constructed from foam or gauze. When inserted into a wound, the stabilizing structure 1100 may be preferably oriented so as to collapse in a direction generally parallel with the orientation of collagen and other fibrous tissue fibers in the body. This orientation is sometimes referred to as Langer's lines or Kraissl's lines, and closing a wound in a direction coinciding with (and preferably parallel to) these lines may heal faster and more easily than attempting to close a wound in a direction perpendicular or opposed to these lines. It will be appreciated that the other embodiments of stabilizing structures described in this specification may also be oriented in the same manner with respect to Langer's lines or Kraissl's lines, or other landmarks.

In use, the stabilizing structure 1100 may be placed into a wound such that the upward facing portion of the structure 1100 is substantially rigid and resists collapse in the vertical direction once negative pressure is applied to the wound (e.g., once covered by a drape as described previously). A porous material such as foam may be placed around, into, and/or so as to surround or encapsulate the stabilizing structure 1100. In some embodiments, an organ protection layer as described previously may be placed into contact with at least the bottom portion of the wound. As negative pressure is applied, the structure 1100 will then preferably collapse in the plane perpendicular to the vertical direction, aiding in wound closure. Due to the relative incompressibility of the vertical dimension of the device, the pressure on the drape transmitted from the greater atmospheric pressure onto the wound will reduce the pressure applied to the stabilizing structure 1100 onto the wound margins in comparison to existing prior art devices (such as those illustrated in FIGS. 2A-B). Optionally, in this and other embodiments described herein, negative pressure may be applied so as to increase transmission of negative pressure to the sides of the wound rather than the bottom portions thereof. This may be accomplished, for example, by providing an organ protection layer that at least partially shields the bottom of the wound from negative pressure. In a preferred embodiment, the sides of the wound would be provided with at least 100 mmHg, preferably 120 mmHg, 140 mmHg, 180 mmHg, or 200 mmHg, while the bottom of the wound would be provided with at most 120 mmHg, more preferably 80 mmHg, 40 mmHg, 20 mmHg, or 10 mmHg.

Figure 8E:
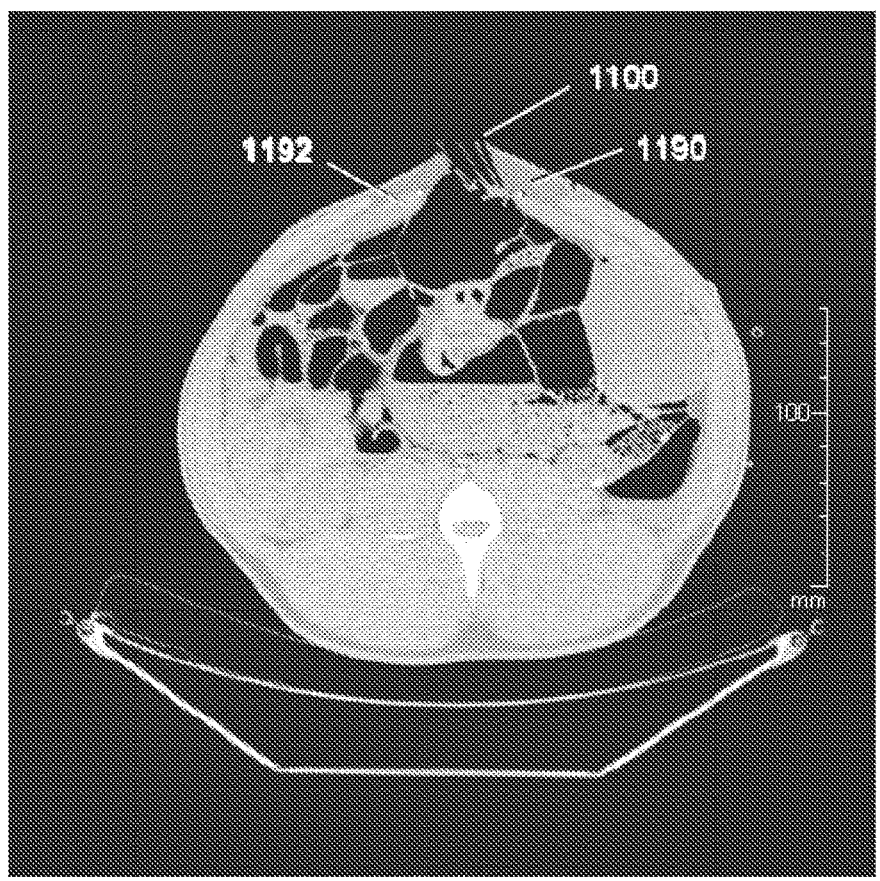

FIG. 8E illustrates a CT image of an embodiment of a stabilizing structure 1100 described in FIGS. 8A-D inserted into an abdominal wound. The tissue fascia layers are also visible, with a subcutaneous fat layer 1190 above a layer of muscle tissue 1192. With the application of negative pressure (as illustrated), improved fascial reapproximation and wound closure may be observed. In particular, the muscle tissue layers 1192 on opposite sides of the wound have been moved much closer together, while remaining attached to the other fascial layers. In measurements, the width of the wound along the view illustrated reduced from approximately 82 mm to 28 mm, a reduction of 65%.

Figure 9A:
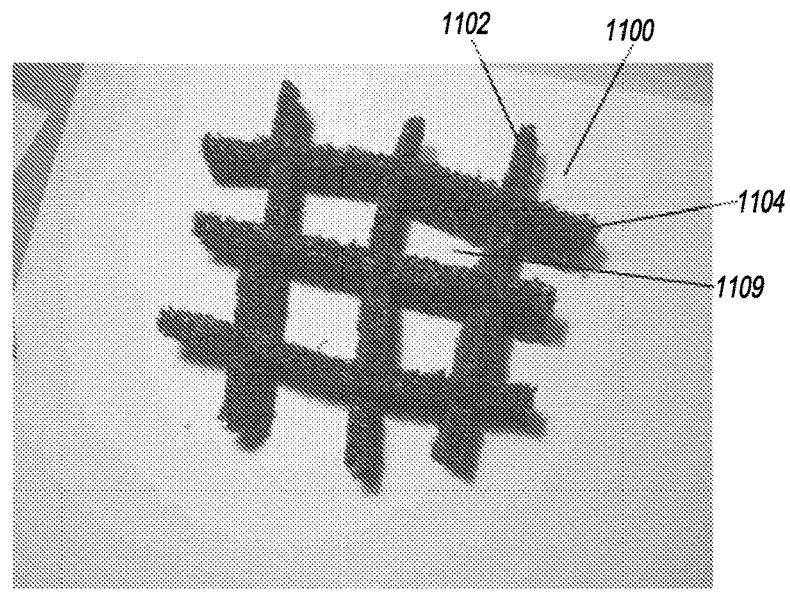
FIGS. 9A-C illustrate an embodiment of a stabilizing structure manufactured from felted foam.
Figure 9B:
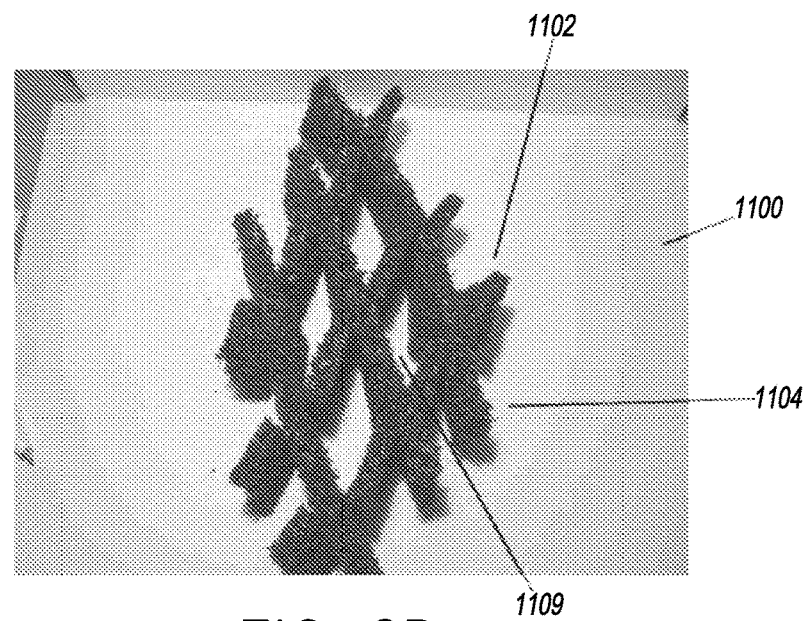
Figure 9C:
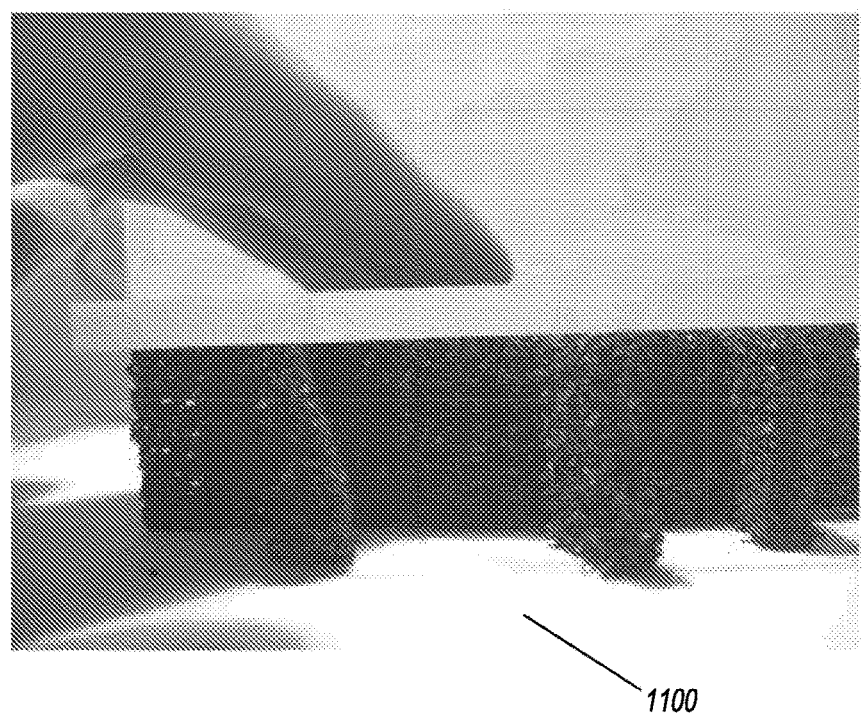

FIGS. 9A-C illustrate an embodiment of a wound closure device comprising a stabilizing structure 1100 similar to that described above in relation to FIGS. 8A-E. Here, the stabilizing structure 1100 is constructed from interlocking strips constructed from felted foam. The physical relationship between and the mechanism for the interlocking top and bottom strips 1102 and 1104 are substantially similar to what was discussed previously above, and will not be repeated here. Felted foam, however, is foam (e.g., polyurethane foam) that has been heated and compressed. After this procedure, the foam will be stiffer and less compressible, while still remaining porous. Such a material may be advantageously used in a stabilizing structure 1100 used for a wound closure device, as the material may be compressible in a plane defined by the top and bottom strips 1102, 1104, as shown in FIG. 9B. However, the material is substantially rigid in the vertical direction, as illustrated in FIG. 9C, where a weight has been placed over the foam without substantial buckling. Here, the foam can support approximately 6 kg of weight, and embodiments of the device have been measured to support at least 3 psi of applied pressure without collapse. Further, while such material is substantially rigid, the porous nature of the material permits negative pressure to be transmitted to the wound and for wound exudate to be removed.

Figure 10A:
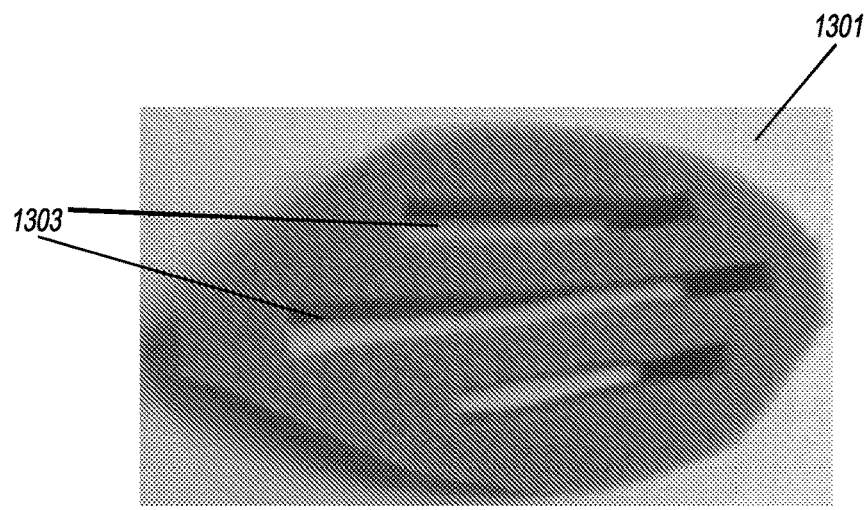
FIGS. 10A-B are photographs of further embodiments of wound closure devices comprising a porous wound filler material.
Figure 10B:
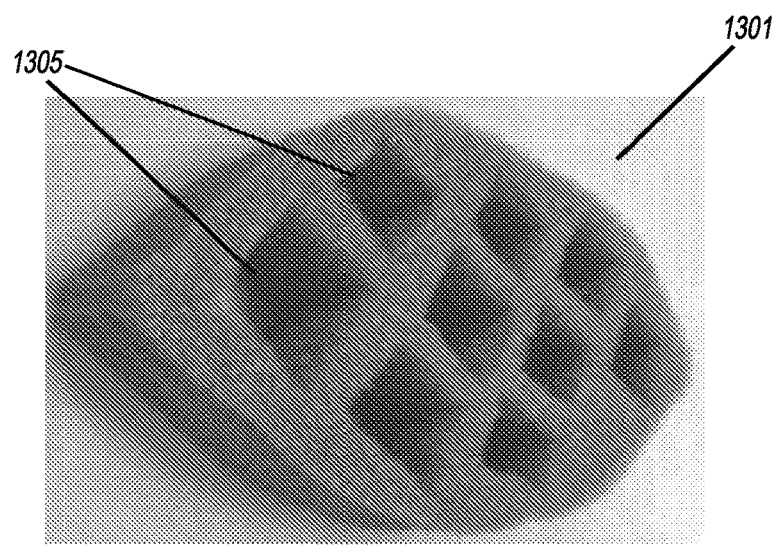

FIGS. 10A-B are photographs of further embodiments of wound closure devices. FIG. 10A illustrates an embodiment of a wound closure device 1301 that preferentially collapses along one direction. Here, the wound closure device 1301 comprises a porous wound filler material (e.g., foam) into which one or more slots 1303 have been cut. These slots 1303 preferably extend longitudinally through the thickness of the wound closure device 1301. Accordingly, the empty space will permit the wound closure device to preferentially collapse in a direction when a force is applied in a direction perpendicular to the slots 1303. Because the empty space is easier to compress than the remainder of the foam, the width and thickness of the foam will preferably not (or minimally) compress compared to the resulting compression perpendicular to the length of the wound closure device 1301.

As illustrated in FIG. 10B, the wound closure device 1301 may also be provided with holes or cells 1305 in other configurations, such as diamond-shaped holes forming a lattice. This configuration permits compression along the length and width of the wound closure device due to the compressible holes 1305, while the comparatively more rigid thickness of the foam resists compression to a greater extent.

In some embodiments, stabilizing structures similar to those illustrated above in FIGS. 8A-E may be constructed as a single unit, for example by molding, rather than from multiple parts. As with the previously-described embodiments, the stabilizing structures are configured to form an array of one or more cells defined by one or more walls and forming a plane, with each cell having a top and bottom end with an opening extending through the top and bottom ends in a direction perpendicular to the plane. In some embodiments, the stabilizing structures may have cells that are square, diamond, oblong, oval, and/or parallelepiped, and non-limiting examples of the same are illustrated in FIGS. 11-20. While some embodiments may have cells that are all the same shape, the cells may also be tailored to be larger, smaller, or differently-shaped than other cells in the structure. The shape and size of the cells may be tailored to the desired characteristics (e.g., resilience and ease of collapse) for optimal wound closure and healing.

Construction of a single unit stabilizing structure may be advantageous in terms of ease of use and cost. For example, single unit stabilizing structures may be trimmed as necessary to fit into a wound site. The material used is preferably biocompatible, and even more preferably nonadherent to the wound site. Suitable materials are preferably chosen to be soft while remaining sufficiently strong to resist collapse in a vertical direction, and may include polymers, such as polyethylene, polypropylene, polyurethane, silicone (including siloxanes), ethyl vinyl acetate, and copolymers and blends thereof. The hardness of the material may affect the thickness of the resulting stabilizing structure, and may be selected based upon the desired thickness of the stabilizing structure components (including hinges and other joints thereof) and the ability of the stabilizing structure to resist collapse, e.g., due to the atmospheric pressure acting upon a drape placed over the stabilizing structure. Suitable durometer hardnesses of materials used range from about 30 shore to 120 shore (as measured on the Shore durometer type A scale), preferably from about 40 shore to 60 shore, and even more preferably about 42 shore. Generally, the material chosen is preferably softer (while still satisfactorily meeting other material requirements), as harder materials may provide reduced levels of closure as the hardness increases.

Figure 19:
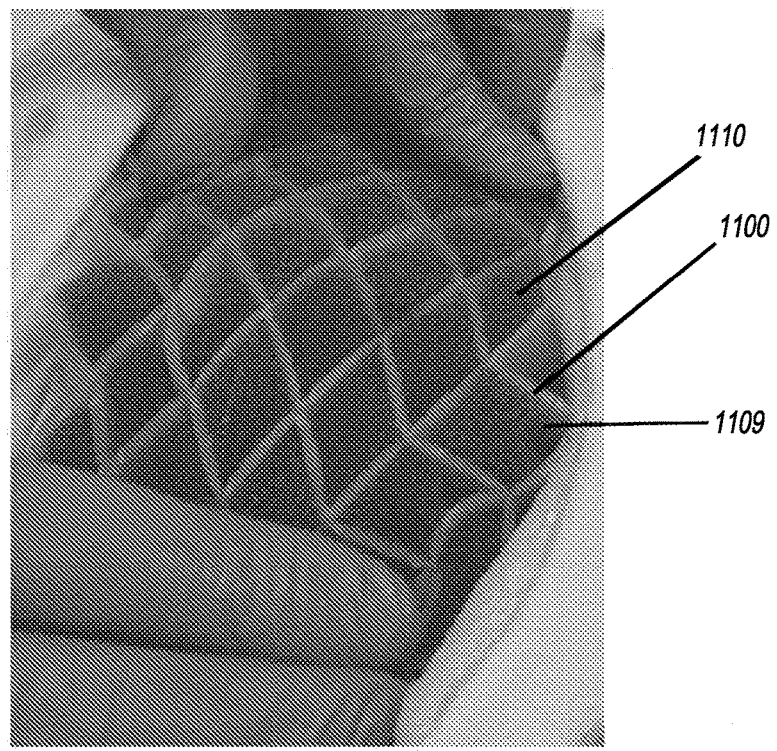
FIG. 19 is a photograph of an experiment performed to determine the efficacy of certain embodiments of wound closure devices.

FIG. 19 is a photograph of an embodiment of such device 1100 constructed as a single unit. The apertures 1109 are filled with a porous material 1110, which in some embodiments may comprise foam. Here, the device 1100 is inserted into a wound.

Figure 11A:
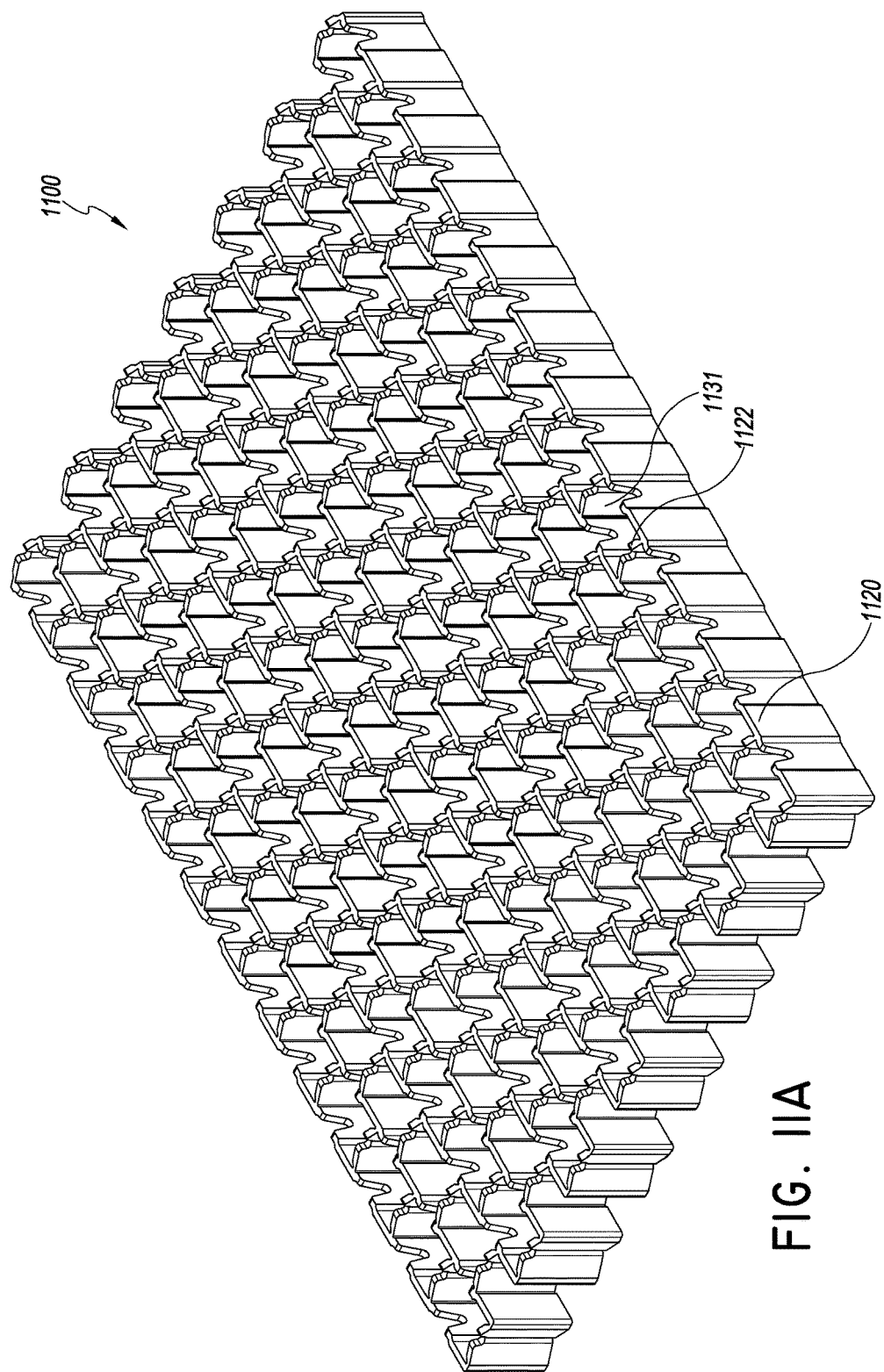
FIGS. 11A-B, 12, 13, 14, 15, and 16A-B illustrate additional embodiments of wound closure devices comprising a stabilizing structure.
Figure 11B:
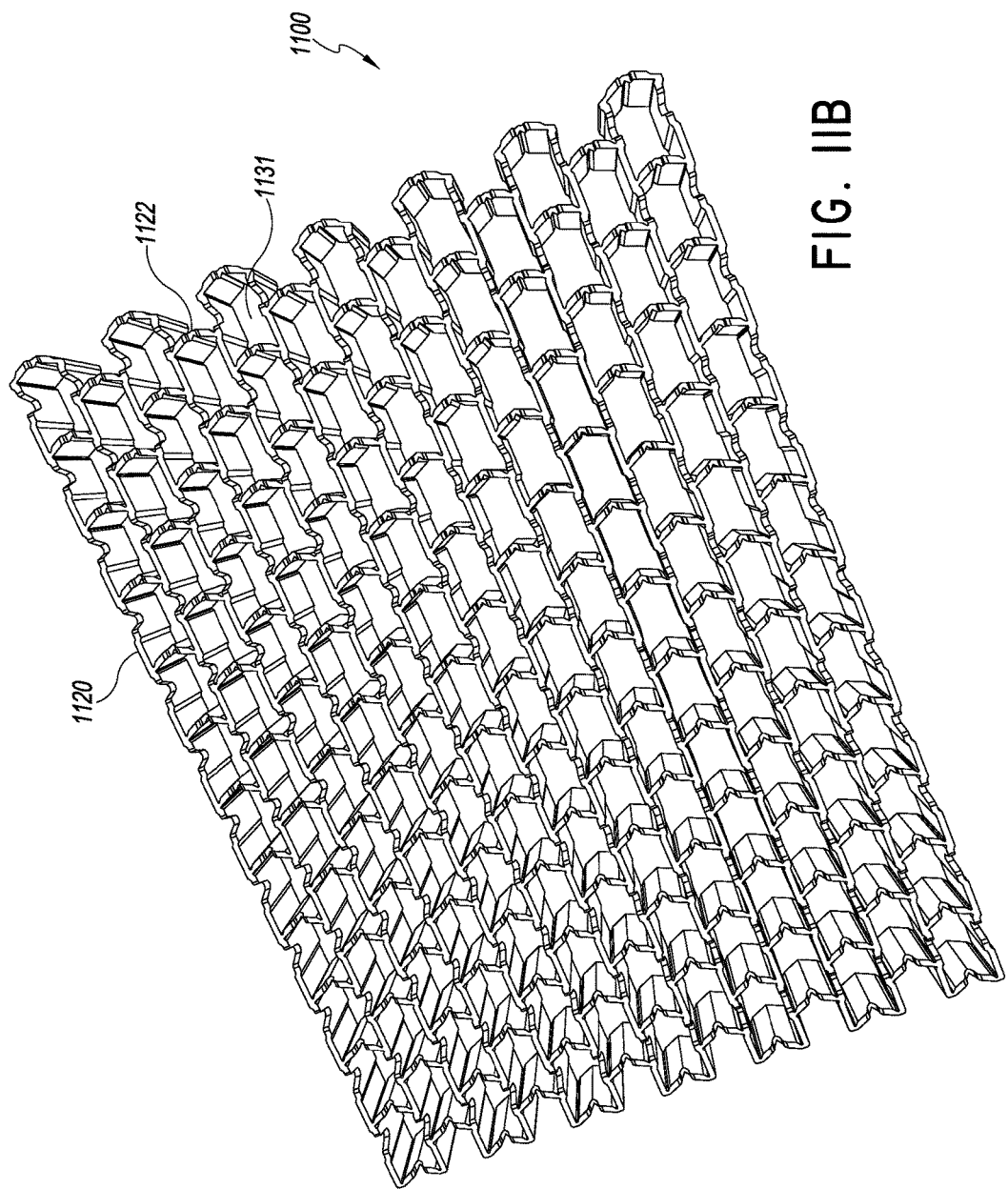

FIGS. 11A-B illustrate an embodiment of a stabilizing structure 1100 configured to preferentially collapse in only one horizontal direction while remaining substantially rigid or uncollapsed when force is applied in a vertical direction. Preferably, the stabilizing structure 1100 is constructed as a single unit as illustrated so as to form one or more cells 1131. Here, two or more longitudinal strips 1120 (which form the walls of the cells) may have relatively straight configurations, and are connected together via one or more collapsible cross strips 1122. It will be appreciated that in a single unit embodiment, the strips are merely portions of the same material that may have been formed together to form the entire single unit structure. The collapsible cross strips 1122 may be angled or indented so as to make them more likely to collapse in a direction generally parallel to their length. In this embodiment illustrated herein, the collapsible cross strip 1122 is more likely to collapse at the apex of the angled portion and at the junctions to the longitudinal strips 1120 when a force is applied in a direction approximately parallel to the general length of the collapsible cross strip 1122. In some embodiments, the collapsible cross strip is configured to fold into a portion (which may be thinner) of the longitudinal cross strip 1120.

In some configurations, one or both of the longitudinal strips 1120 and/or collapsible cross strips 1122 may comprise one or more notches positioned along a length thereof. These notches promote fluid transfer across the structure, and aid in distributing negative pressure. In some embodiments, notches may be used in conjunction with a porous material so as to enhance fluid transfer. In relation to the longitudinal strips 1120, the collapsible cross strips 1122 may be positioned alternately along the length of the longitudinal strips 1120, as best illustrated in FIG. 11B, to form a configuration somewhat analogous to a "stretcher bond" used in bricklaying. Of course, other configurations are possible. Further, although this embodiment is illustrated as being formed as a single unit, those of skill in the art will recognize that this embodiment (and the others described below) may be constructed from multiple pieces joined or connected together.

Figure 20A:
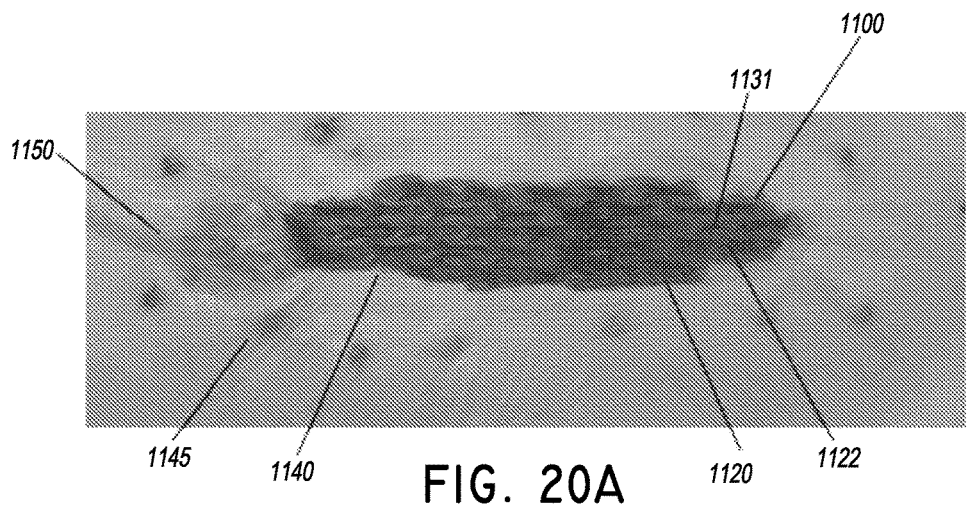
FIGS. 20A-B are photographs of experiments performed to determine the efficacy of certain embodiments of wound closure devices.
Figure 20B:
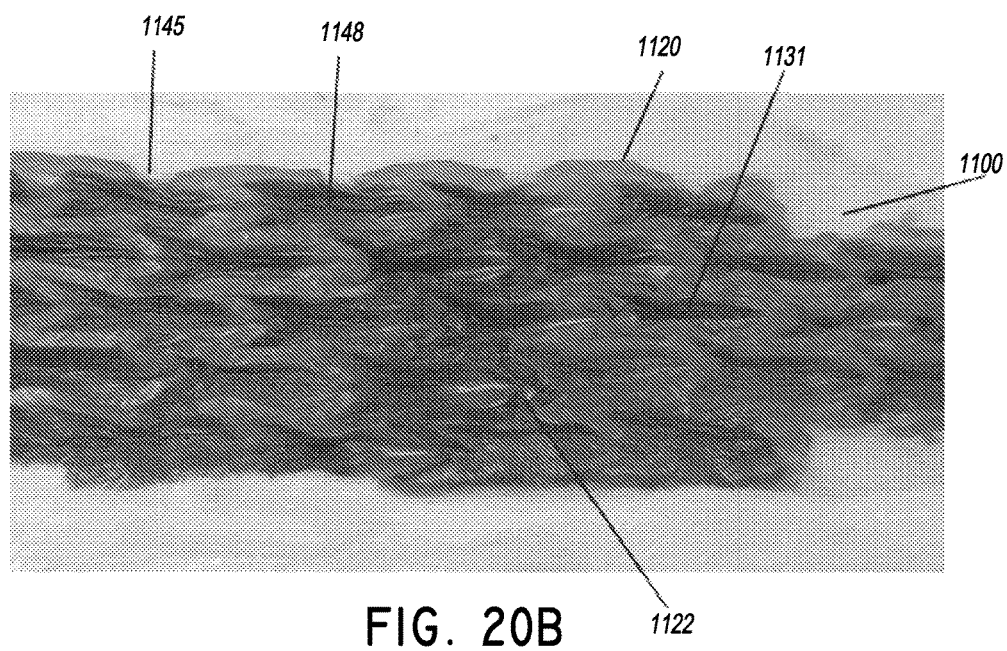

FIGS. 20A-B are photographs of an embodiment of a stabilizing structure 1100 similar to the one described above in relation to FIGS. 11A-B. Here, the structure 1100 is inserted into a wound 1140 and placed under a drape 1145. A source of negative pressure is connected via a fluidic connector 1150. FIG. 20B is a closeup view of the stabilizing structure 1100 photographed in FIG. 20A, which illustrates how the cells 1131 collapse upon the application of negative pressure while under the drape 1148. An optional porous wound filler 1148 is also illustrated.

Figure 12:
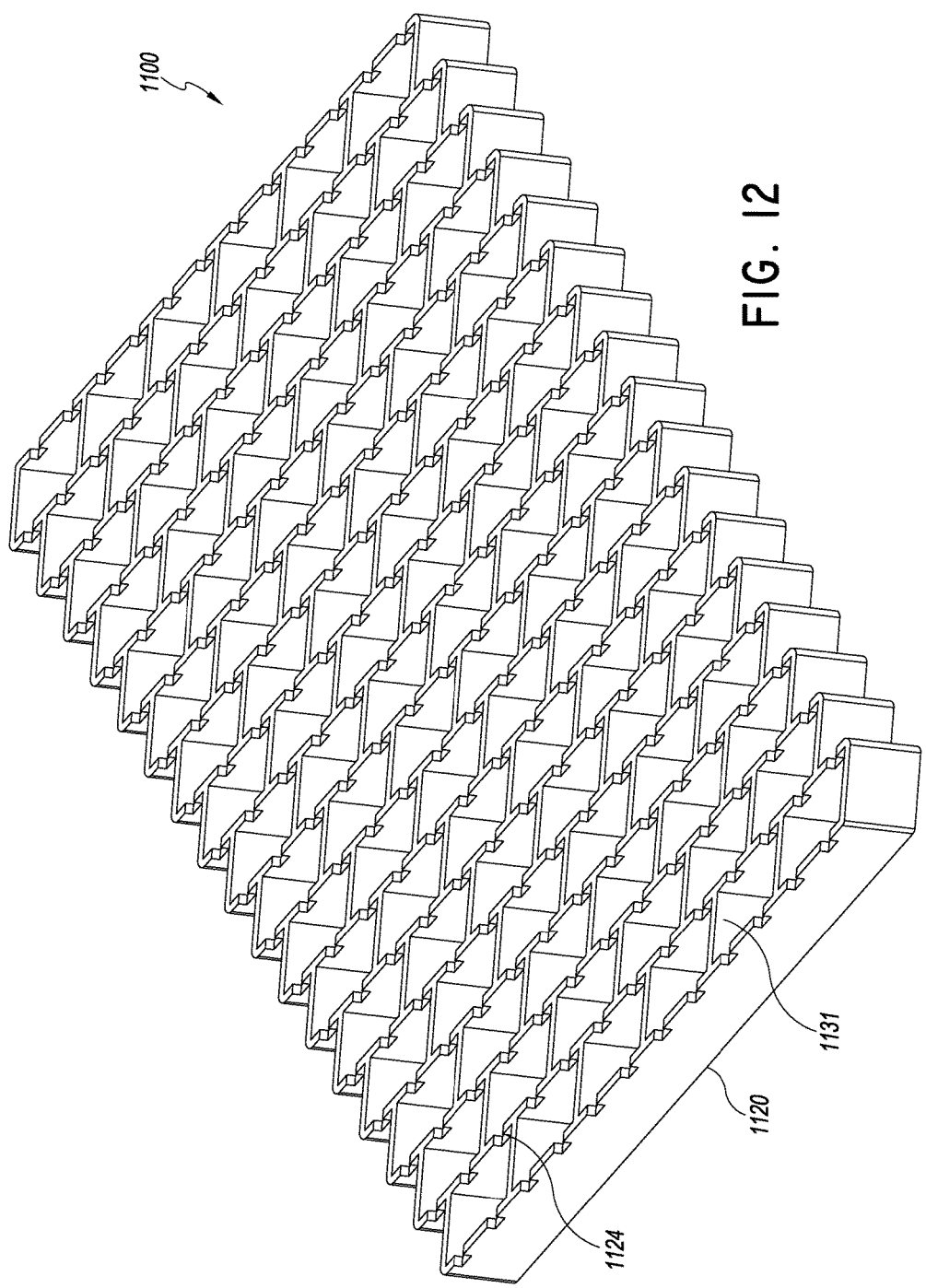

FIG. 12 illustrates another embodiment of a stabilizing structure 1100, here comprising two or more longitudinal strips 1120 attached to each other via one or more angled cross strips 1124 so as to form cells 1131. As with the embodiment illustrated in the preceding figure, the stabilizing structure 1100 is configured to collapse when pushed in a direction perpendicular to the length of the longitudinal strips 1120, while remaining substantially rigid or uncollapsed when force is applied in a vertical direction. The angled cross strips 1124 are preferably attached to the longitudinal strips 1120 so as to form a non-perpendicular angle so as to promote collapse of the stabilizing structure 1100 in the direction perpendicular to the length of the longitudinal strips 1120. As with FIGS. 8A-B, one or more notches may be formed on either or both of the longitudinal strips 1120 and/or angled cross strips 1124.

Figure 13:
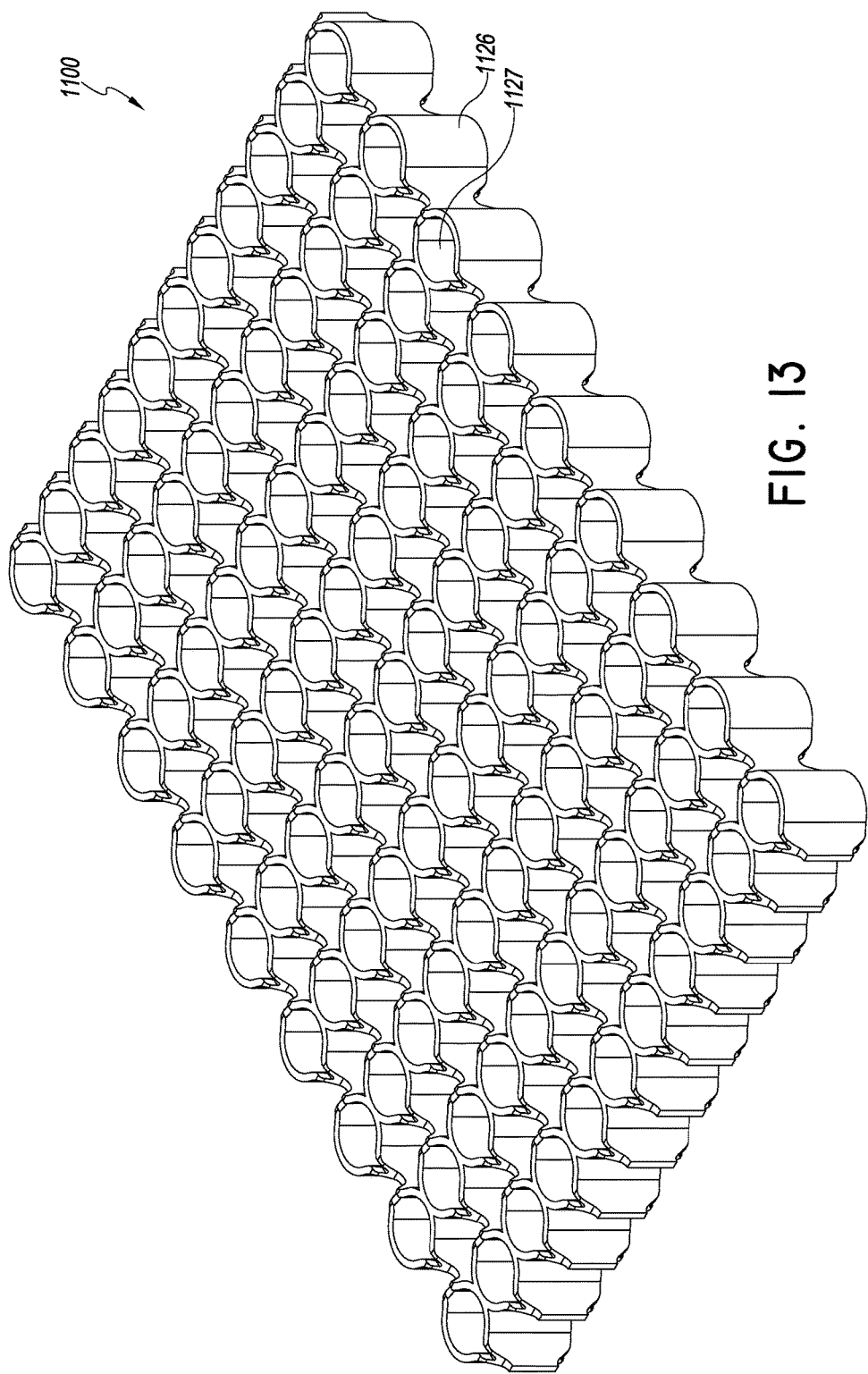

FIG. 13 illustrates a single unit stabilizing structure 1100 comprising one or more pairs of curved longitudinal strips 1126. Each individual longitudinal strip 1126 may be formed as a "wavy" strip (when seen from a vertical orientation) that, when joined face-to-face, form a one or more circular or ovoid cells 1127. As with the other stabilizing structures illustrated herein, this structure 1100 is configured to preferably collapse along a horizontal plane or direction while remaining substantially rigid or uncollapsed when force is applied in a vertical direction. Although the structure 1100 is illustrated here as being formed from a single unit, the structure may be constructed from two or more curved longitudinal strips 1126 welded or attached together at the points shown. As with several other embodiments described herein, one or more notches may be made onto the walls so as to aid in fluid transfer across and through the structure 1100.

Figure 14:
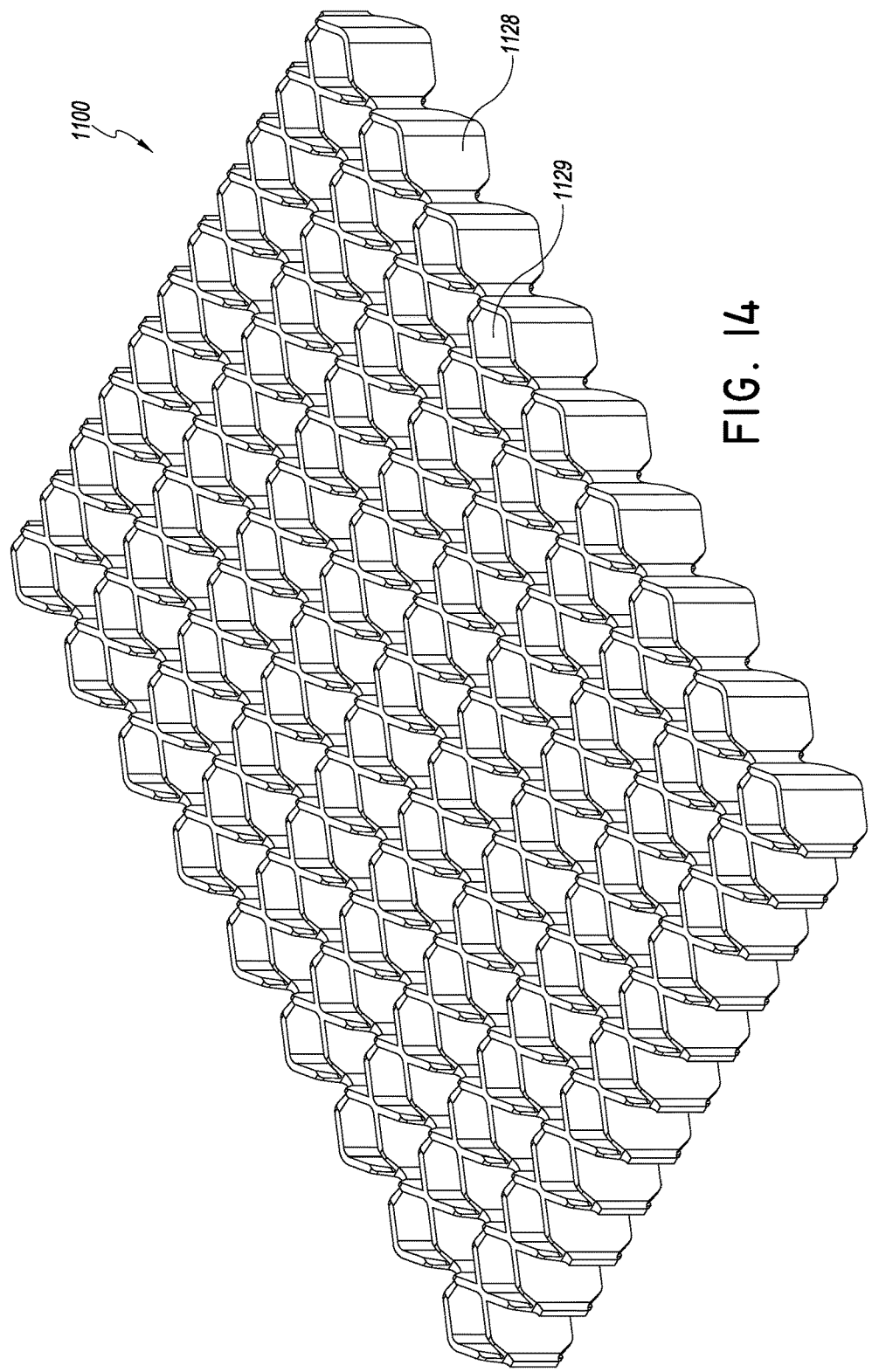

FIG. 14 illustrates a stabilizing structure 1100 similar to the one illustrated in FIG. 13. Here, however, zigzag longitudinal strips 1128 are joined to form diamond-shaped (rather than circular or ovoid) cells 1129. It will be of course appreciated that this embodiment may also be manufactured using substantially straight strips in a style similar to the embodiments illustrated in FIGS. 8A-D.

Figure 15:
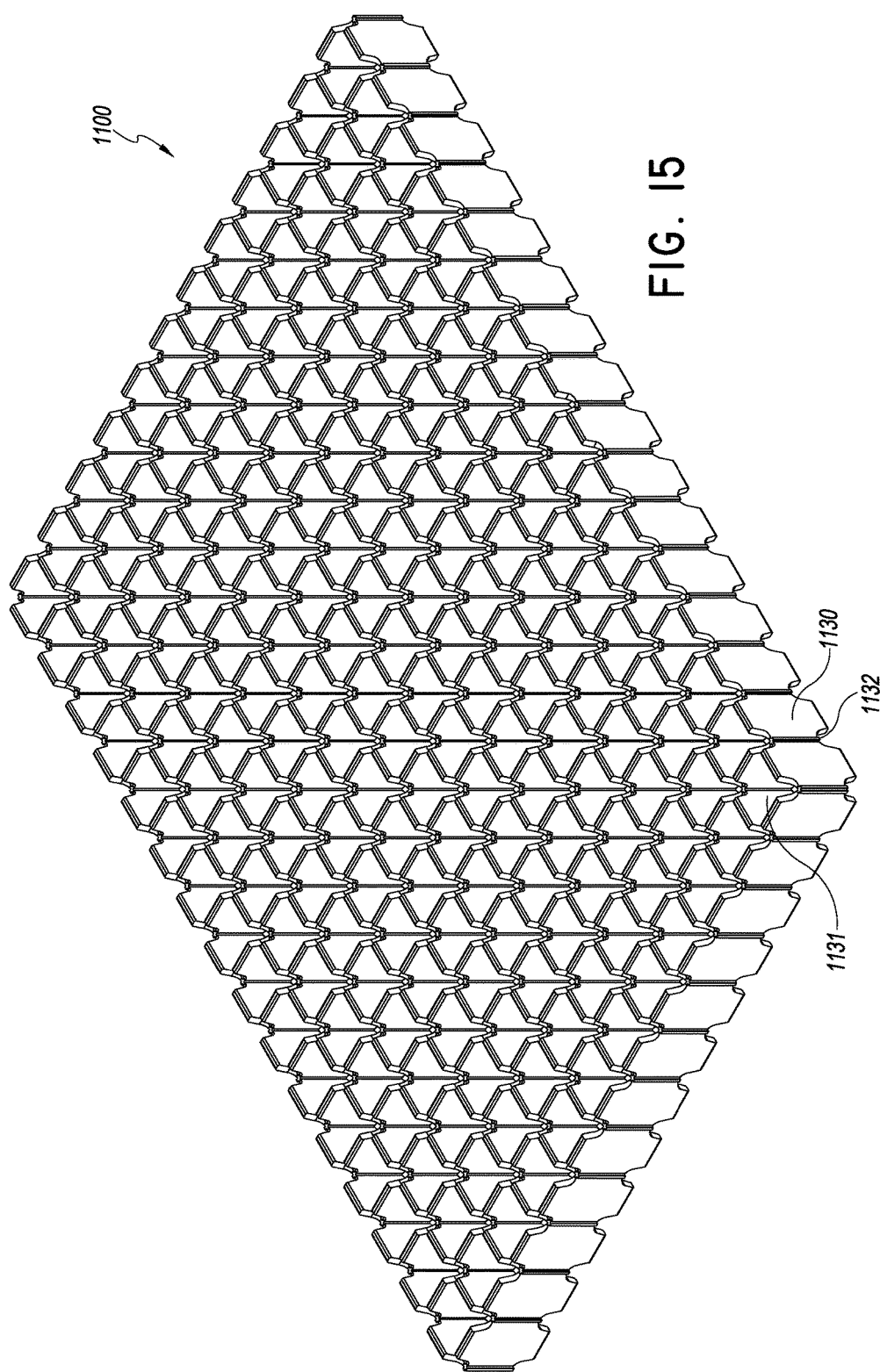

FIG. 15 illustrates a stabilizing structure 1100 comprising vertical segments 1130 joined together at approximately perpendicular angles so as to form quadrilateral or square cells 1131. Preferably, the vertical segments 1130 are of a square or rectangular shape, with tapers 1132 that join the segments together in a movable and flexible configuration. As with the other embodiments described herein, this stabilizing structure 1100 may be manufactured as a single unit, and is preferably configured to collapse in a horizontal plane or direction while remaining substantially uncollapsed in a vertical direction.

Figure 16A:
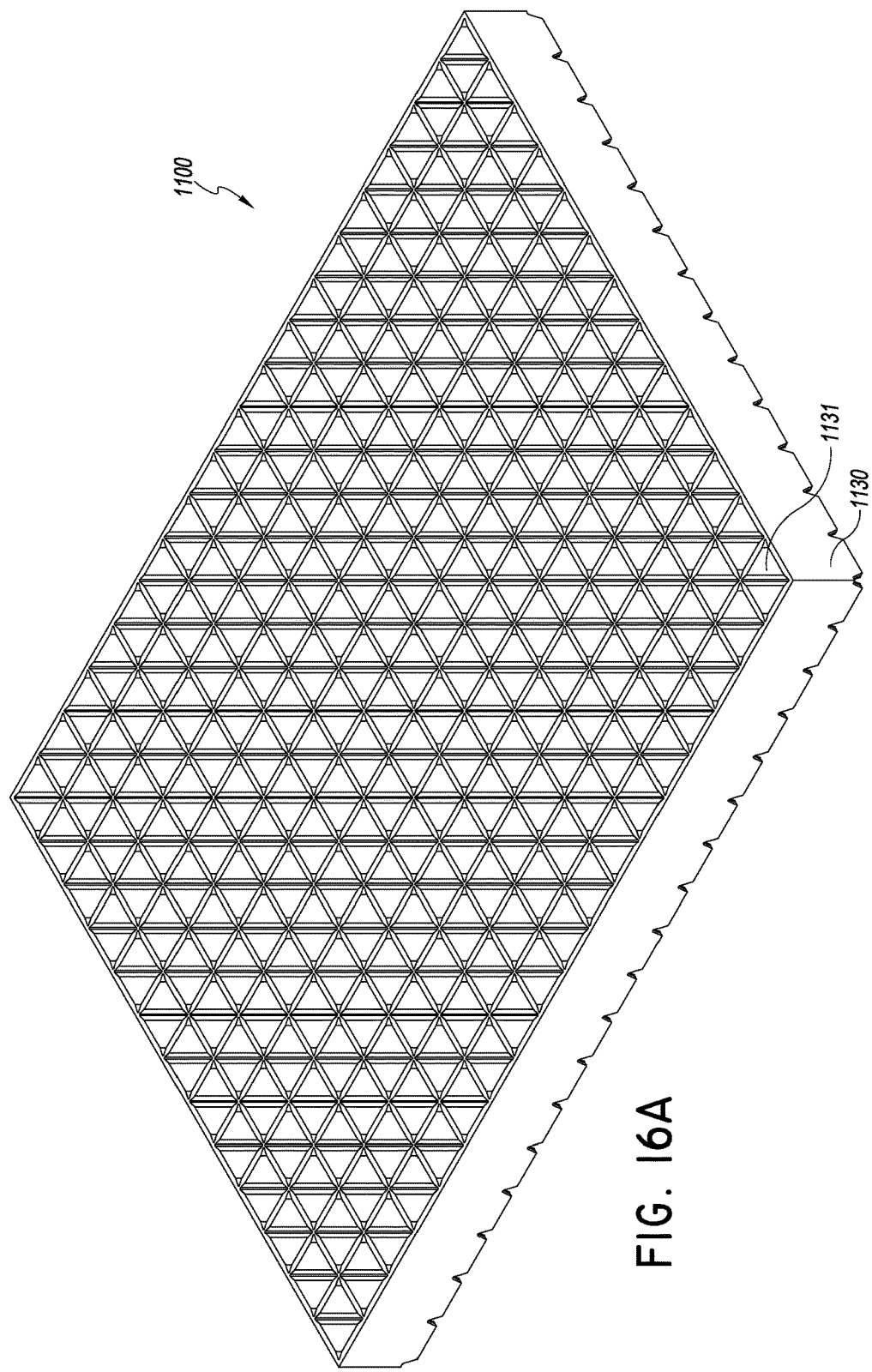
Figure 16B:
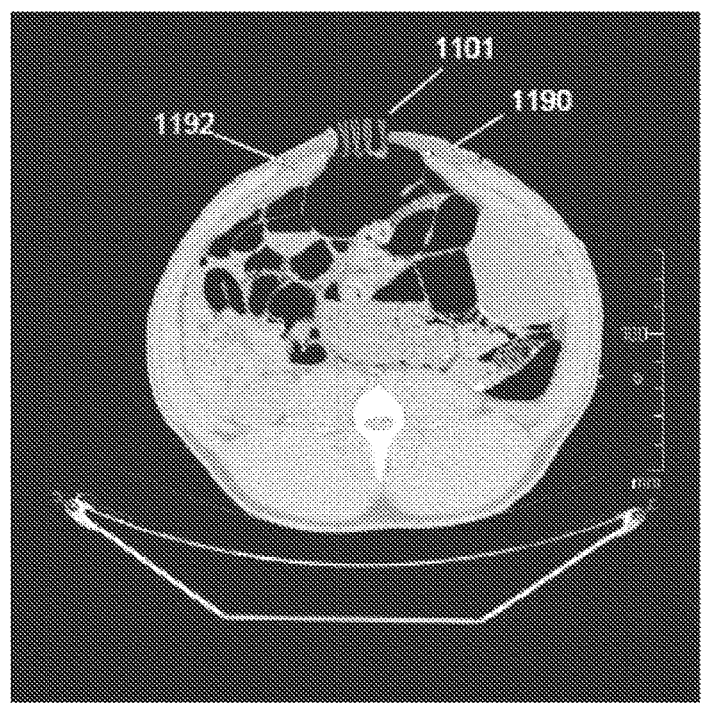
Figure 17:
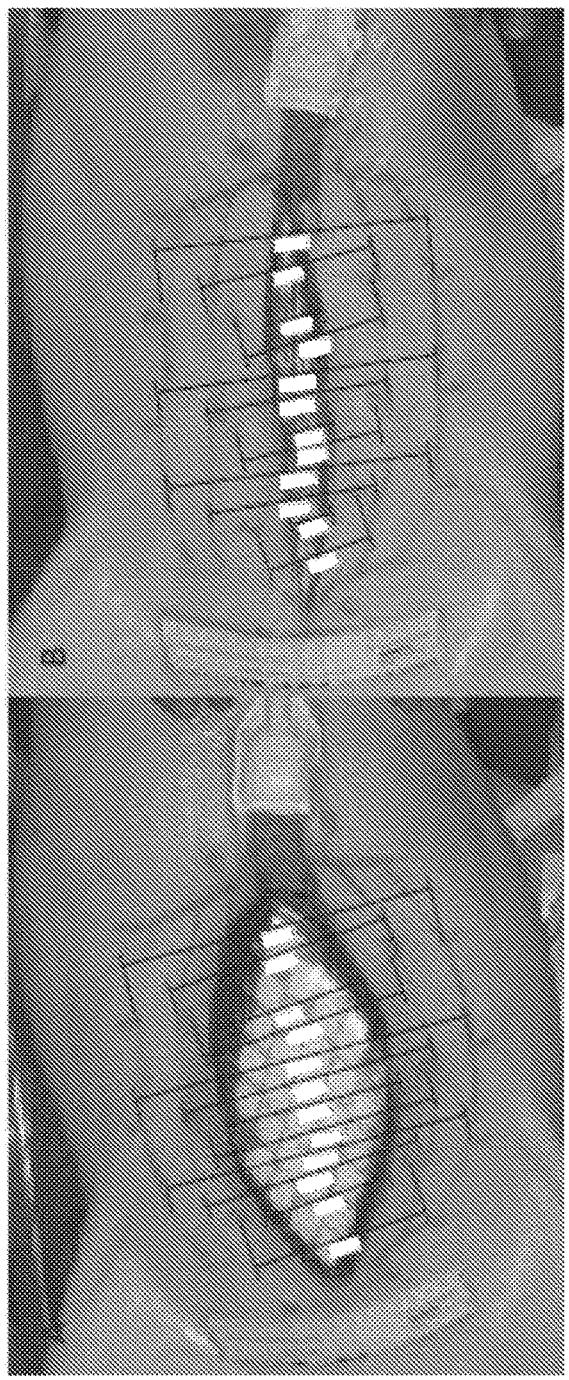
FIGS. 17A-B, 18A-B are before and after photographs of experiments performed to determine the efficacy of certain embodiments of wound closure devices.
Figure 18:
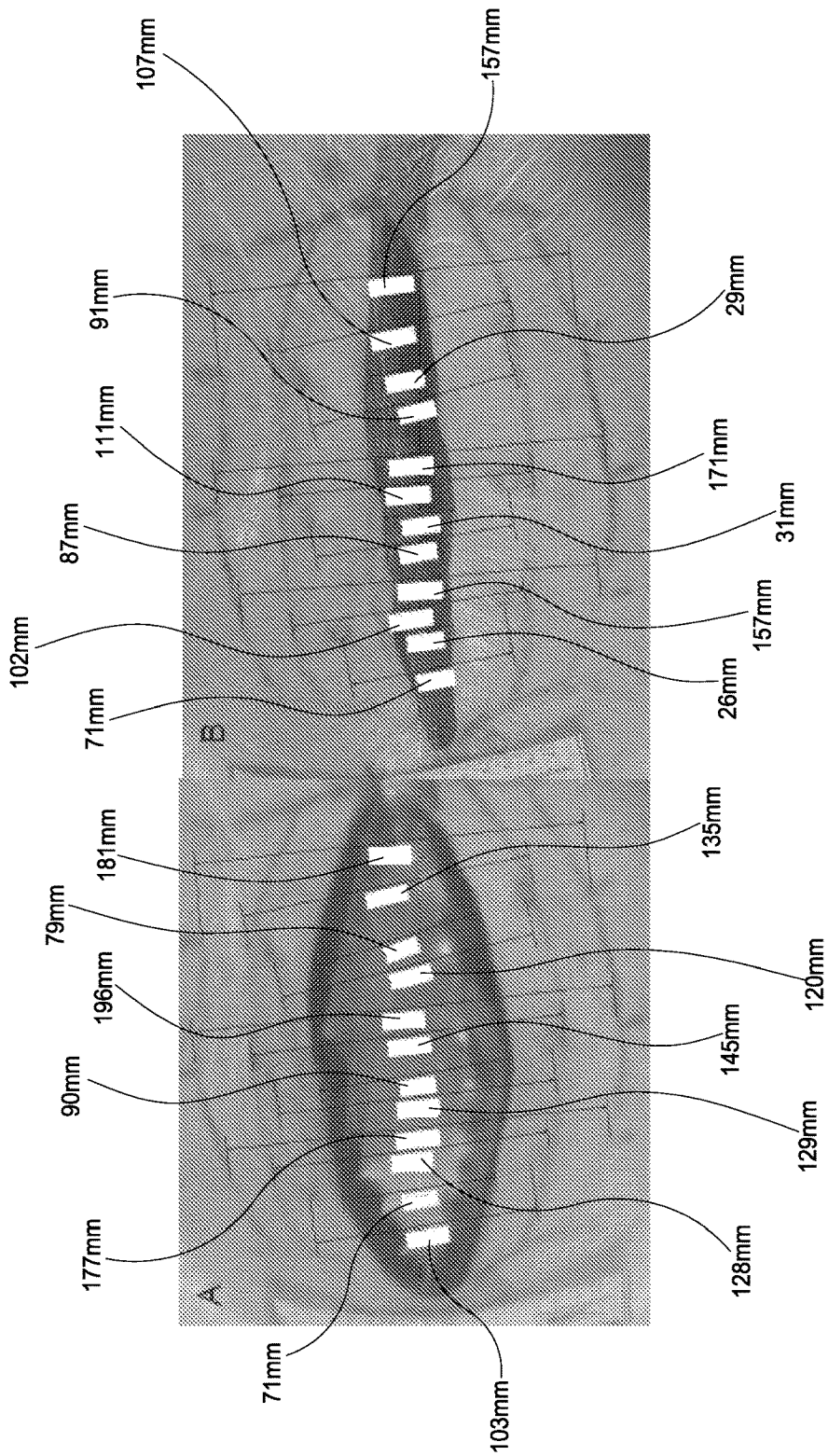

FIG. 16A-B illustrates another stabilizing structure 1100 similar to the embodiment illustrated above in FIG. 15. The vertical segments 1130 are preferably joined together so as to form one or more quadrilateral or square cells 1131. Here, however, the vertical segments 1130 do not comprise a tapered portion 1132. However, one or more notches may be present on the underside (wound-facing side) of the structure 1100, and which function as described in preceding embodiments. Although this embodiment may be manufactured from multiple vertical segments 1130, it is preferably molded as a single unit.

FIG. 16B illustrates a CT image of an embodiment of a stabilizing structure 1100 as described above in relation to FIG. 16A, and which has been inserted into an abdominal wound. Subcutaneous fat layers 1190 are bilateral and present over muscle tissue layer 1192. Upon application of negative pressure (as illustrated), improved fascial reapproximation and wound closure may be observed. Here, the width of the wound along the view illustrated reduced from approximately 82 mm to 52 mm, a reduction of 37%.

Figure 32:
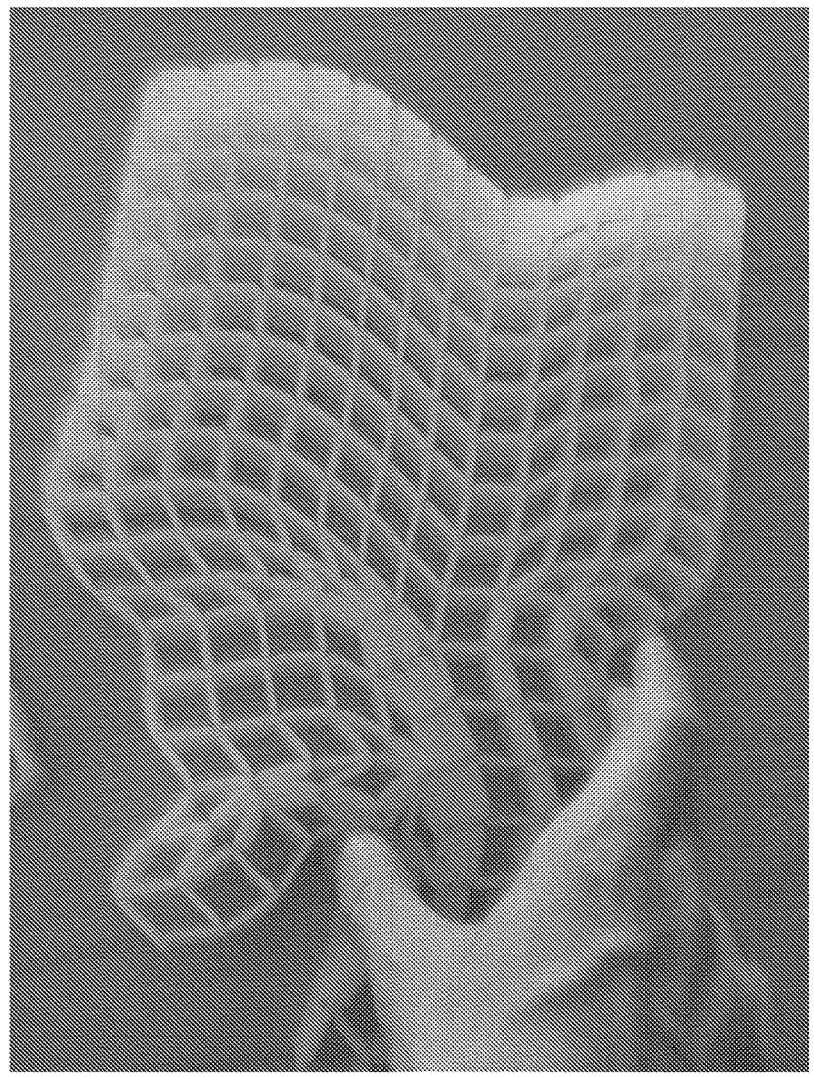
FIG. 32 illustrates an embodiment of a fully flexible stabilizing structure.

FIG. 32 illustrates an embodiment of a stabilizing structure similar to the structures described in FIGS. 11-16A. In this embodiment, the longitudinal strips and cross strips are formed from a single piece of material and form rows of flexible cells that are configured to collapse in a horizontal plane. Because each of the longitudinal and cross strips are formed from the same flexible material, applying a lateral force to the structure causes the cells to collapse generally independently of each other. In other words, the collapse of one or more cells in a row does not necessarily cause the collapse of other cells in the same row.

Example 5

In this next non-limiting experiment, the wound described in the preceding examples had an embodiment of the stabilizing structure device described above in relation to FIGS. 8A-E inserted into the abdominal cavity. In this experiment, and as illustrated in FIG. 17A, white foam inserts were placed into the quadrilateral openings of the stabilizing structure, and the outer edges (in contact with the wound) were wrapped in black foam. The wound and stabilizing structure were then sealed with a drape and connected to a source of negative pressure as described previously.

Wound area measurements were taken before and after activation of the negative pressure source. Here, the size of the wound before application of negative pressure was measured as 171 mm$^2$. Upon the application of negative pressure, as illustrated in FIG. 17B, the area of the wound was greatly reduced to 55 mm$^2$, a reduction of 68%. It is noted that here and in the following examples, as the wound area contracts along its width, the length of the wound increases slightly, indicating that the tissue margins are returning to their original anatomical position.

Example 6

FIGS. 18A-B illustrate the results of a non-limiting experiment similar to those illustrated above, where a stabilizing structure similar to the embodiments of FIGS. 8A-E was inserted into the abdominal cavity. Here, the spaces in the quadrilateral openings of the stabilizing structure were empty, and a layer of foam was wrapped around the outer edges of the structure.

Wound area measurements before and after application of negative pressure indicated that the wound area decreased by 63%, from 155 mm$^2$ to 58 mm$^2$.

Without wishing to be bound by theory, the greater reduction in wound area in the preceding examples, as compared to the black foam control of Example 1, is believed to be due to the fact that the wound devices used therein do not significantly compress in a vertical direction when negative pressure is applied. This is different from traditional foam dressings, where the application of negative pressure causes downward pressure on the foam due to the air pressure pressing onto the drape, which is then transmitted along the foam dressing into a horizontal force that pushes the wound margins outward. With the use of a stabilizing structure as used in the various examples illustrated here, the foam and other dressing components are not pushed outward, and thus the wound margins may be approximated more easily so as to achieve faster wound closure. In fact, in some experiments, certain embodiments of the wound devices projected upward over the wound margins, and these vertical surfaces may therefore allow for atmospheric pressure to produce contractile forces onto the devices and/or the wound margins.

Traditional negative pressure wound treatment typically uses foam (or other porous materials) placed into a wound underneath a drape, to which negative pressure is applied to the wound. In such situations, the application of negative pressure may cause downward pressure on the foam due to the air pressure pressing onto the drape, which is then transmitted along the foam dressing into a horizontal force that pushes the wound margins outward. Without wishing to be bound by theory, it is believed that some of the embodiments of stabilizing structures, wound closure devices, and wound treatment devices, methods, and systems described below are able to cause a greater reduction in wound area as compared to traditional negative pressure treatment. One of these factors is believed to be because embodiments of the stabilizing structures and wound closure devices described herein do not significantly compress in a vertical direction when negative pressure is applied. With the use of certain embodiments described herein, foam and other dressing components are not pushed outward due to negative pressure, and thus the wound margins may be approximated more easily so as to achieve faster wound closure and better wound healing.

Stabilizing Structures and Wound Closure Devices of FIGS. 21A-27B

Figure 21A:
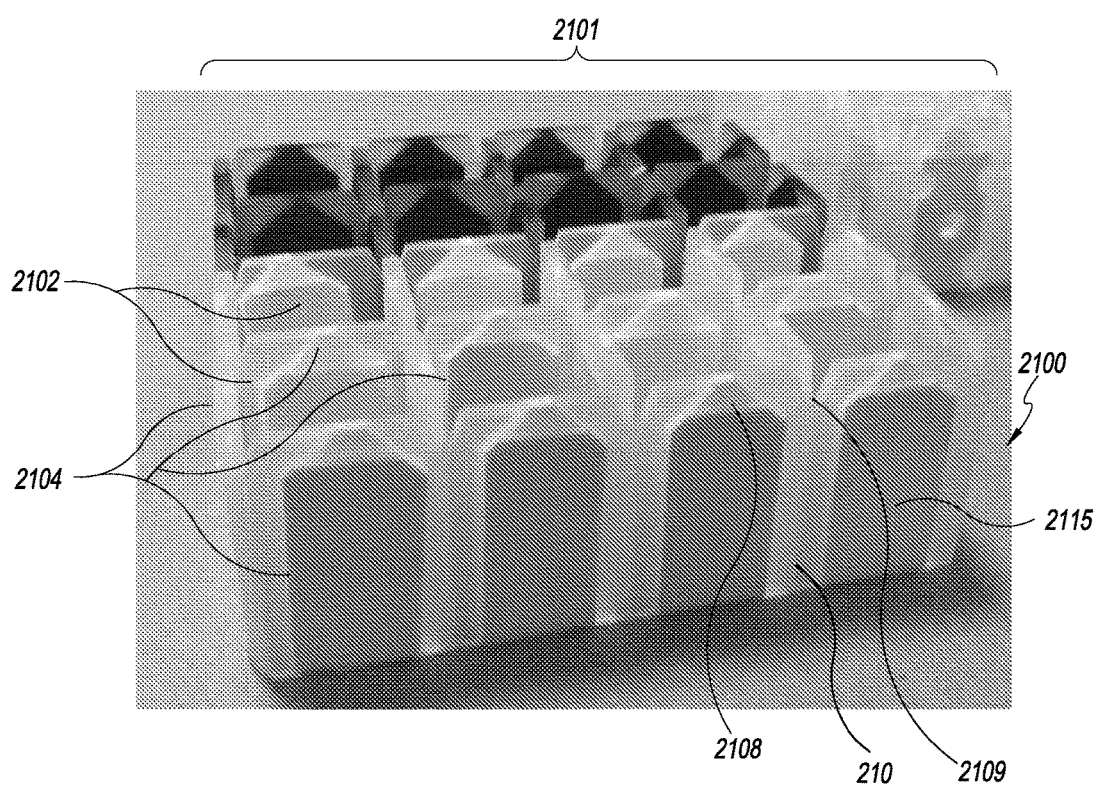

FIG. 21A is a photograph of an embodiment of a wound closure device comprising a stabilizing structure 2100 that may be placed or inserted into a wound. Here, the device comprises a plurality of cells 2102 provided side-by-side in a generally planar configuration. Preferably, the stabilizing structure 2100 is configured to collapse in a direction along a plane 2101 defined by the width of the device, without significantly collapsing in a direction perpendicular to the plane 2101. That is, when viewed in the figure, the stabilizing structure 2100 will collapse in the horizontal direction, but will not compress in the vertical direction. In some embodiments, the stabilizing structure collapses in conjunction with the movement of tissue. Here, the cells 2102 are preferably open at both ends in a direction perpendicular to the plane 2101.

Each of the cells 2102 is preferably formed with four walls 2104, each wall 2104 being joined to the next by a flexible joint 2106. The joints 2106 are preferably designed so as to be more flexible than the walls 2104, and promote collapse of the stabilizing structure 2100 in the direction of the plane. Of course, it will be understood that other configurations are possible, and in some embodiments each cell 2102 may be defined by less than or greater than four walls 2104, for example five walls or six walls, thus forming pentagonal or hexagonal cells. The cells 2102 may not necessarily be symmetric, and can form rectangular, diamond, rhomboidal, trapezoidal, parallelepiped, oblong, oval, and other such shapes in addition to the square-walled embodiment illustrated herein.

One or more of the walls 2104 defining the one or more cells 2102 may further comprise an insert 2115 disposed therein, and described in greater detail below in FIGS. 22A-F. Preferably, the insert 2115 will be constructed from a material more rigid than the material used to construct the remainder of the wall 2104. Some suitable materials may include metals such as titanium, stainless steel, and largely inert alloys (such as monel and hastelloy), and/or polymers such as polyurethane, silicone, rubber, isoprene, polyethylene, polypropylene, nylon, polyacrylate, polycarbonate, and PEEK. Some embodiments may also comprise composite materials, including resin-reinforced fiber composites where the resin may be, for example, various types of epoxies. Suitable fibers may include glass, carbon, carbon nanotubes, grapheme, and aramids (e.g., Kevlar). Preferably, the material chosen for the insert 2115 is not only sufficiently rigid, but also able to adhere to the material used in the wall 2104. For example, the insert material is preferably able to adhere to softer polymers such as silicones used in the wall 2104. The more rigid materials used in the insert 2115 may provide for additional collapse resistance in the direction perpendicular to the plane for the stabilizing structure 2100.

In some embodiments, one or more notches 2109 may be provided between multiple walls 2104, and which may further aid in permitting the flexible joints 2106 to move. Without wishing to be bound by theory, the notches 2109 may also aid in distributing negative pressure and transmitting fluid throughout the stabilizing structure 2100 when negative pressure is applied, for example in a clinical care setting. Some embodiments may also comprises holes in the walls 2104 or joints 2106, or be constructed from porous materials.

Preferably, a cavity 2108 is provided within each wall 2104 for the insert 2110 to be disposed therein. The walls 2104 may be molded around each insert 2115. An insert 2115 may also be inserted into the cavity 2108 after the wall 2104 is manufactured. While the embodiment illustrated here and in the subsequent images shows a single insert 2115 in each wall 2104, some embodiments may be provided with one or more inserts 2115 disposed therein.

Figure 21B:
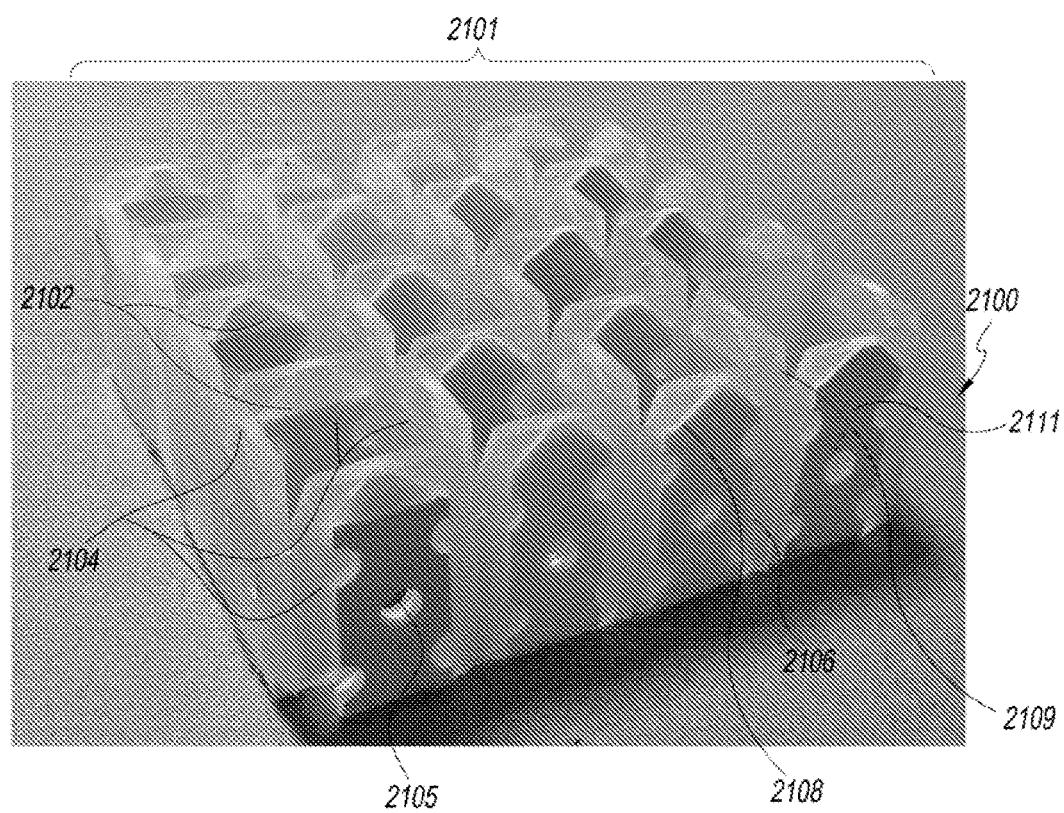

FIG. 21B illustrates an embodiment of a stabilizing structure 2100 with many similar features to FIG. 21A. Here, an insert 2111 comprises structural differences compared to the insert 2110, and is discussed in more detail below in relation to FIG. 22E. When inserted or placed within the cavity 2108, one or more of the walls 2104 may comprise a hole 2105 communicating through at least one aperture in the insert 2111. In addition to any notches 2109, the one or more holes 2105 may permit additional displacement of wound exudate and distribution of negative pressure within the stabilizing structure 2100.

Figure 21C:
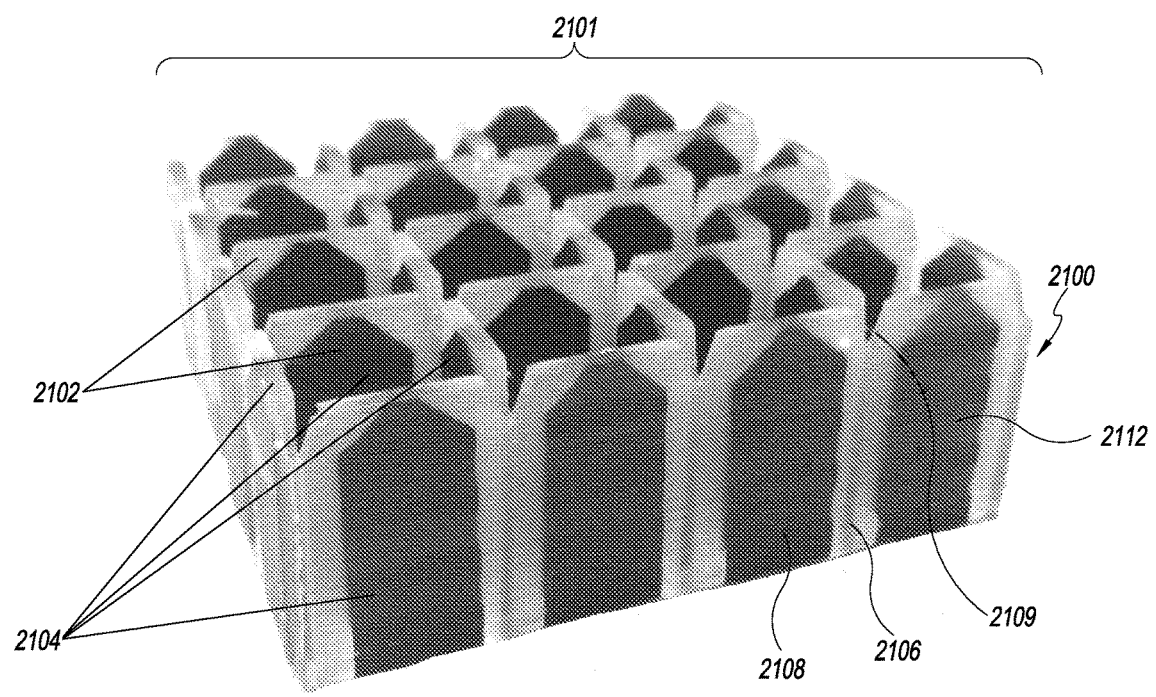

FIG. 21C illustrates an embodiment of a stabilizing structure 2100 with similar features as the other embodiments described previously. In this embodiment, the stabilizing structure 2100 comprises an insert 2112 described in greater detail below in FIG. 22F.

Figure 21D:
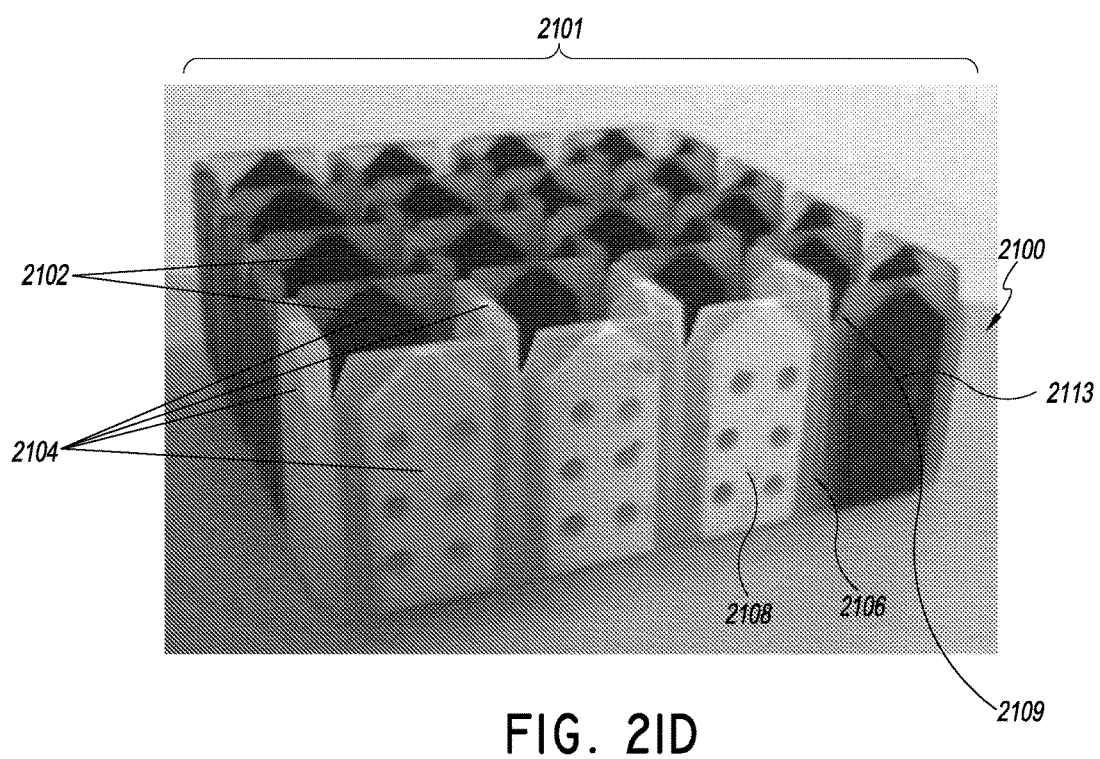
Figure 2I:
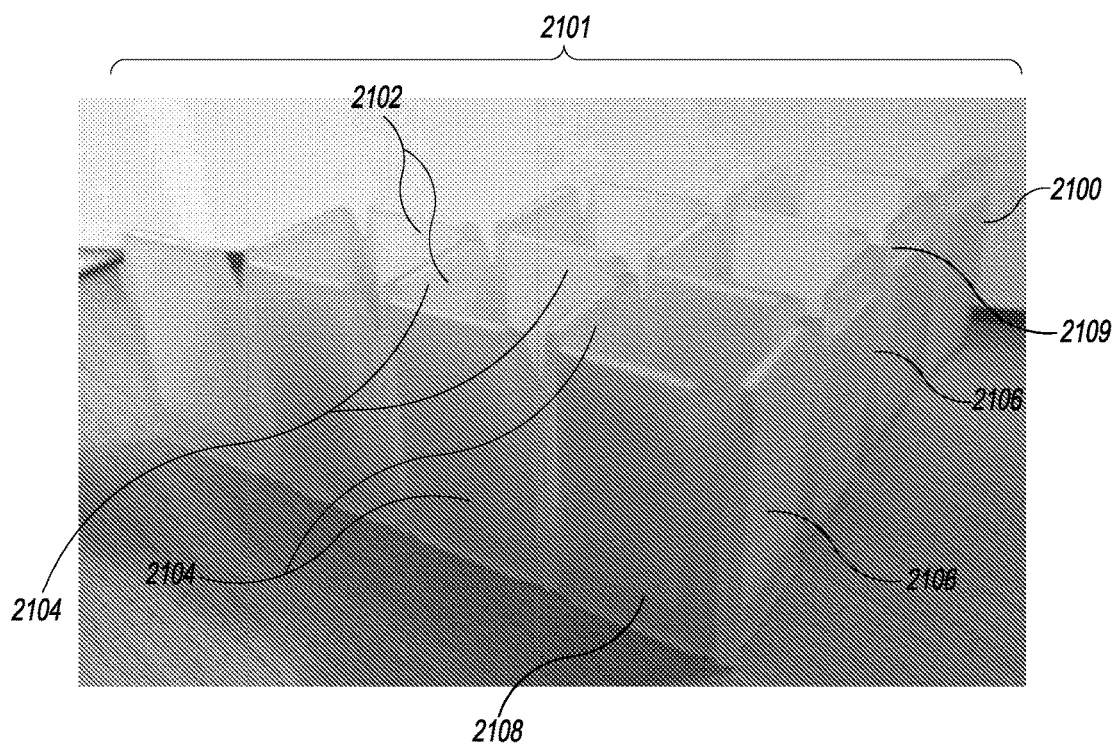

Similarly, FIG. 21D illustrates an embodiment of a stabilizing structure 2100 comprising an insert 2113 described in greater detail below in FIG. 22D. FIG. 21E illustrates an embodiment of a stabilizing structure 2100 comprising an insert 2114 described in greater detail in relation to FIG. 22A.

In the preceding embodiments of stabilizing structures 2100 comprising various inserts 2110, 2111, 2112, 2113, and 2114, it will of course be understood that embodiments of the stabilizing structure 2100 does not need to contain only one type of insert. Likewise, each cell 2102 or wall 2104 may comprise one or more different types of inserts, or no inserts at all. Varying the different inserts and other properties of the cells 2102 and walls 2104 may thus permit the stabilizing structure 2100 to be tailored to the appropriate wound type so as to effect optimal wound closure and/or treatment.

FIGS. 22A-F illustrate examples of different inserts that may be used as part of a stabilizing structure 2100. Preferably, these inserts may be placed, molded into, or formed as part of a wall 2104 in a stabilizing structure 2100 (e.g., of the types illustrated above in FIG. 21A-E). Various modifications may be made, as described below, that may improve or alter characteristics of the inserts.

Turning now to FIG. 22A, the embodiment of the insert 2114 illustrated here is approximately rectangular in shape, and is adapted to be inserted or formed into one or more of the walls 2104 of an embodiment of the stabilizing structure 2100. In some embodiments, one or more of the inserts 2114 may have a height greater than the width, and the wall 2104 may have a height between 20 mm and 30 mm, preferably 25 mm, and a width between 8 mm and 14 mm, preferably 10.8 mm. The insert 2114 is preferably thin but with enough structural strength to resist collapse, and in some embodiments, measuring between 0.5 mm and 4 mm in thickness, preferably 1-2 mm. These measurements may be appropriate for the other inserts discussed below as well.

FIG. 22B illustrates an embodiment of the insert 2110 with a generally rectangular configuration, but provided with two notches 2201 cut diagonally across a top end of the insert 2100. The notches 2201 may facilitate clearance of the insert 2100 from any notches 2109 that may be provided in the walls 2104. Further, the notches 2201 may also aid in the insertion of the insert 2100 into the cavity 2108 of the wall 2104. The notches 2201 may also be helpful in conjunction with the notches 2109 in further defining a channel or other opening for fluid to be transmitted or transferred between and through each cell 2102. The notches 2201 may also aid in ensuring that the entire stabilizing structure is able to more easily collapse.

FIG. 22C illustrates an embodiment of an insert 2115 provided with two notches 2201 as well as a horizontal lip 2203. The horizontal lip 2203 may aid in inserting the insert 2115 into the cavity 2108 of the wall 2104, or may aid in fixing the wall 2104 around the insert 2115 when the wall is molded around it. The horizontal lip 2203 may be beneficial in effectively reducing the bulk of the insert at one end of the wall 2104, and in conjunction with a softer material used in the wall 2104, may thereby increase comfort due to the correspondingly greater amount of wall material. In some embodiments, the horizontal lip 2203 and/or notches 2201 may be present on both ends of the insert 2115 or other inserts described herein. In some embodiments, the horizontal lip 2203 is approximately half the thickness of the overall insert 2115. For example, the insert 2115 may be between 0.5 mm and 4 mm in thickness, preferably 2 mm. If the insert 2115 measures 2 mm in thickness, the thickness of horizontal lip 2203 may be 1 mm.

FIG. 22D illustrates an embodiment of the insert 2113, and which is similar to the embodiment used in the stabilizing structure 2100 illustrated in FIG. 21D. This insert 2113 may comprise one or more apertures 2205, which in some embodiments may communicate with one or more holes 2105 that may be formed through one or more walls 2104. In some embodiments, the apertures 2205 are arranged in a 2×3 pattern illustrated here, although other arrangements are possible. Notches 2201 may also be present.

Figure 22F:
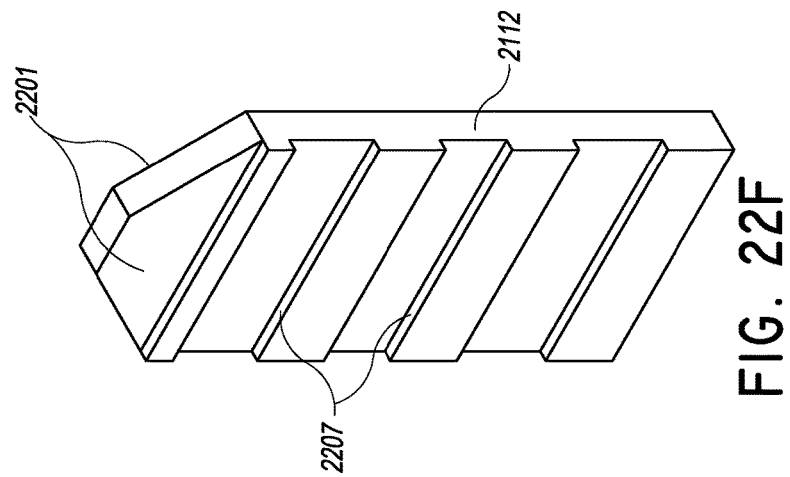
Figure 22E:
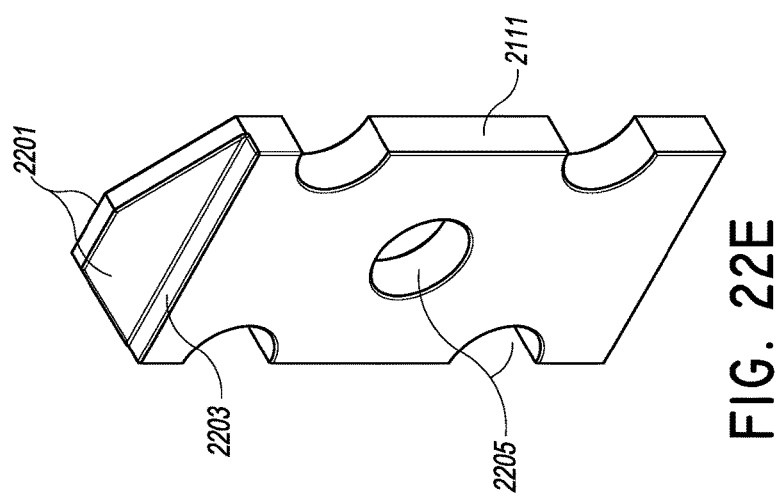

FIG. 22E illustrates an embodiment of the insert 2111, which is similar to the embodiment used in the stabilizing structure 2100 illustrated in FIG. 21B. The insert 2111 preferably comprises two notches 2201. A horizontal lip 2203 may also be provided. Preferably, one or more apertures 2205 may be formed therein. In some embodiments, one or more of the apertures 2205 may extend to the edge of the insert 2111 as illustrated. In some embodiments, the apertures 2205 may be configured to have four apertures arranged around a central aperture, although other configurations are of course possible. In some embodiments, the reduced amount of insert material at the locations of the apertures may be advantageous to provide a greater amount of softer wall material at a hinge point, where this may consequently increase flexibility. In a preferred embodiment, the insert 2111 has a height of 25 mm and a width of 10.8 mm, with a thickness of 2 mm. The first set of apertures may be centered approximately 5 mm from the bottom edge of the insert 2111, the central aperture may then be centered approximately 11 mm from the bottom, and the top set of apertures may be centered 17 mm from the bottom.

FIG. 22F illustrates an embodiment of the insert 2112, which shares some similarities to the embodiment used in the stabilizing structure 2100 illustrated above in FIG. 21C. The insert 2112 preferably may comprise one or more channels 2207 formed therein. Preferably, the one or more channels 2207 are disposed in a horizontal configuration across the width of the insert 2112. While the insert 2112 is preferably configured, like several other embodiments described herein, to remain substantially uncompressed in the vertical direction, the inclusion of one or more horizontal channels 2207 may aid in providing additional rigidity in the direction of the plane defined by the cells 2102. In such a case, the rigidity of the one or more walls 2104 may be enhanced, and may thus control the compression of the stabilizing structure 2100 such that any collapse or bending occurs substantially only at the one or more joints 2106.

FIGS. 23A-F illustrate an embodiment of a stabilizing structure 3001 configured to be inserted into a wound. The stabilizing structure 3001 preferably comprises at least one top strip 3002 extending in a first direction (e.g., along an x axis) and at least one bottom strip 3004 extending in a second direction (e.g., along a y axis perpendicular to the x axis), these being preferably arranged into an array comprising multiple strips 3002, 3004. The strips 3002, 3004 are preferably connected together in a movably interlocking configuration, which preferably comprises an interlock mechanism 3006. The strips 3002, 3004 are preferably arranged in an un-collapsed configuration wherein the strips 3002 and 3004 are disposed at angles approximately perpendicular to each other. This arrangement forms a first plane that the stabilizing structure 3001 preferably adopts. Preferably, the stabilizing structure 3001 is more rigid in the direction perpendicular to the plane (i.e., in the vertical direction or along a z axis), and thereby substantially resists compression or deformation in that direction.

Figure 23A:
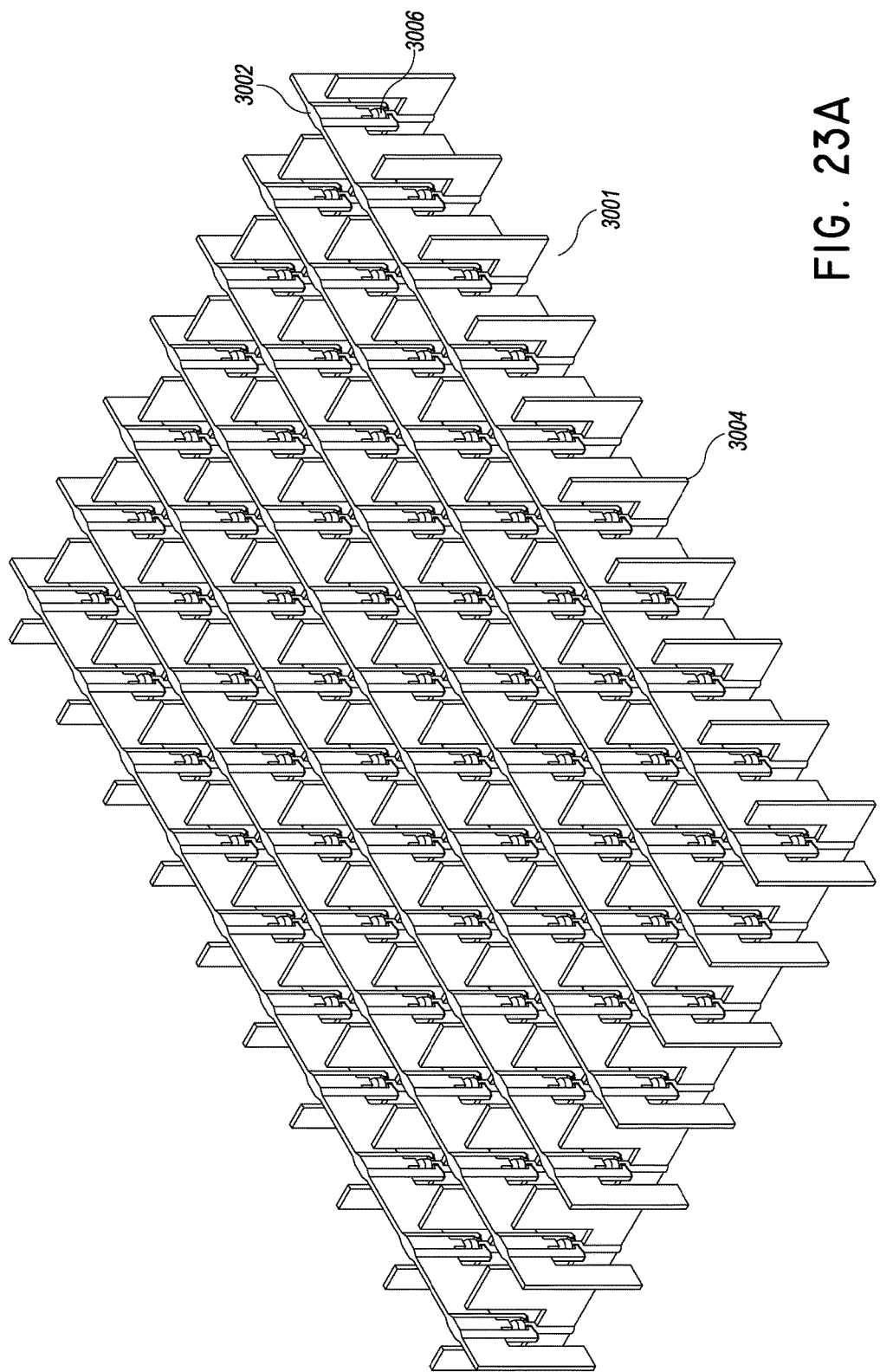
FIGS. 23A-F illustrate multiple views of an embodiment of a stabilizing structure.
Figure 23B:
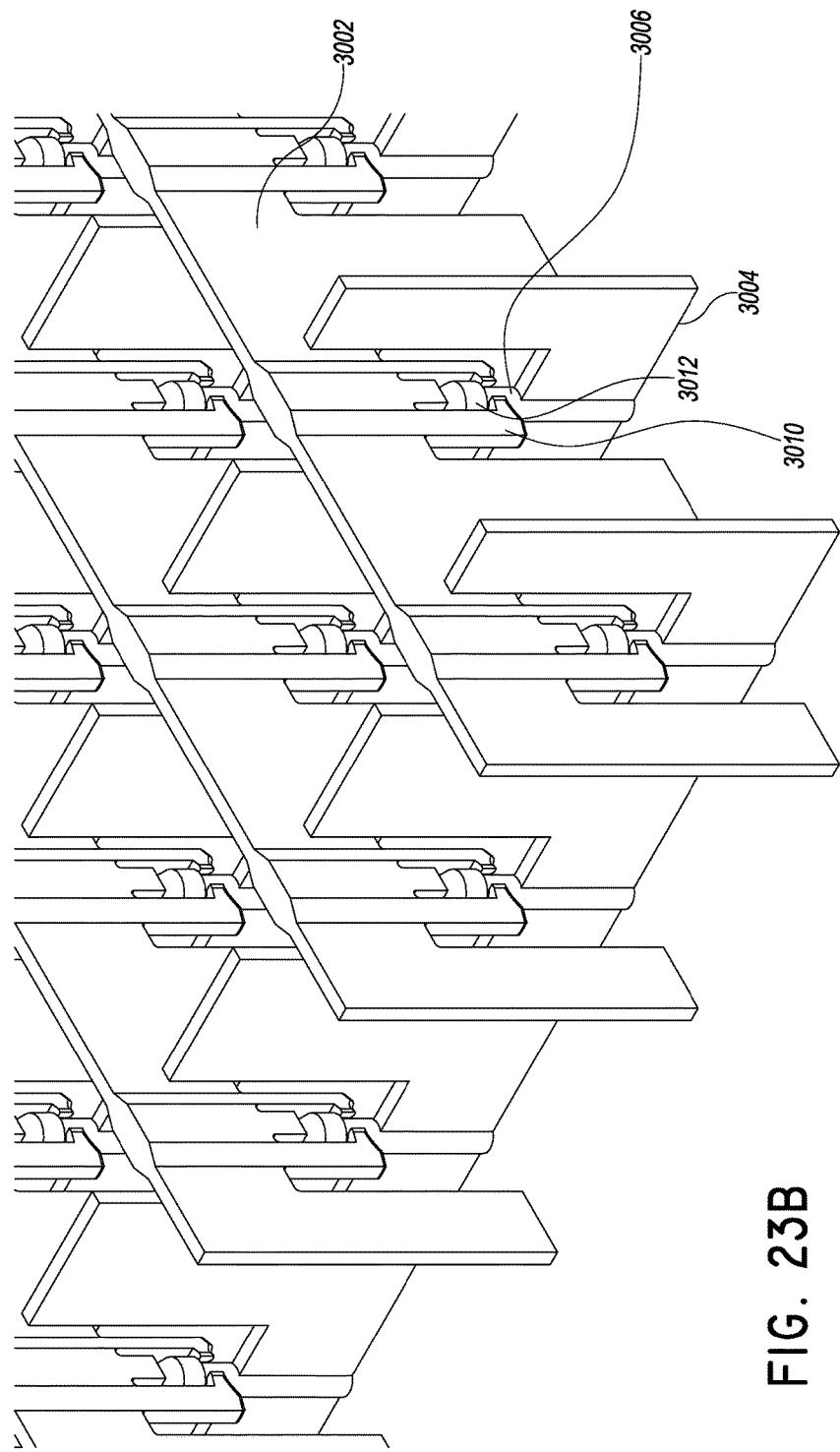
Figure 23C:
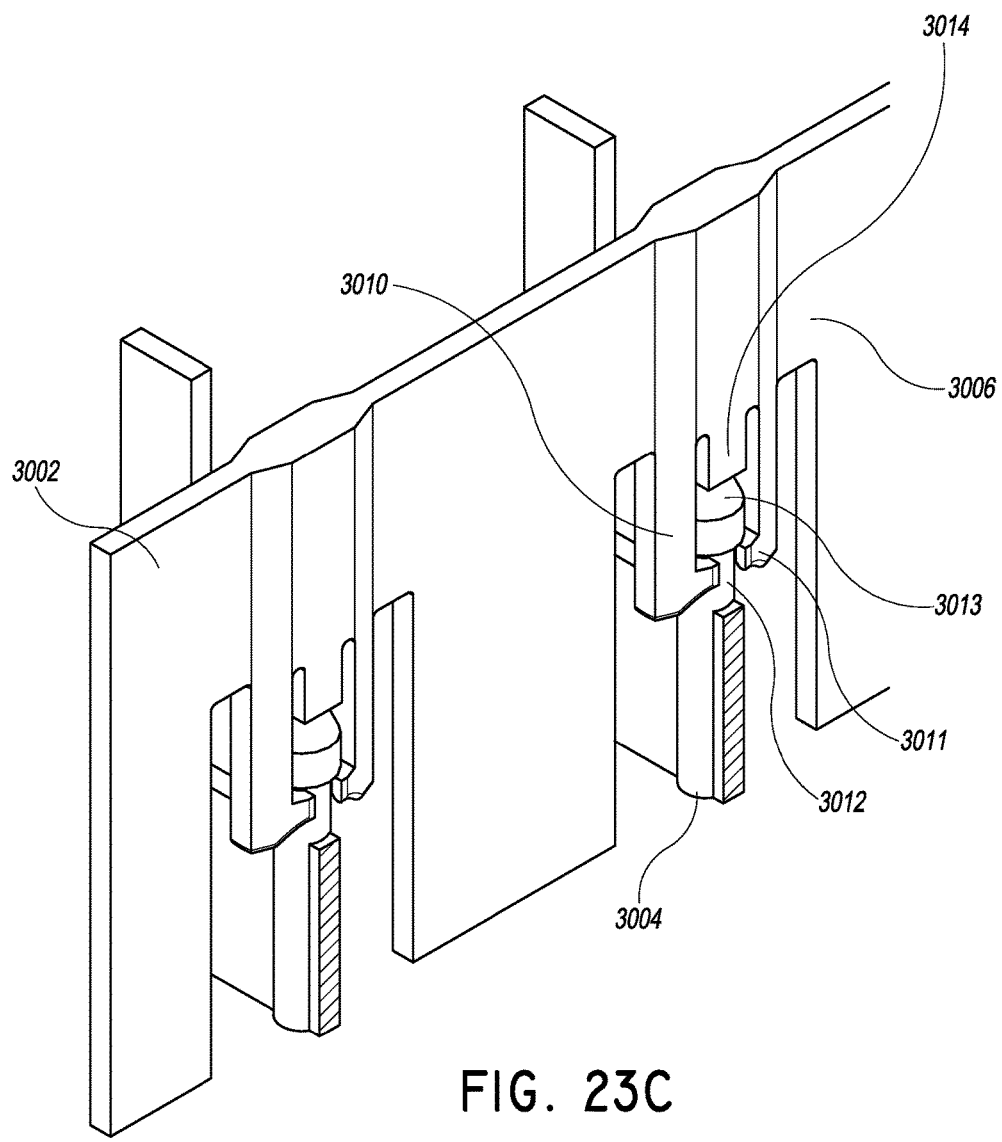
Figure 23D:
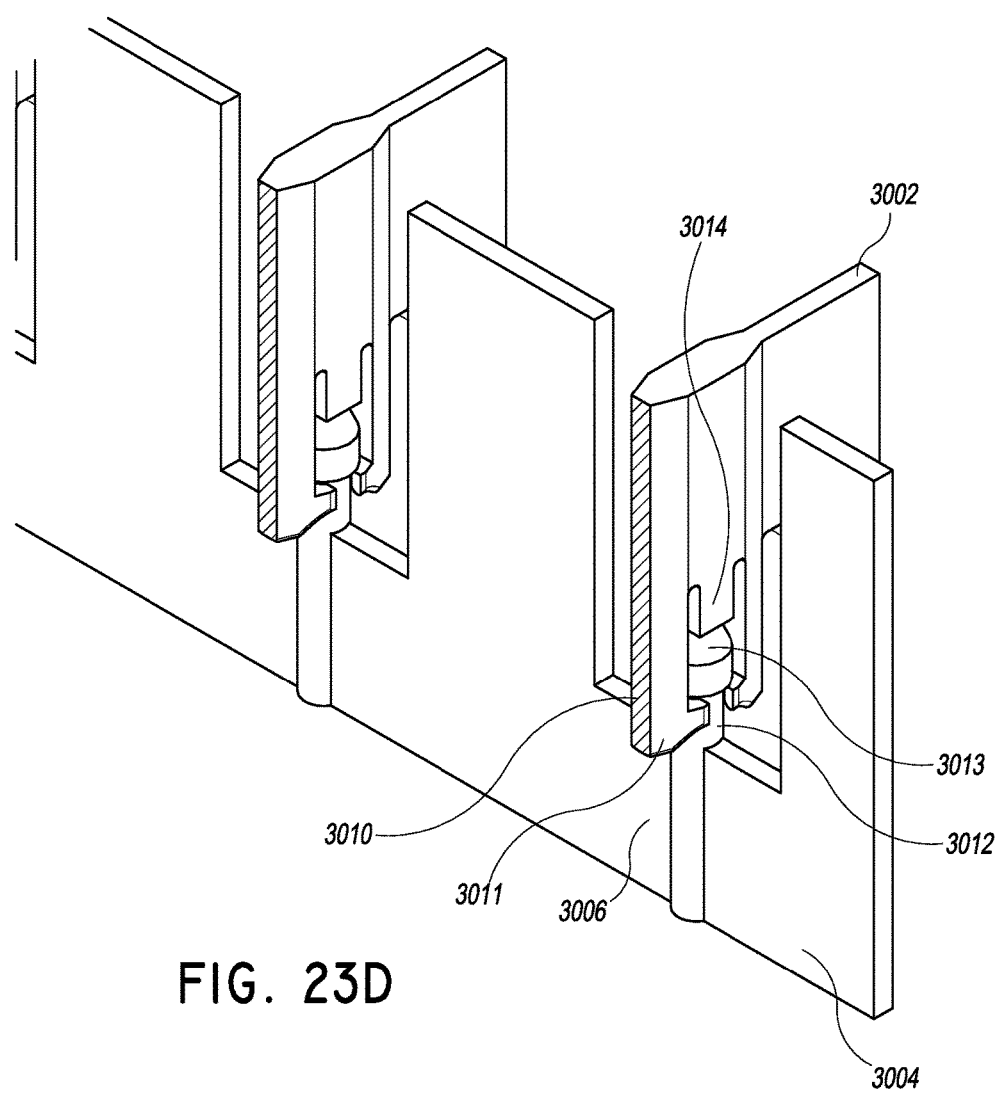
Figure 23E:
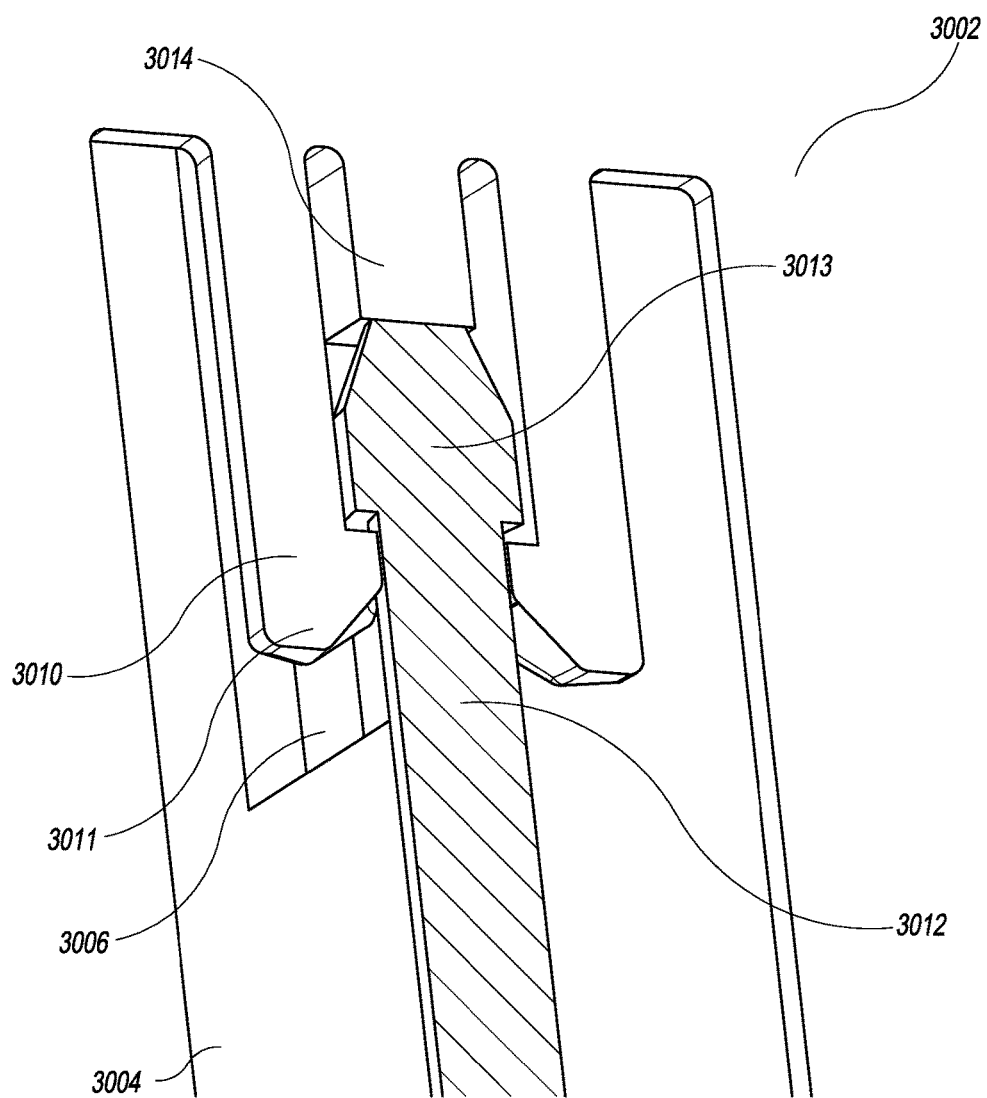
Figure 23F:
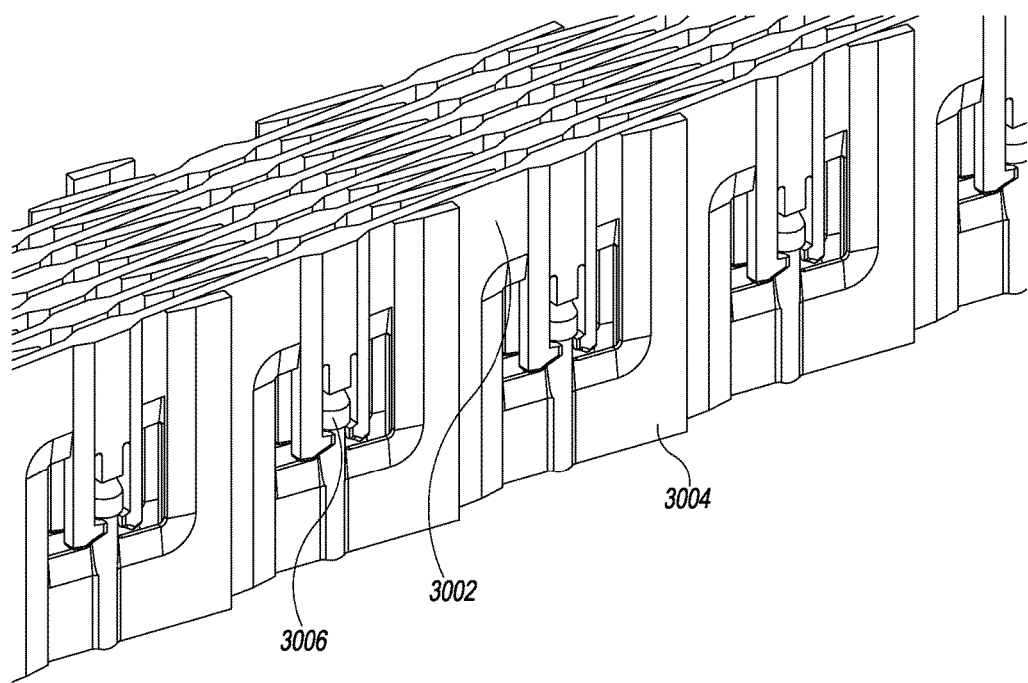

To aid in the closure of a wound, the stabilizing structure 3001 is preferably movable from the substantially un-collapsed configuration to a collapsed configuration, as illustrated in FIG. 23F. This may be beneficial for wound closure and healing, as described previously. In use, negative pressure may apply a closing force across the margins of the wound that the stabilizing structure 3001 is inserted into. As the structure 3001 is preferably configured to be substantially rigid in the vertical direction (i.e., perpendicular to the plane defined by the structure 3001), pressure resulting from atmospheric pressure exerted onto the structure 3001 via the drape is focused substantially downward rather than outward, such that the wound margins are no longer pushed outward as in conventional negative pressure dressings.

Preferably, the structure 3001 adopts a smaller area in the first plane as a result of moving to the compressed configuration. As such, the structure 3001 aids in wound closure by aiding re-approximation of the wound margins. In some embodiments, the stabilizing structures described herein are able to reduce their captured volume when in a collapsed configuration (i.e., the volume change between an uncompressed and compressed stabilizing structure) by at least 10%, preferably at least 15%, and even more preferably at least 25%.

FIGS. 23C-E illustrate close-ups of the interlock mechanism 3006. It is to be noted that although reference may be made to various parts of the interlock mechanism 3006 being present on either the top strip 3002 or bottom strip 3004, this description should not be considered as limiting in terms of orientation, and the same interlock mechanism 3006 may be constructed with the top or bottom strips 3002, 3004 reversed.

In a preferred embodiment, the interlock mechanism 3006 preferably comprises two clasps 3010 extending downward from the top strip 3002. Preferably, the clasps 3010 are parallel to each other so as to be on opposite sides of a projection 3012 extending upward from the bottom strip 3004. The clasps 3010 preferably comprise a lip or hook 3011 that may secure themselves under an end 3013 located at the distal end of the projection 3012. In a preferred configuration, the enlarged end 3013 is arranged such that all or a portion of the lip 3011 engages with the enlarged end 3013. The combination of the lip 3011 and enlarged end 3012 may aid in preventing the top strip 3002 from disengaging in a vertical direction away from the bottom strip 3004. In some embodiments, the projection 3012 may abut on the bottom edge of the top strip 3002. In some embodiments, however, and as illustrated here, a stabilizing post 3014 may be present to locate the distal side of the projection 3012 and enlarged end 3013.

FIGS. 24A-D illustrate an embodiment of a stabilizing structure 3201 assembled in a similar manner to the embodiment illustrated above in FIGS. 23A-F. Here, the interlock mechanism 3006 comprises four clasps 3010 surrounding the projection 3012 and the enlarged end 3013 of the projection 3012. Preferably, the clasps 3010 are arranged in a mutually orthogonal configuration, although different orientations are contemplated as well. It will be understood that any number of clasps 3010 may be used to secure the projection 3012, for example three or five clasps 3010.

Figure 24A:
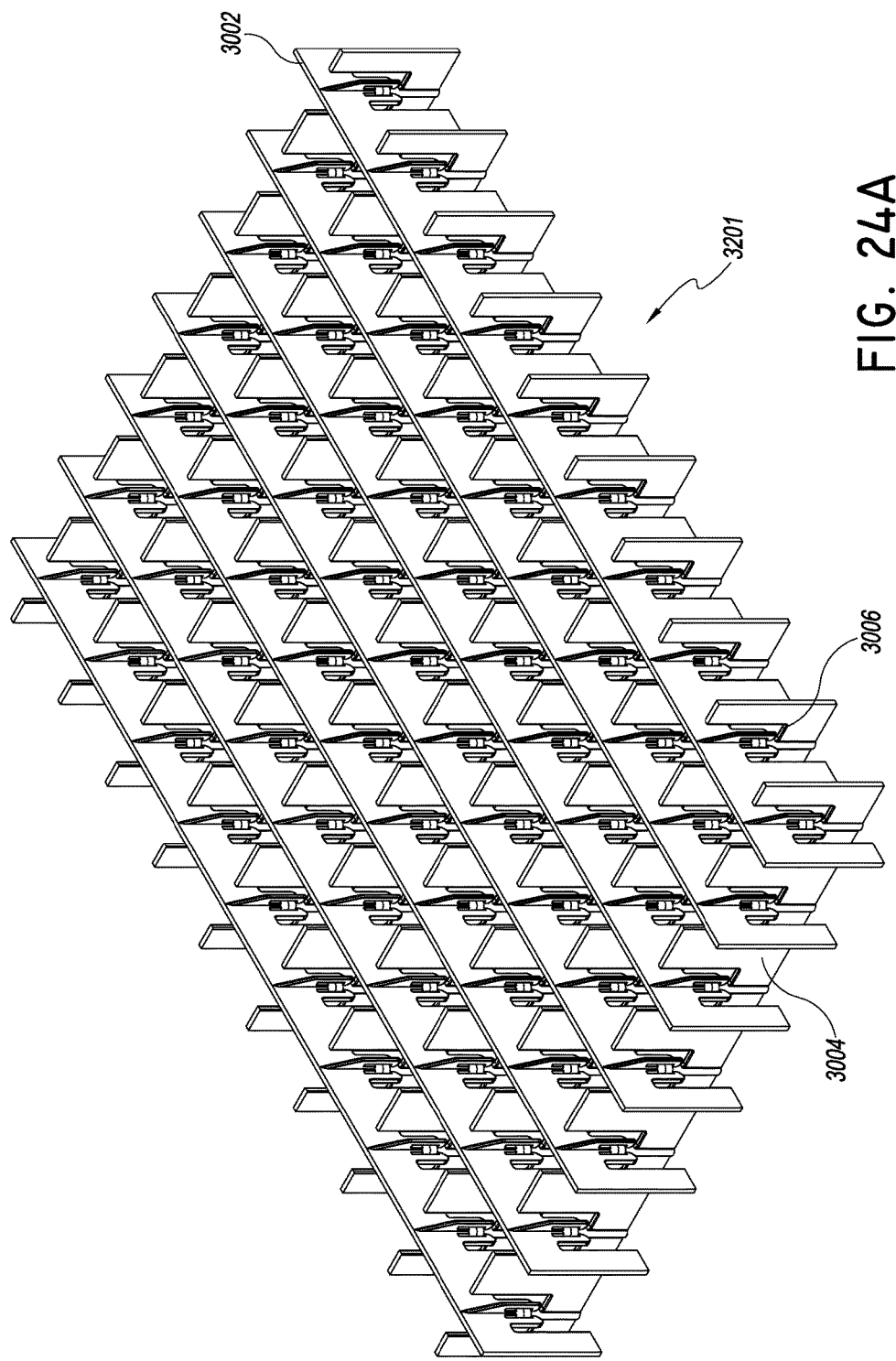
FIGS. 24A-D illustrate multiple views of an embodiment of a stabilizing structure.
Figure 24B:
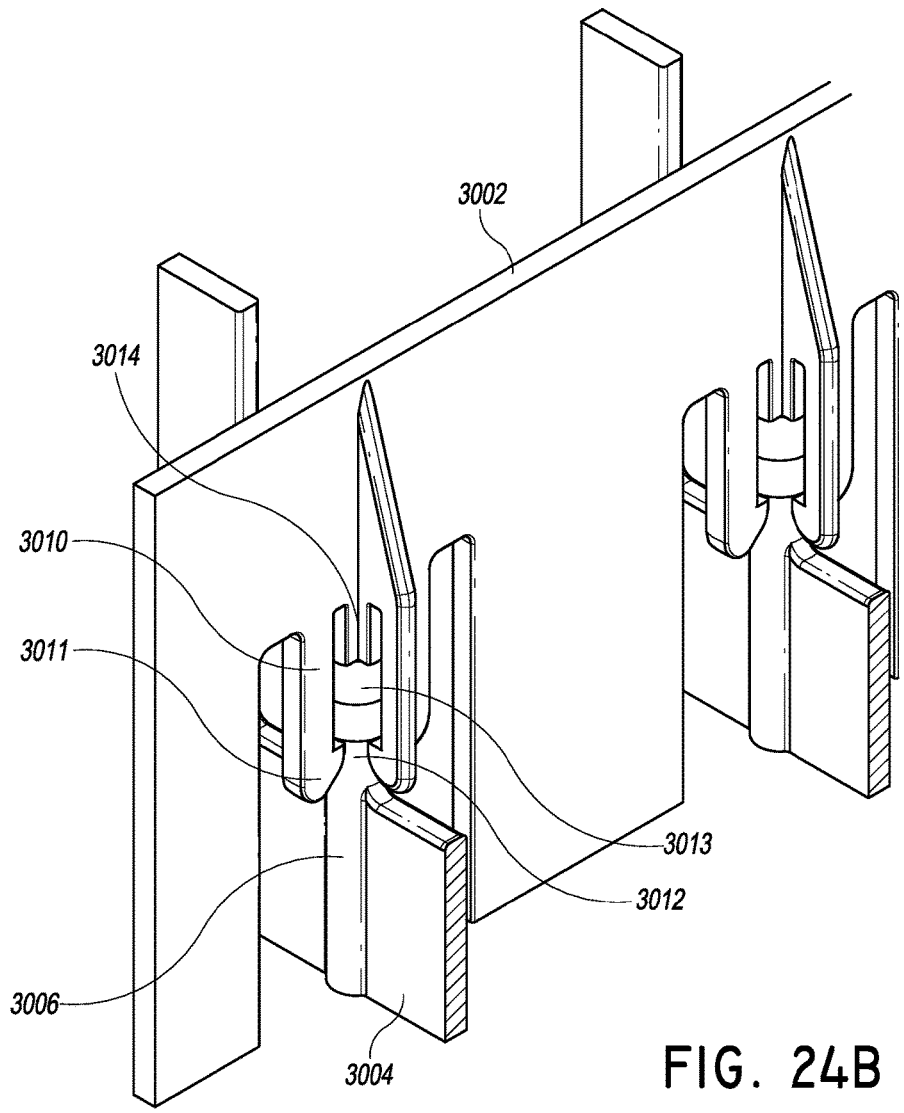
Figure 24C:
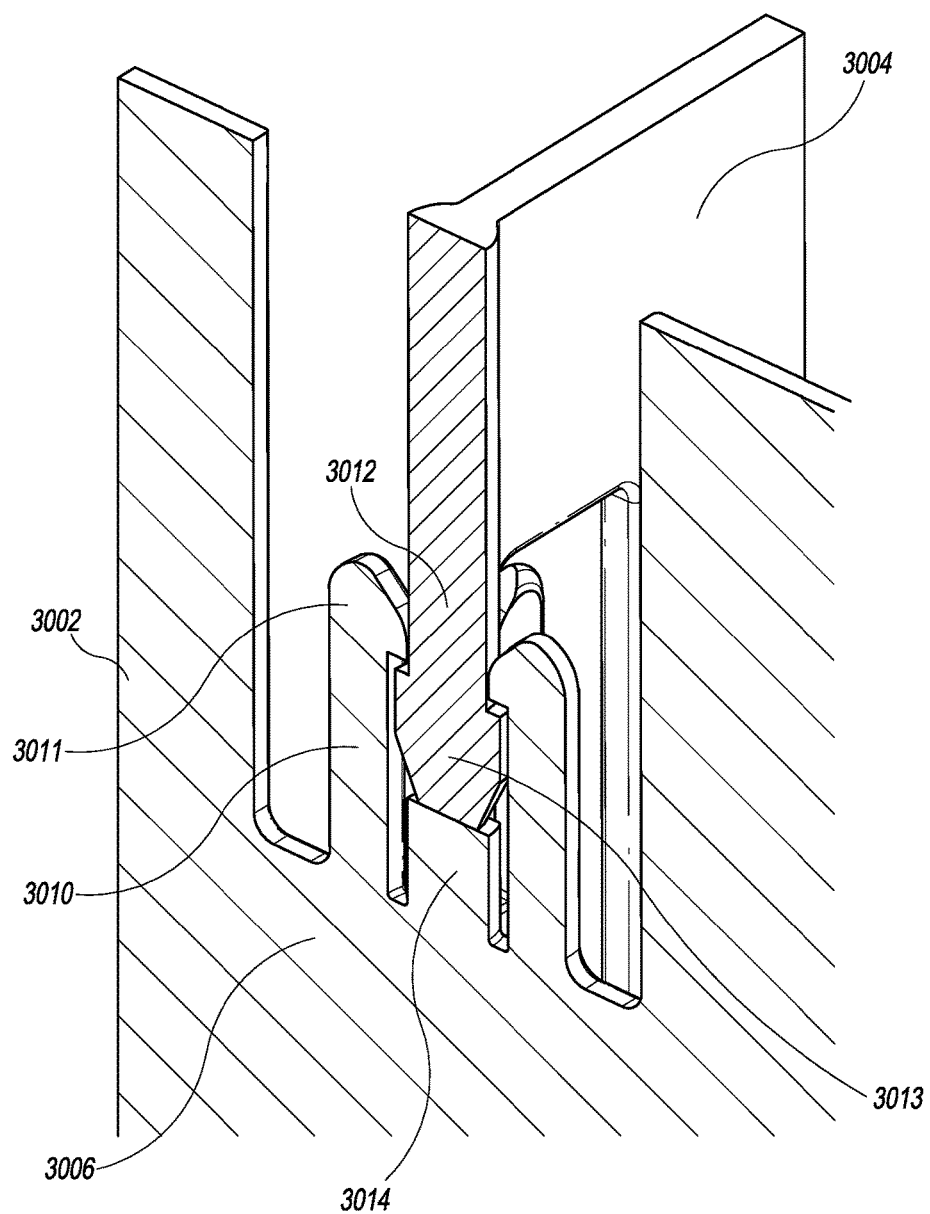
Figure 24D:
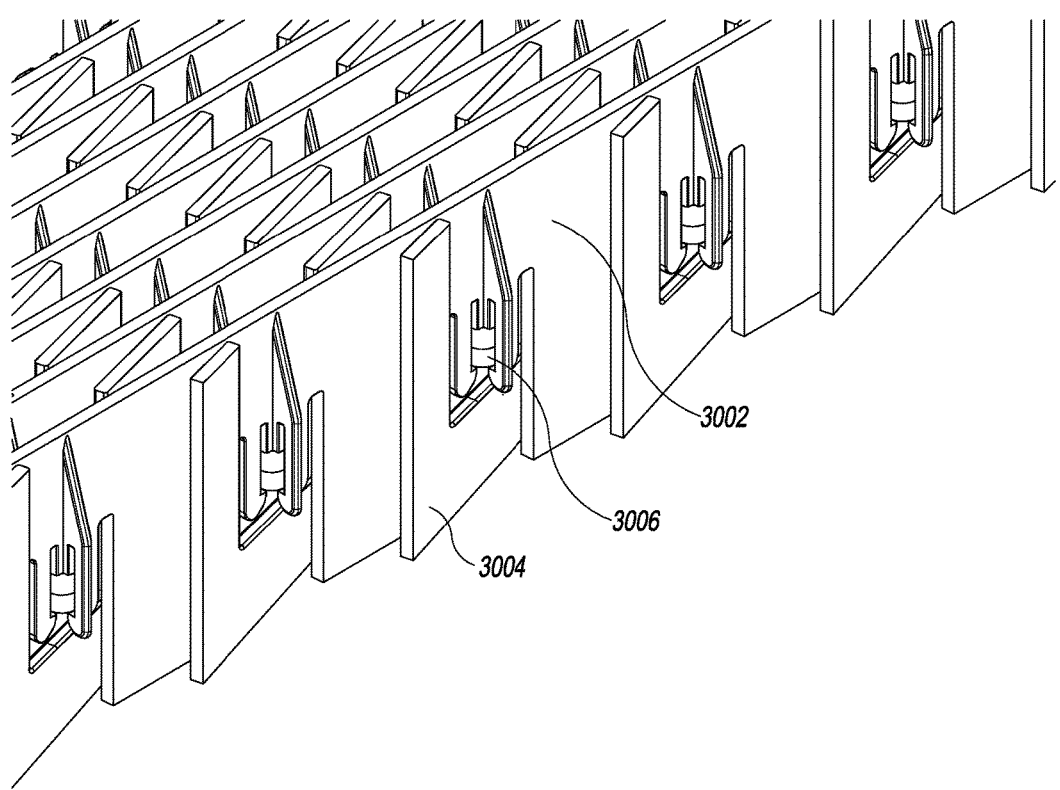

It will be noted that due to the addition of additional clasps 3010 in comparison to the embodiment illustrated in FIGS. 23A-F, the embodiment illustrated here will have a compressed configuration that is slightly larger, as illustrated in FIG. 24D. This may be useful in some situations; for example, some wounds may require a more gradual closure of the wound margins, and the embodiment described here may be well adapted for this purpose. For example, in clinical situations involving compartment syndrome, especially in the abdomen, application of full wound closure may not be appropriate or desirable, as wound closure may cause complications such as excessive pressure on organs and underlying tissue structures and/or reduction of blood flow to distal anatomical structures. Additionally, in some cases a too rapid or complete wound closure may be too painful for a patient. Accordingly, limiting the amount of closure may therefore be beneficial in such types of wounds.

FIGS. 25A-E illustrate an embodiment of a stabilizing structure 3301 comprising an interlock mechanism 3006 arranged in a tubular conformation. In this embodiment, a cup-shaped member 3020 is preferably configured to receive the enlarged end 3013 of the projection 3012. The projection 3012 may extend vertically from the top strip 3002. The cup-shaped member 3020 is preferably cylindrical or tubular in shape, and may extend vertically from the bottom strip 3004, although it will be understood that the cup-shaped member 3020 and projection 3012 may be located on opposite strips.

Preferably, one or more slits 3021 are formed into the cup-shaped member 3020 so as to permit some "give" to permit the projection 3012 to be received into the cup-shaped member. A lip or hook 3022 may also aid in securing the enlarged end 3013 of the projection 3012. A stabilizing post 3014 may also be present to prevent the projection 3012 from extending too deeply into the cup-shaped member 3020.

Figure 25A:
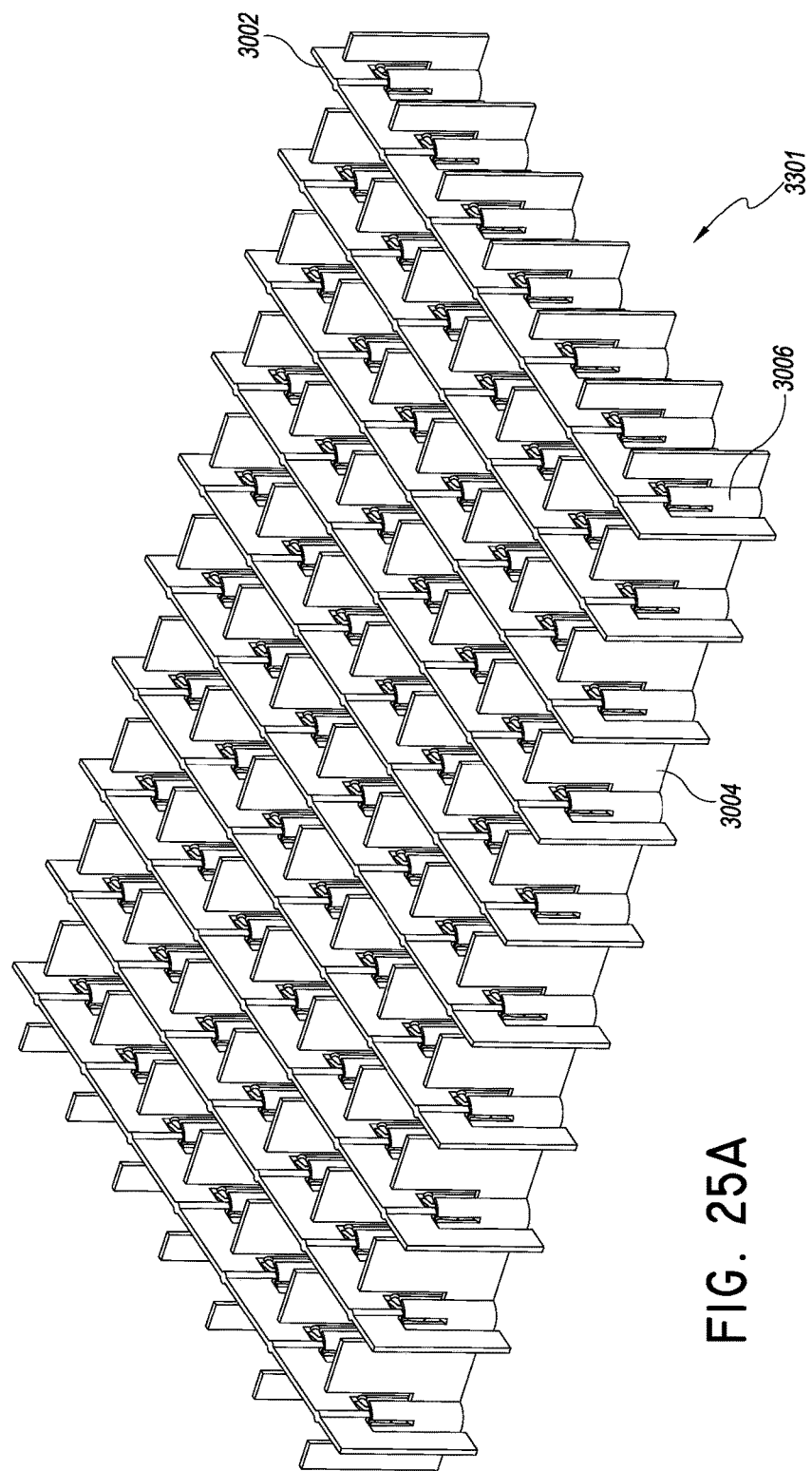
FIGS. 25A-E illustrate multiple views of an embodiment of a stabilizing structure.
Figure 25B:
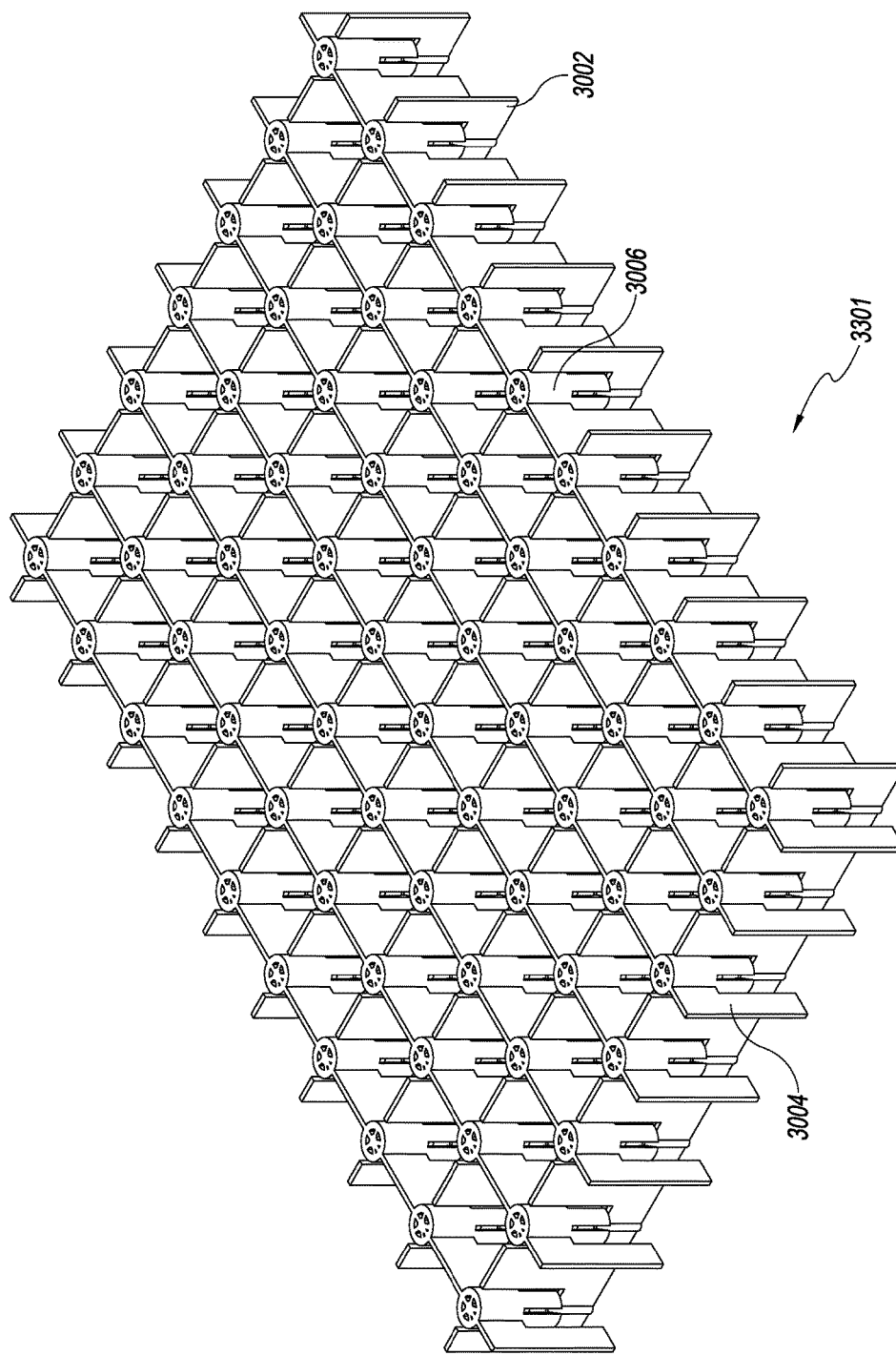
Figure 25C:
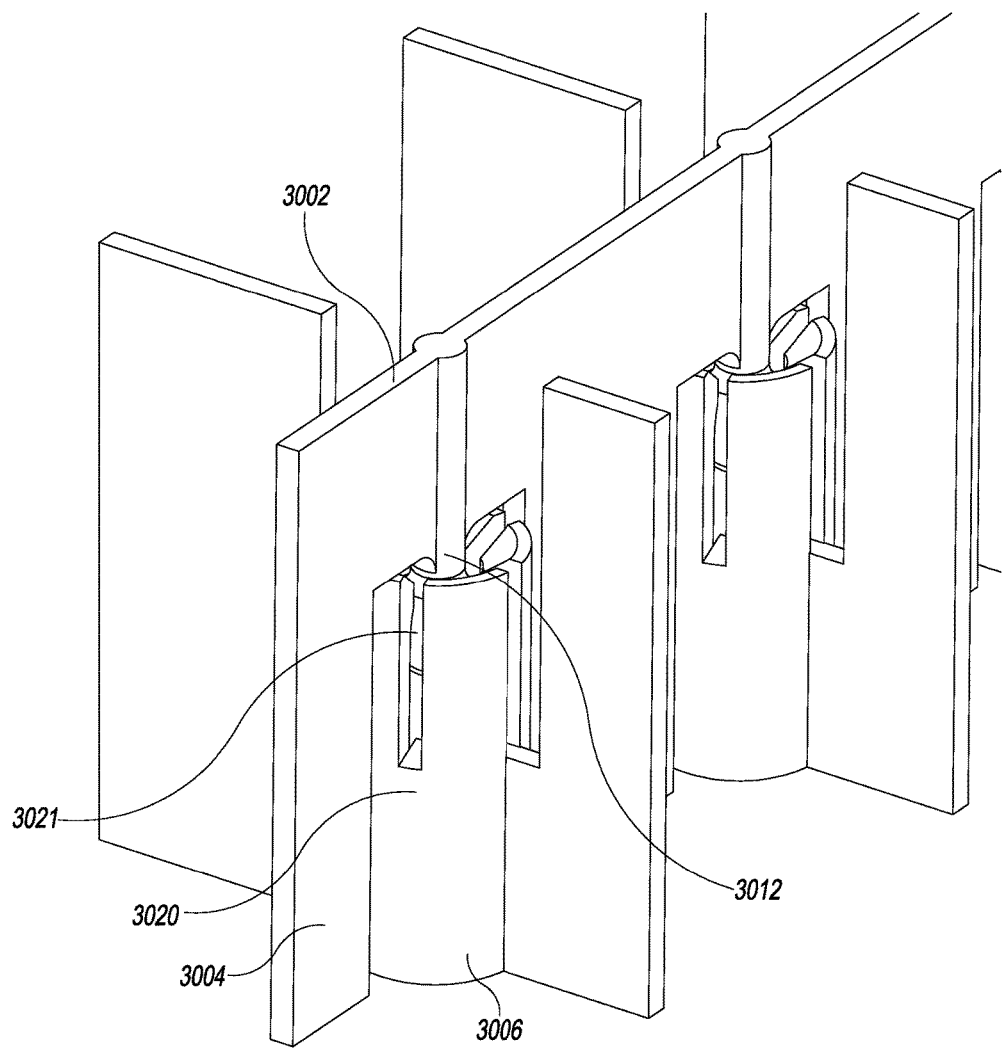
Figure 25D:
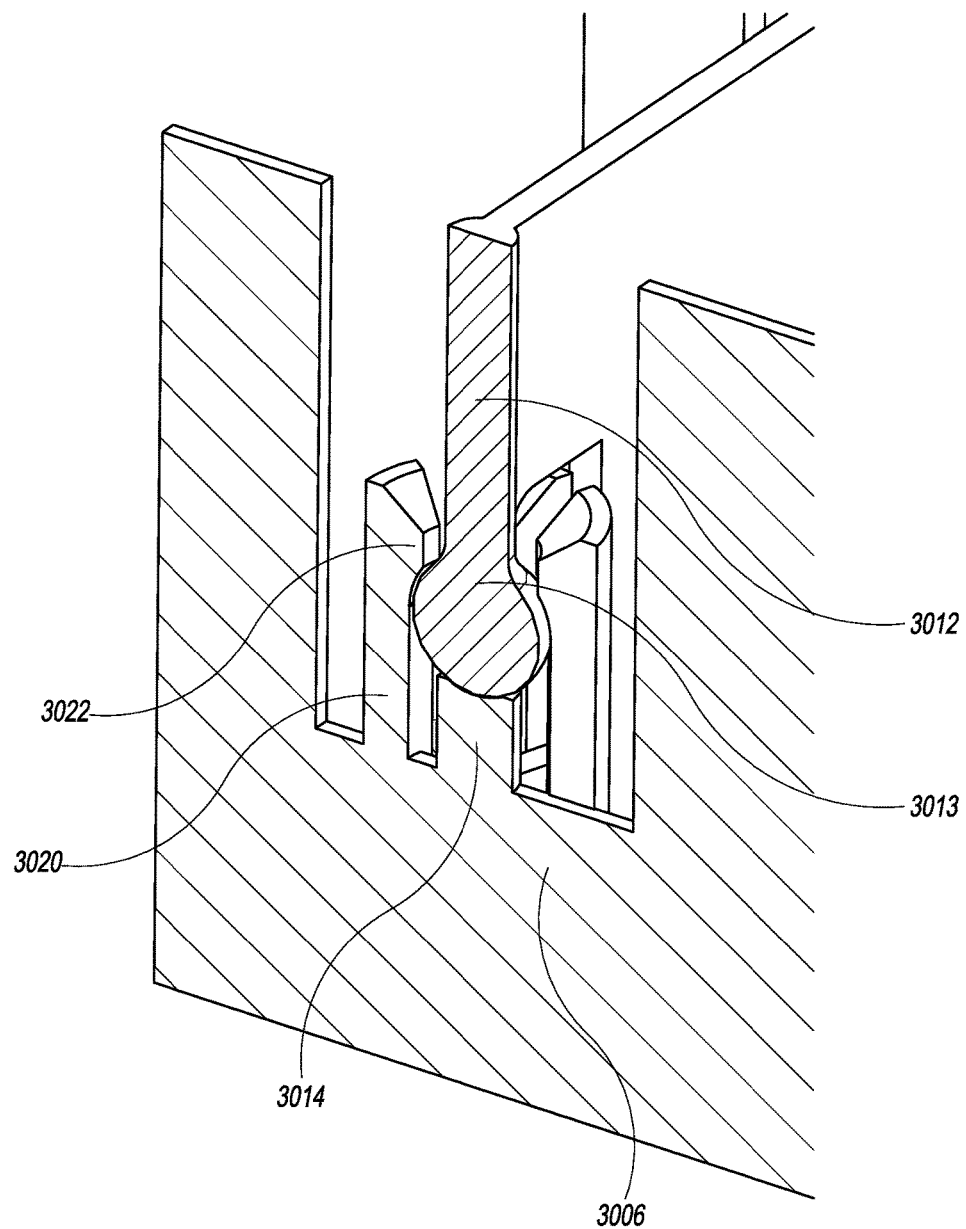
Figure 25E:
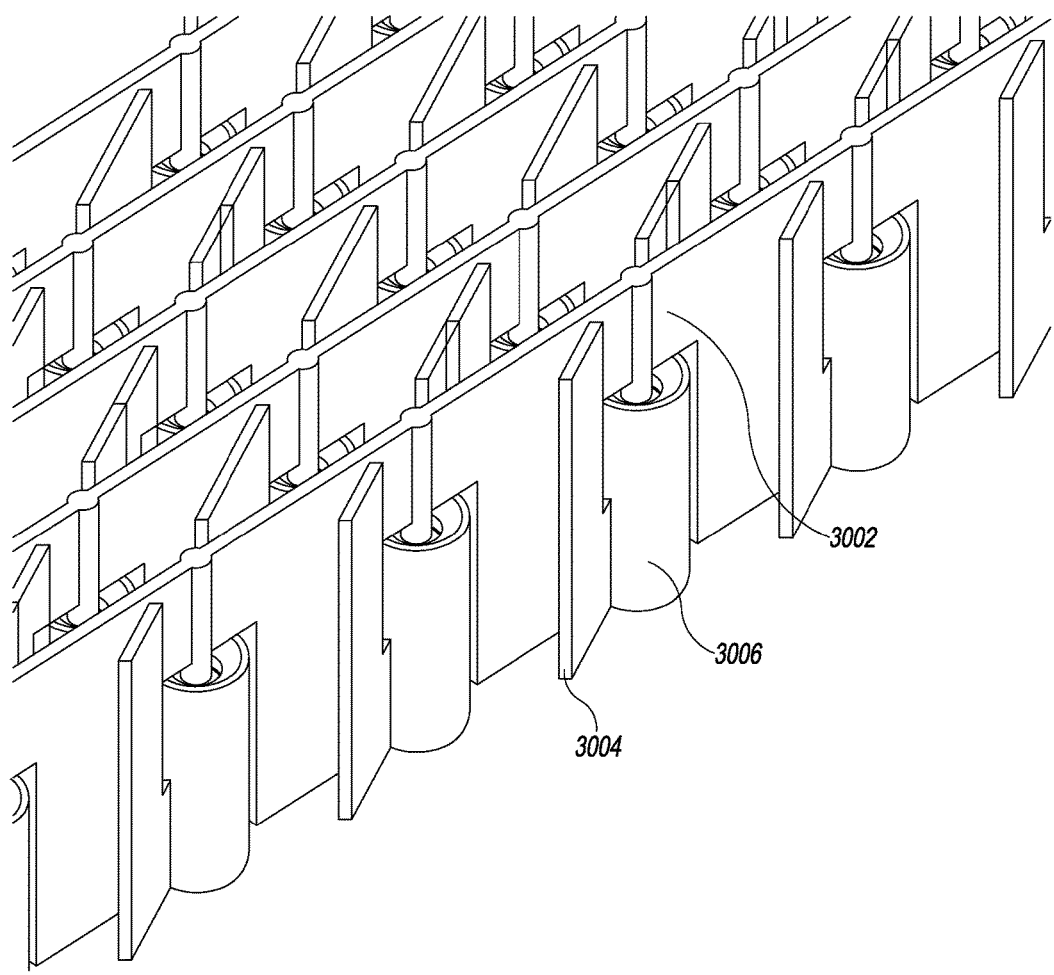

FIG. 25E illustrates a compressed view of an embodiment of the stabilizing structure 3301. Compared to FIG. 23F, this embodiment has a slightly larger compressed configuration.

FIG. 26 schematically illustrates an embodiment of a stabilizing structure 3400 configured to be inserted into a wound. Here, the stabilizing structure 3400 is shown inserted into a wound 3405. Preferably, the stabilizing structure 3400 preferably comprises at least one, and more preferably at least two, long strips 3402 whose longitudinal length may be oriented along a longitudinal axis of the wound 3405, or along a direction along which closure is sought. Each of the one or more long strips 3402 are preferably substantially rigid and extend substantially along the entire length of the wound 3405. In a preferred embodiment, the long strip 3402 is continuous and does not have any breaks or hinges along its length. This is in contrast to certain other embodiments described above.

One or more struts 3404 are preferably attached at one or more points to the long strip 3402. Preferably, these struts 3404 are movably attached, for example via a hinge-like attachment or flexible joint, such that these may collapse in a direction perpendicular to a longitudinal length defined by the length of the one or more long strips 3402. In some embodiments, the struts 3404 may be angled at a non-perpendicular angle with respect to the long strip 3402 so as to collapse more readily. In embodiments comprising two or more long strips 3402, the struts 3404 may be hinged between two parallel long strips 3402.

It will be recognized that while these struts 3404 may be configured to collapse along a direction perpendicular to the longitudinal length of the one or more long strips 3402, the struts 3404 are preferably rigid in a vertical direction (i.e., in the direction extending upward from a plane defined by the wound 3405). As such, a combination of the struts 3404 and the long strips 3402 may thus form a stabilizing structure 3400 that is substantially rigid in a vertical direction while being collapsible in a horizontal direction perpendicular to the longitudinal axis of the long strips 3402 (i.e., in the plane of the wound 3405).

FIG. 27A illustrates a top view of an embodiment of stabilizing structure 3400 cut into an oval shape and inserted into a wound 3405. Preferably, the stabilizing structure 3400 comprises a plurality of elongate strips 3402 whose longitudinal length may be oriented along a longitudinal axis of the wound 3405, or along a direction along which closure is sought. Each of the plurality of elongate strips 3402 is preferably substantially rigid and extends substantially along the entire length of the wound 3405. A plurality of intervening members are positioned between adjacent elongate strips 3402. These intervening members may be struts 3404 as described with respect to FIG. 26, preferably attached at one or more points to the elongate strips 3402. The intervening members may also be portions of elongate strips such as described with respect to FIGS. 23A-25E above, extending perpendicular or at an angle to elongate strips 3402. The stabilizing structure of FIG. 27A may also comprise the embodiments described with respect to FIGS. 21A-22F.

FIG. 27B illustrates a top view of an embodiment of an oval shaped stabilizing structure 3400 inserted into a wound 3405. This embodiment may have the same configuration as described above with respect to FIG. 27A. Additionally, foam 3406 can be inserted between and around the stabilizing structure.

Stabilizing Structures and Wound Closure Devices of FIGS. 28A-31 and 33-35

Figure 28A:
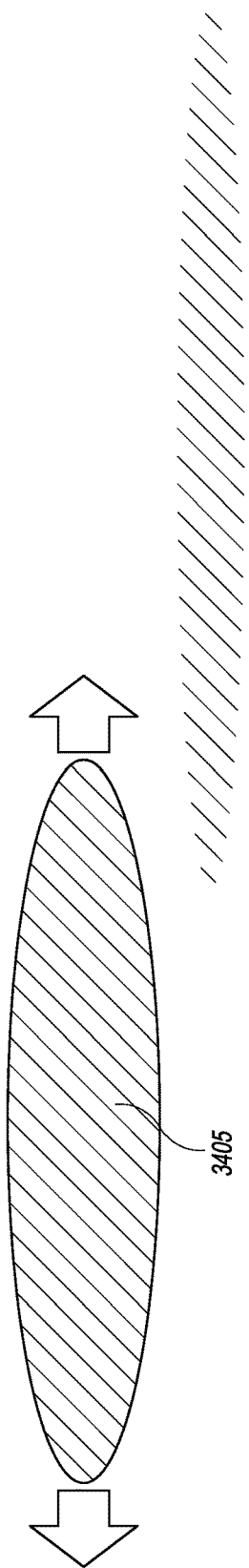
FIGS. 28A-B illustrate embodiments of methods for closing a wound.

FIG. 28A illustrates an embodiment of a method for the closure of a wound using any of the stabilizing structures described hereinbefore or as hereafter described, through the application of tension along an axis of wound 3405. In this example, when the wound is viewed from above, tension is applied along the longitudinal axis of the wound, generally represented by line 3408. Tension along the longitudinal axis prevents contraction of the wound along the longitudinal axis, however the tension along the longitudinal axis can cause the lateral edges of the wound to be drawn together, promoting wound closure. In some embodiments, additional inward tension can be applied to the lateral edges of the wound, thereby providing additional wound closing force.

Figure 28B:
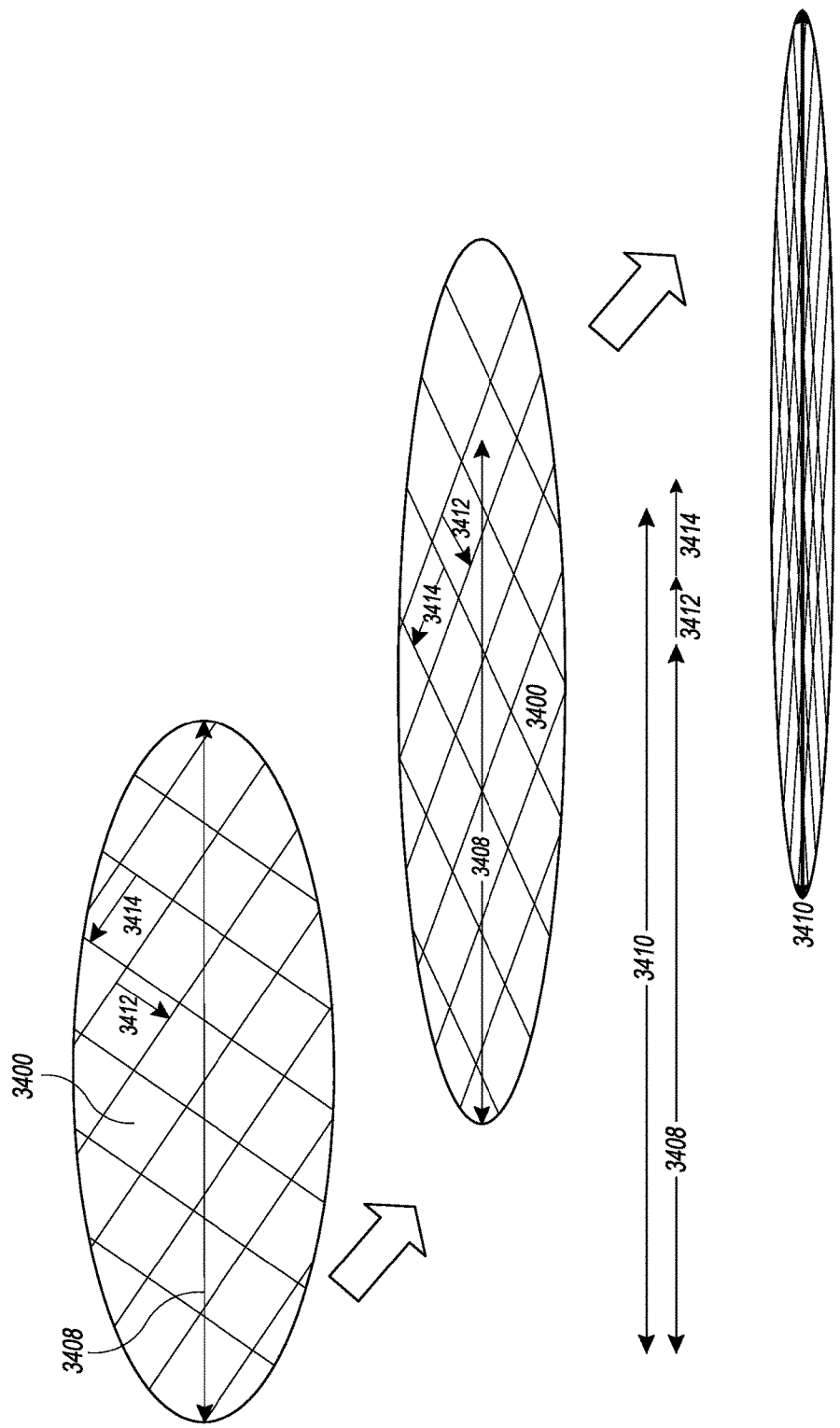

FIG. 28B illustrates an embodiment of a method for the closure of a wound through the use of a stabilizing structure 3400 that collapses and lengthens when a wound is treated under negative pressure. As illustrated, the stabilizing structure 3400 may be cut to an appropriate size to approximate the shape of the wound (e.g., in an oval shape), and the stabilizing structure is placed in the wound 3405. In some embodiments as described above, the stabilizing structure may have a plurality of diamond-shaped cells, and the cells are arranged in the wound in an orientation that causes the cells to be flattened as the lateral edges of the wound come closer together, while becoming longer along the longitudinal axis of the wound. It will be recognized that while this structure is configured to collapse under negative pressure horizontally within the wound in a direction perpendicular to the longitudinal axis of the wound, the structure is substantially rigid in the vertical direction. Line 3408 represents the length of the structure prior to lengthening under negative pressure, while line 3410 represents the final length of the structure after collapsing and lengthening under negative pressure. Lines 3412 and 3414 represent the lengths of particular sections within the stabilizing structure. In certain embodiments, when is wound is treated with application of negative pressure, the structure will collapse inward on one axis, thereby lengthening the structure by some additional amount in another axis that can be the sum of the lengths of lines 3412 and 3414. In some embodiments, the structure can lengthen by amounts other than the sum of lines 3410 and 3412.

In some embodiments, the collapse can occur slowly, thereby applying increasing longitudinal tension over a long period of time. In certain embodiments, the collapse and lengthening of the structure can occur immediately upon application of negative pressure. In further embodiments, the collapse can occur at any rate.

Figure 29A:
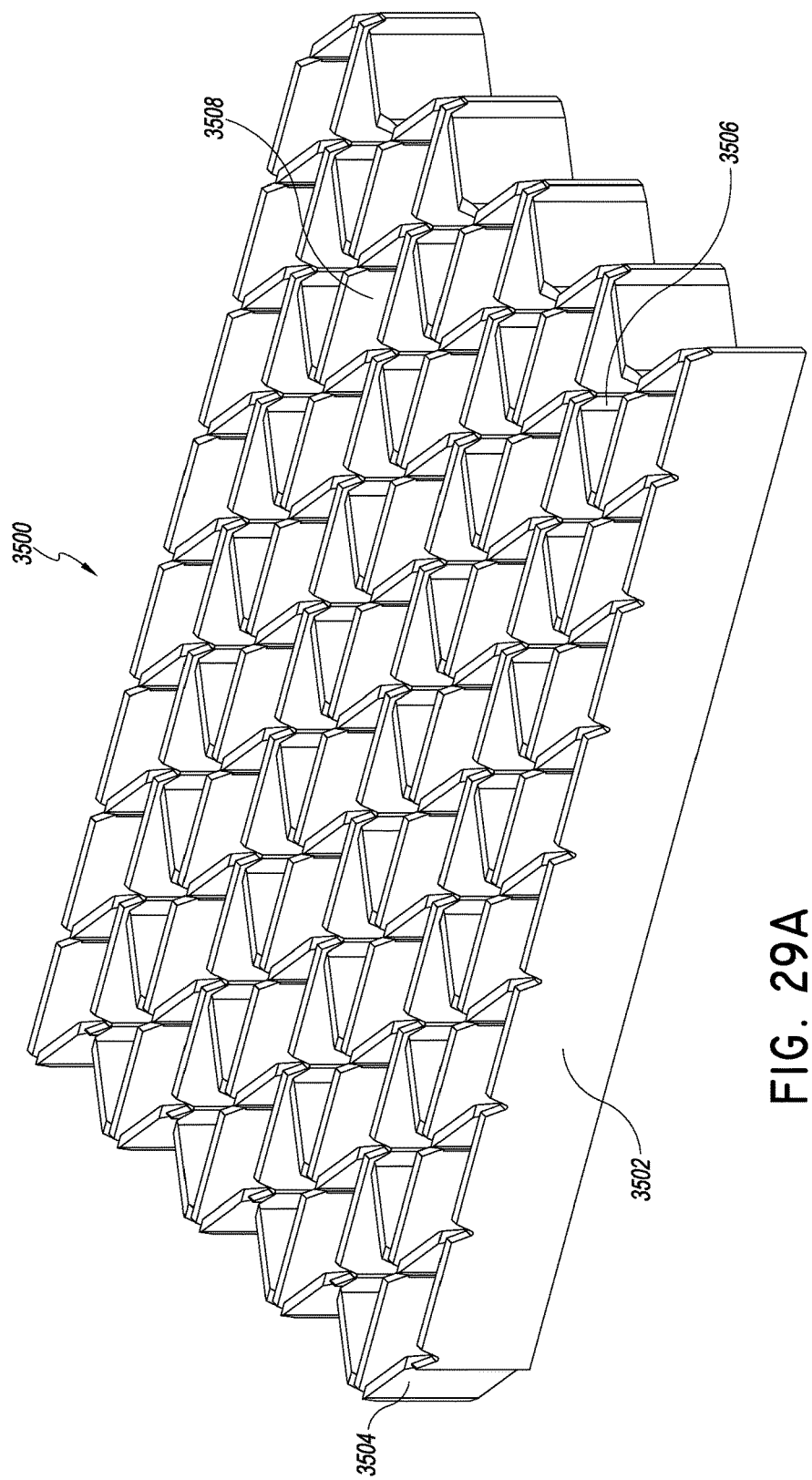
FIGS. 29A-C illustrate multiple views of an embodiment of a stabilizing structure.
Figure 29B:
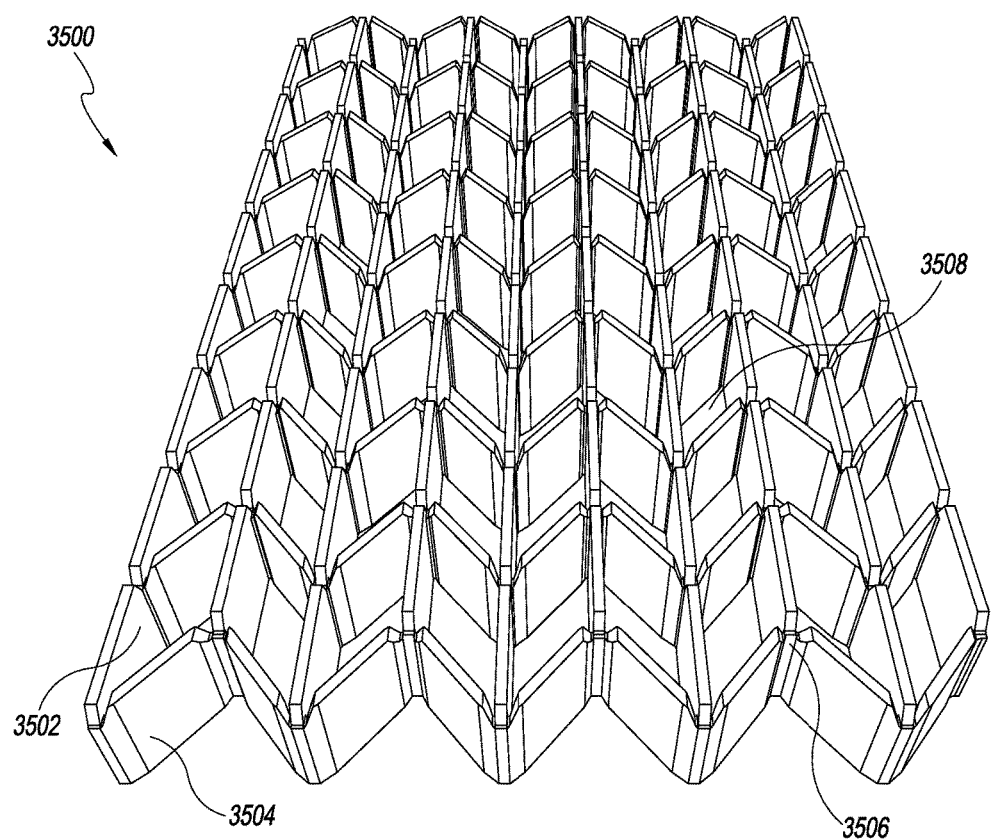
Figure 29C:
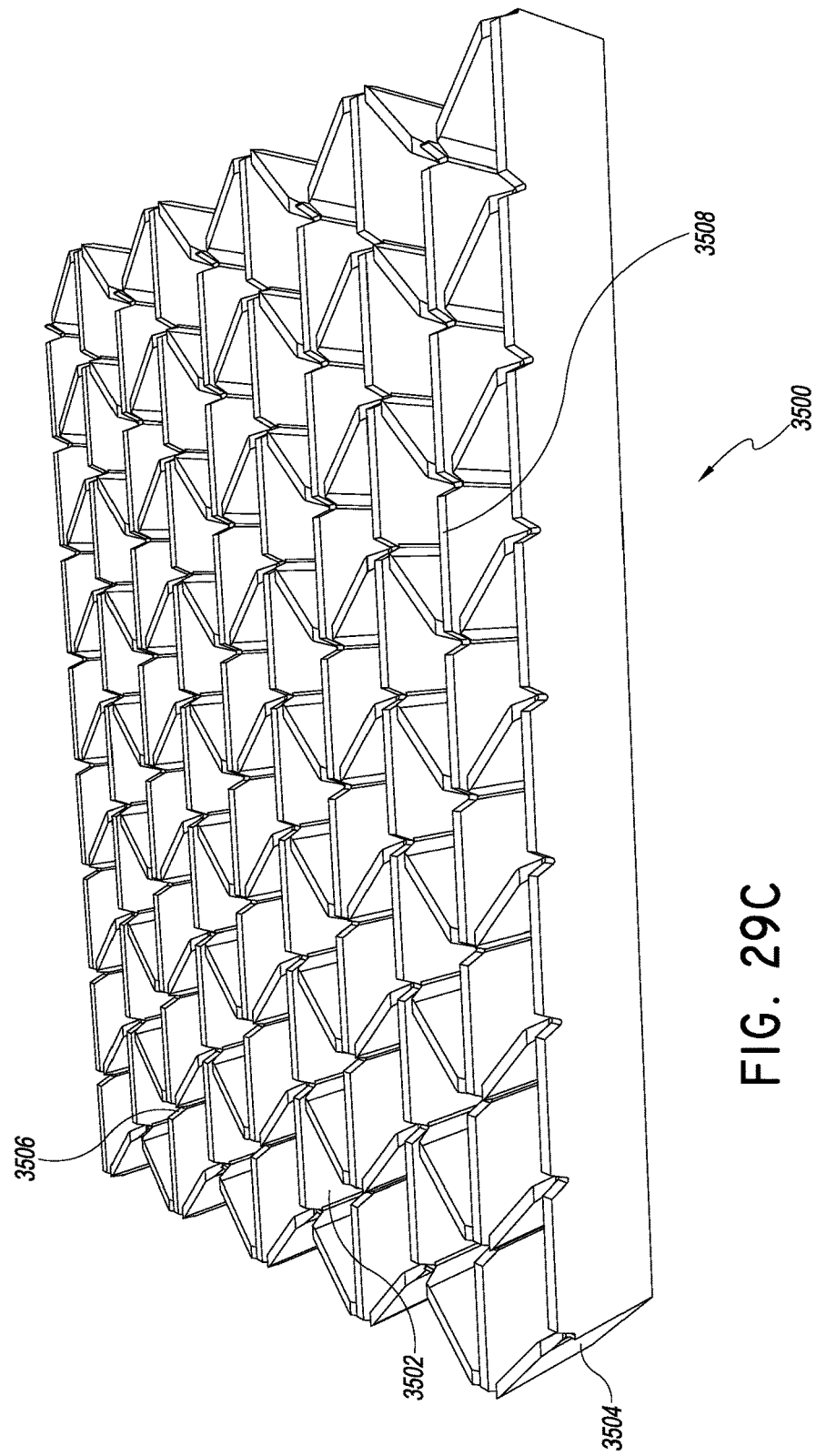

FIGS. 29A-C illustrate another embodiment of a stabilizing structure 3500. The stabilizing structure 3500 comprises a plurality of elongated strips 3502 arranged in parallel, and whose longitudinal length can be aligned with the longitudinal axis of a wound when placed in a wound. The stabilizing structure further comprises a plurality of intervening members 3504 connected to the elongated strips 3502 by a plurality of joints 3506. As illustrated, the plurality of intervening members 3504 between adjacent elongate strips 3502 define a row of cells 3508 between each pair of adjacent elongate strips.

In some embodiments, the elongated strips 3502 are rigid. In certain embodiments, the elongated strips 3502 are semi-rigid. In particular embodiments, the elongated strips 3502 are flexible. In some embodiments, the elongated strips 3502 are compressible. As illustrated in FIGS. 29A-29C, one embodiment comprises a plurality of strips that are rigid in a vertical dimension but also are flexible and capable of bending along their length.

In some embodiments, the intervening members 3504 are rigid. In certain embodiments the intervening members 3504 are semi-rigid. In particular embodiments, the intervening members are flexible. In some embodiments, the intervening members 3504 are compressible. As illustrated in FIG. 29A-29C, one embodiment comprises intervening members in the form of panels equally spaced apart between adjacent strips, to define a plurality of similar-shaped (e.g., diamond-shaped) cells. In other embodiments, the intervening members need not be equally spaced. The intervening members may be attached to the strips by joints 3506 in the form of a hinge (e.g., a living hinge or a more flexible piece of material between the strips and the intervening members).

In some embodiments, the plurality of intervening members 3504 are configured to pivot relative to the elongated strips 3502 and to collapse so as to allow the elongated strips to collapse relative to one another and come closer together. In some embodiments, the joints 3506 are configured to pivot and collapse in only one direction. In certain embodiments, the joints 3506 are configured to pivot and collapse in both directions, comprising a full 180 degrees of rotation relative to the elongated strips 3502. In certain embodiments, when the joints pivot, they pivot completely so as to rest the intervening members 3504 against the elongated strips 3502. In some embodiments, the joints do not pivot completely and the intervening members do not come to rest against the elongated strips 3502.

Preferentially, in certain embodiments, by controlling the direction in which the pivoting occurs, the collapsed length of the stabilizing structure 3500 can be controlled. In particular embodiments, because of the rigidity of the elongate strips, the cells 3508 in a row between adjacent elongate strips are configured to collapse together as the adjacent elongate strips 3502 collapse relative to one another. In some embodiments, one or more rows of cells 3508 between adjacent strips 3502 are configured to collapse in a first direction, and one or more rows of cells between adjacent strips 3502 are configured to collapse in a second direction opposite the first direction. As illustrated in FIGS. 29A-29C, the orientation of cells in adjacent rows alternates so that cells of a first row collapse in a first direction, and cells of a next row collapse in an opposite second direction. Joints 3506 may be configured so that joints 3506 in adjacent rows collapse in different directions.

By configuring the joints 3506 and/or cells of the stabilizing structure to pivot and collapse in preferred directions, the length of the collapsed structure can be modified. The embodiment shown in FIGS. 29A-29C will have a shorter collapsed length than a structure where all the rows of cells 3508 are configured to collapse in the same direction. Thus, the collapsed length of the structure can be controlled depending on the orientation of the cells and the direction in which the intervening members collapse between adjacent rows. In some embodiments as described above with respect to FIGS. 28A-28B, the stabilizing structure preferably lengthens after collapse under negative pressure. In other embodiments, it may be preferred that the stabilizing structure not lengthen after collapse under negative pressure.

In FIGS. 29A-29C, the intervening members 3504 in adjacent rows are generally aligned so that the intervening members connect to the elongate strips at approximately the same location on opposite sides of the strip and share the same joint 3506 location. In other embodiments, the intervening members 3504 between a first elongate strip 3502 and a second elongate strip 3502 are offset relative to intervening members 3504 between the second 3502 and a third adjacent strip 3502. In these embodiments, the intervening members 3504 are staggered such that they do not share the same joint 3506 location.

As shown in FIGS. 29A-29C, the enclosed cell 3508 formed by two intervening members and two sections of the elongated strips is a quadrilateral. In some preferred embodiments, the enclosed shape can be a square, rectangle, diamond, oblong, oval, and/or parallelepiped. In some embodiments, the enclosed shape is a rhomboid. In certain embodiments the enclosed shape is a trapezoid.

In certain preferred embodiments, the joint 3506 may be configured to limit the range of motion of the intervening member 3504, and may be used to prevent the intervening members 3504 from becoming fully perpendicular to the adjacent strips. Thus, the joint may be configured to pre-set the intervening members 3504 in a partially collapsed position. For example, a lip or other portion of material at the joint may be used to limit the angular motion of the intervening members. The lip or other portion of material may also prevent the joint from collapsing completely flat. In some embodiments, the joint may be configured to prevent the intervening members from rotating in 180 degrees along the plane formed by the strips.

In some embodiments, when the stabilizing structure 3500 is placed in a wound, the elongated strips 3502 are positioned generally parallel to the lateral edges of the wound. Preferably, the stabilizing structure is configured in the wound such that the elongated strips are positioned parallel to the longitudinal axis of the wound, as described with respect to FIGS. 28A-28B above. The strips may also bend along their length and bow outwardly to fit within the wound. The stabilizing structure may be cut to an appropriate size to fit the structure in the wound. In other embodiments, the elongated strips 3502 are positioned perpendicular to the edge of the wound, or may not be oriented along any edge of the wound.

In the embodiments of FIGS. 29A-29C, as well as in other embodiments of stabilizing structures described herein, the strips can be constructed from a material selected from the group consisting of silicone, rigid plastics, semi-rigid plastics, flexible plastic materials, composite materials, biocompatible materials and foam. In some embodiments, the intervening members can be constructed from a material selected from the group consisting of silicone, rigid plastics, semi-rigid plastics, flexible plastic materials, composite materials, biocompatible materials and foam. In some embodiments, the stabilizing structure is surrounded by absorbent materials. In certain embodiments the stabilizing structure is surrounded by non-absorbent materials. In some embodiments the material surrounding the stabilizing structure is foam. In particular embodiments, the spaces between the intervening members 3504 and the elongated strips 3502 are filled with foam.

Figure 30A:
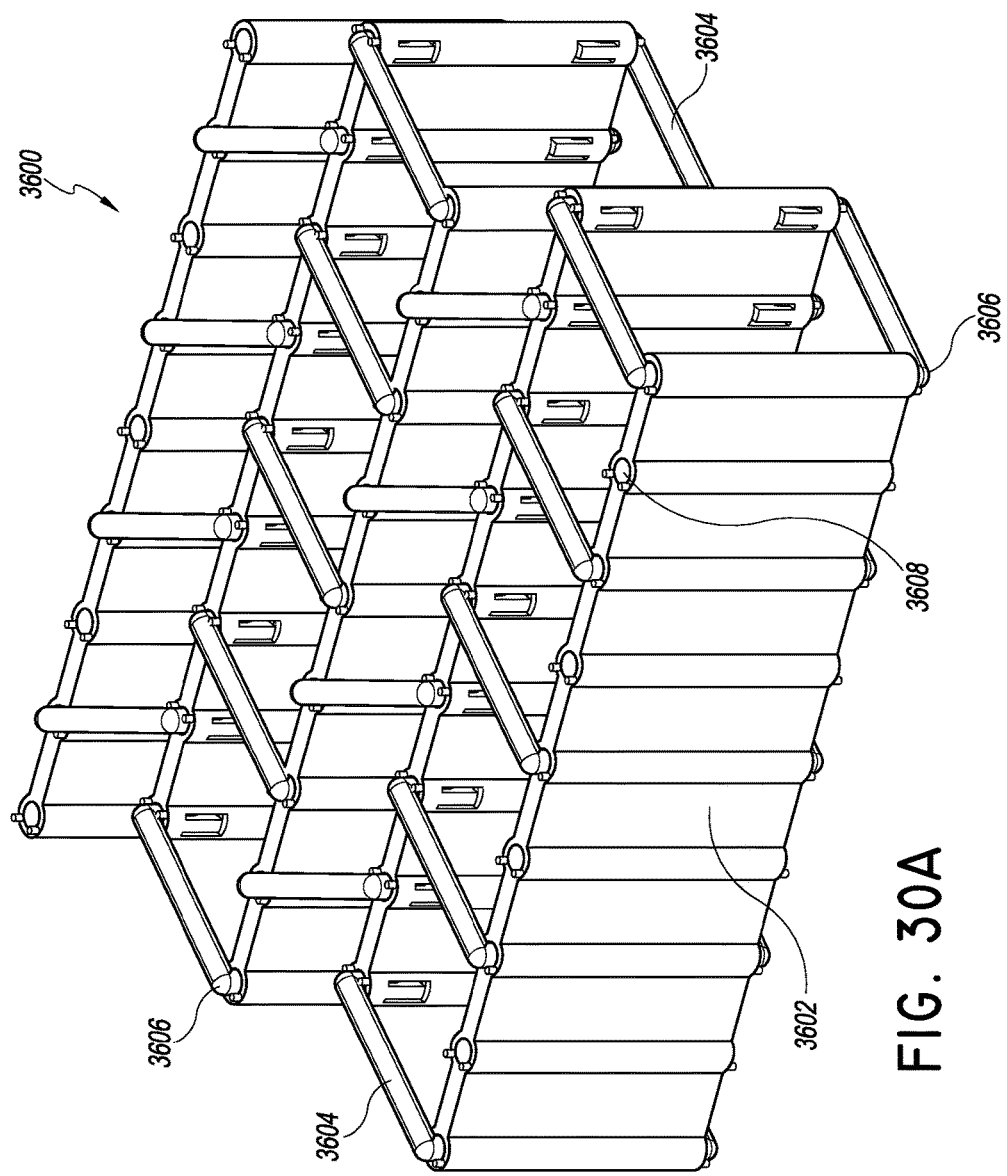
FIGS. 30A-G illustrate multiple views of an embodiment of a stabilizing structure.

FIGS. 30A-G illustrate an embodiment of a stabilizing structure 3600 that is similar to the ones described above in relation to FIGS. 29A-C and FIG. 28B. As illustrated in FIG. 30A, in some embodiments, the stabilizing structure 3600 comprises a plurality of elongated strips 3602 connected by a plurality of intervening members 3604 at a plurality of joints 3606. As illustrated in FIGS. 30A-G, the plurality of intervening members comprise a plurality of bars 3604 connecting adjacent elongated strips and connected to the elongated strips at upper and lower joint locations. The plurality of joints in one embodiment comprise a plurality of pins 3606 connected to the bars and received in upper and lower vertical openings in the strips 3602. Other types of joints are also contemplated, including ball joints. The bars are preferably equally spaced within a row between adjacent elongated strips, and may be offset or staggered in an adjacent row, such that in an adjacent row, the bars connect to the elongate strip at a location between the bars of the first row. In other embodiments, the intervening member can comprise a wire or other elongate structure configured to extend between adjacent elongated strips.

Figure 30B:
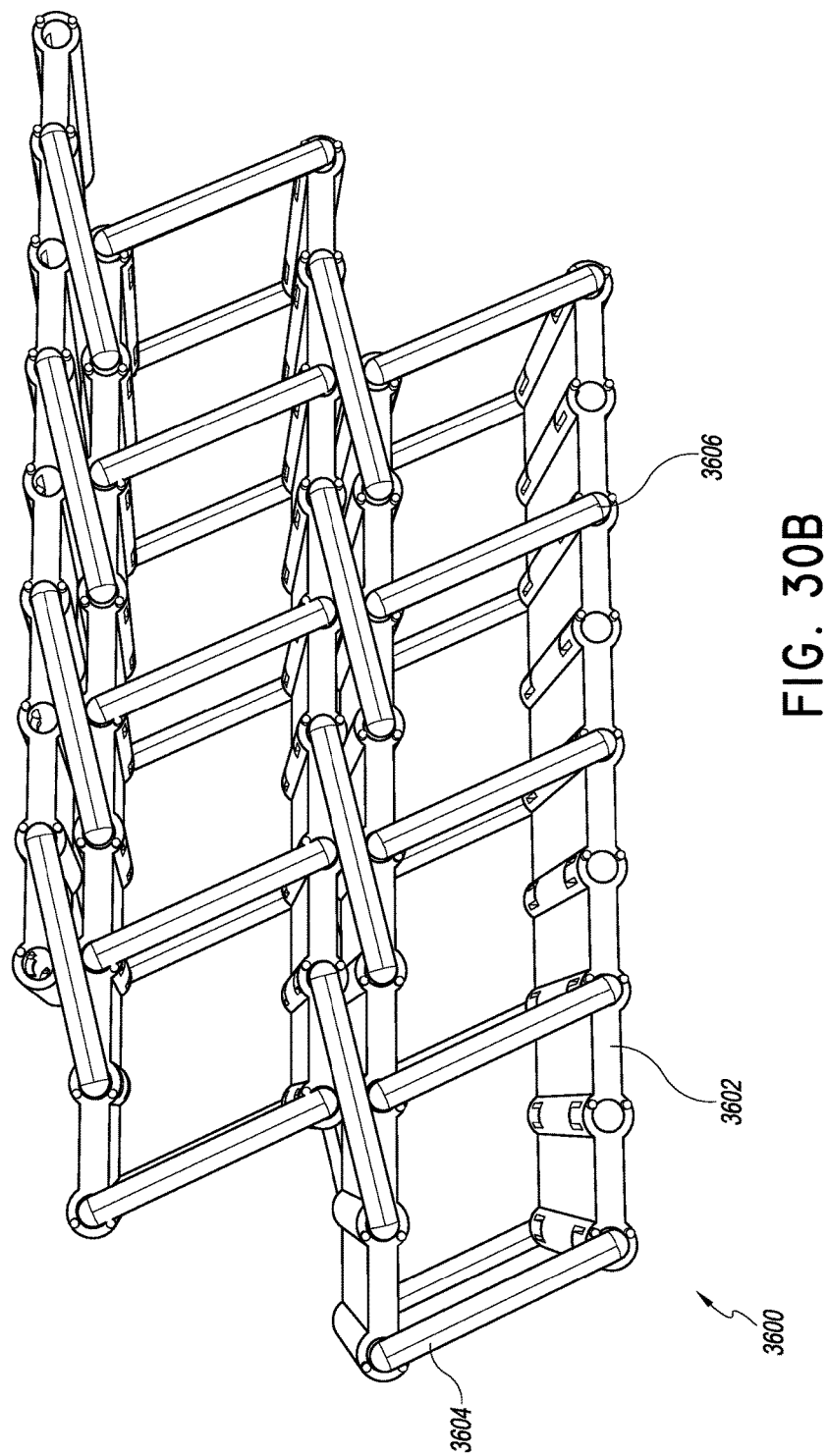
Figure 30C:
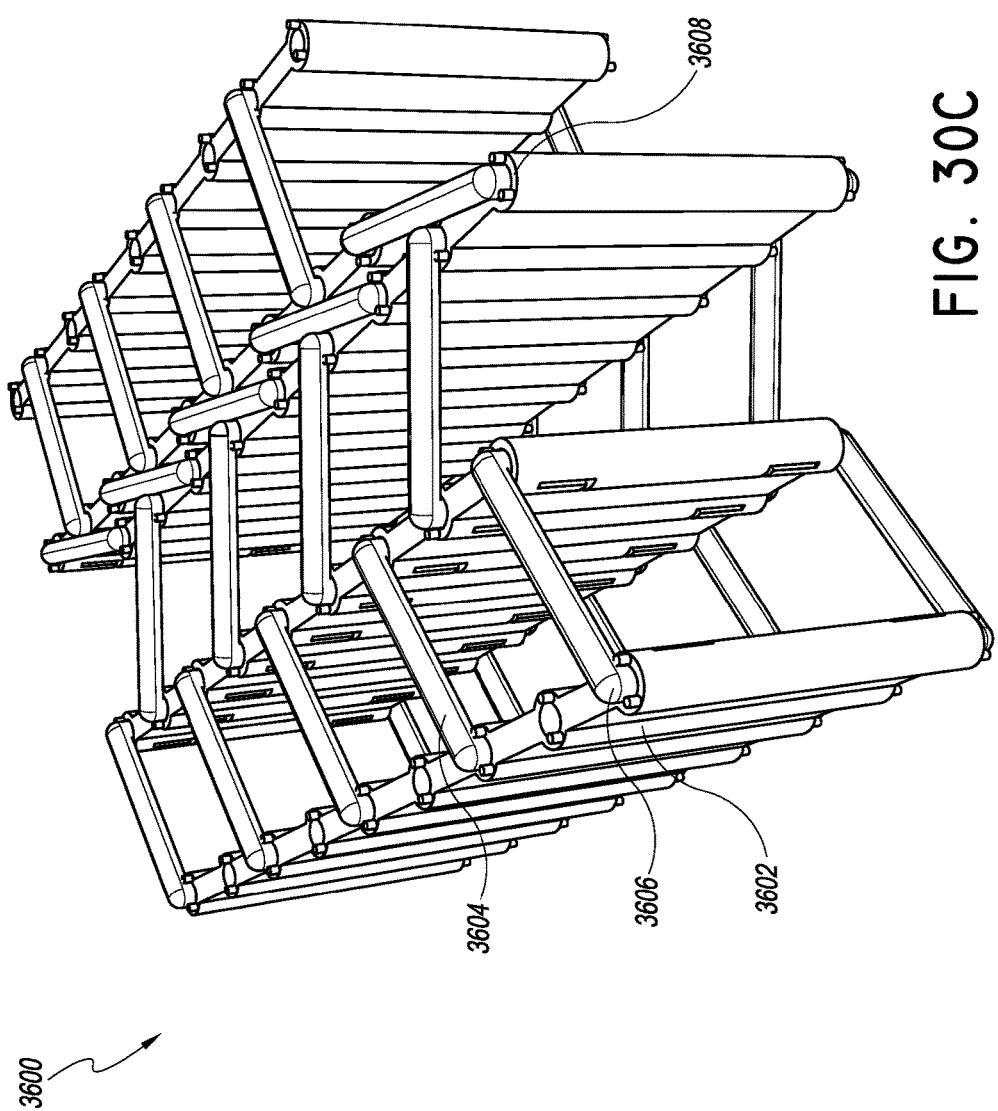
Figure 30D:
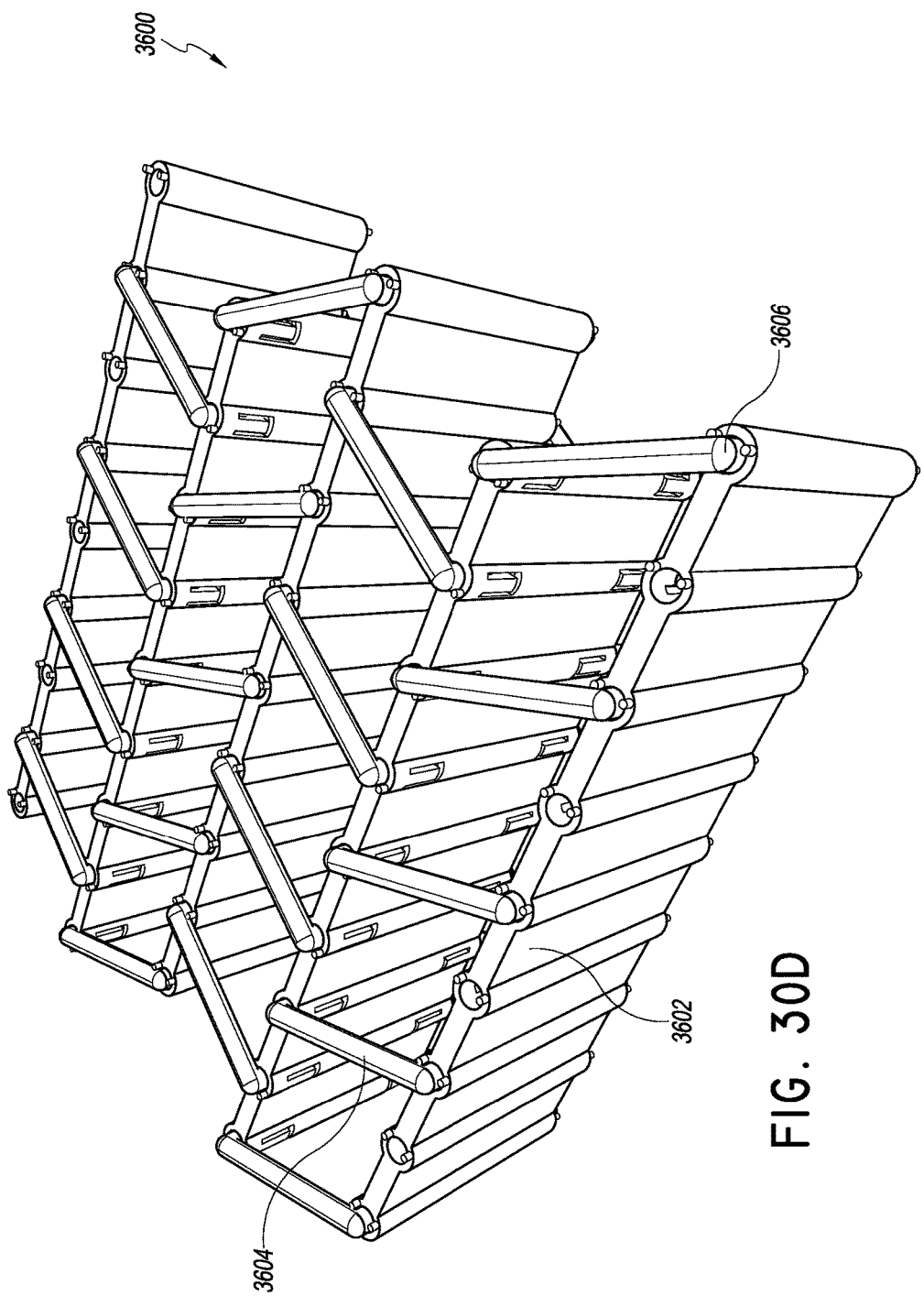

Preferably, as illustrated in the top view of FIG. 30B and the front view of FIG. 30C, in certain embodiments the pins cause the bars to protrude above the vertical top and the vertical bottom of the elongated strips 3602. In other embodiments, the bars 3604 may be connected to the elongated strips so that they are located flush with the vertical top and vertical bottom of the elongated strips 3602. In further other embodiments, the bars 3604 may be connected so that they are located below the vertical top of the elongated strips 3602 and above the vertical bottom of the elongated strip.

As illustrated in FIGS. 30A and 30C, the joints 3606 can preferably comprise a plurality of stops 3608 configured to limit the rotation of the bars relative to the strips. The stops may protrude vertically from the strips to limit the movement of the bars. For example, these stops may be used to prevent the bars from becoming fully perpendicular with respect to the adjacent strips, and may be used to provide a preferential direction of collapse to adjacent rows. As shown in FIG. 30A, a first row may have bars angled in a first direction, and a second row may have bars angled in a second direction. In some embodiments, there are two stops per bar on a given strip, to restrict motion in two directions. In other embodiments, there is one stop or three or more stops per bar on a given strip.

Figure 30E:
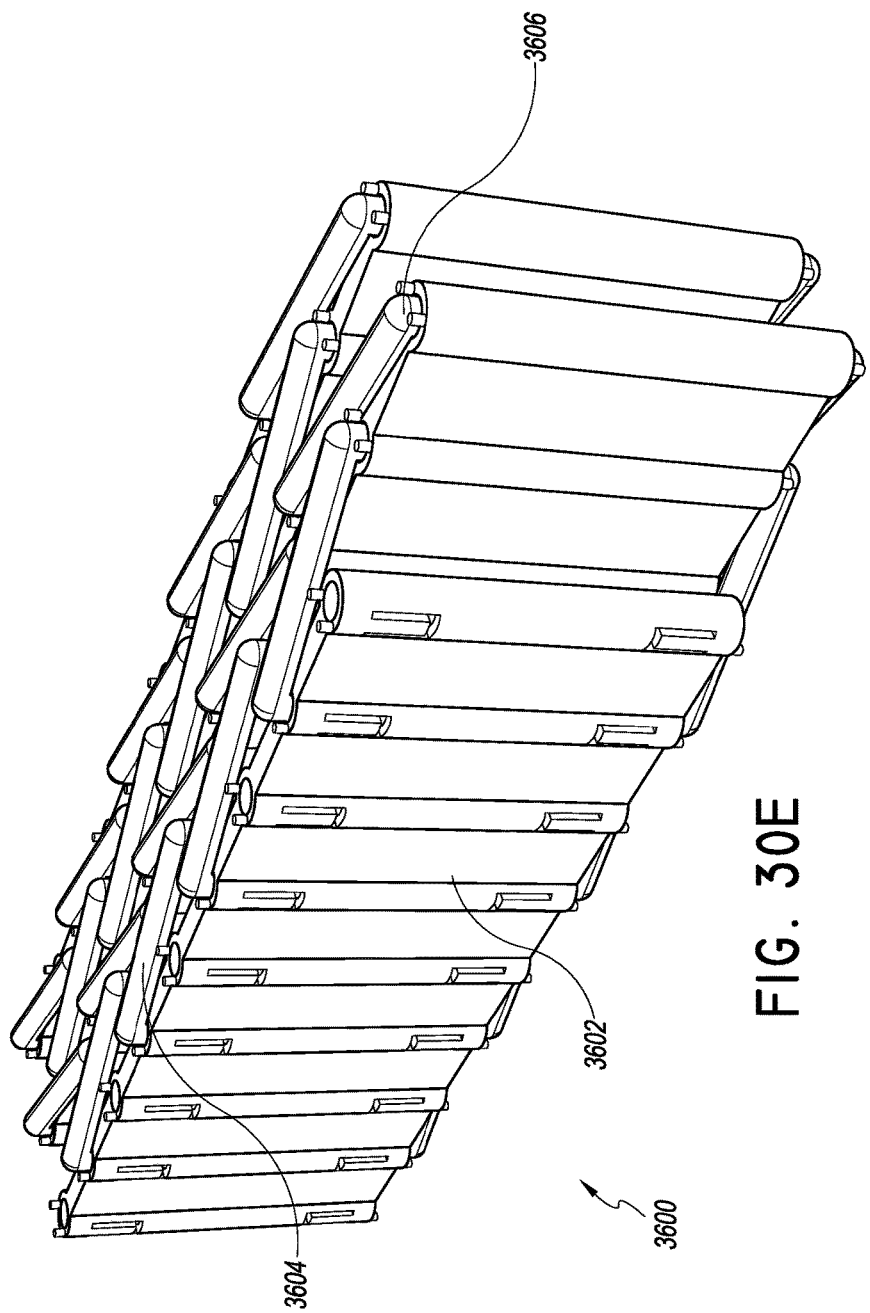
Figure 30F:
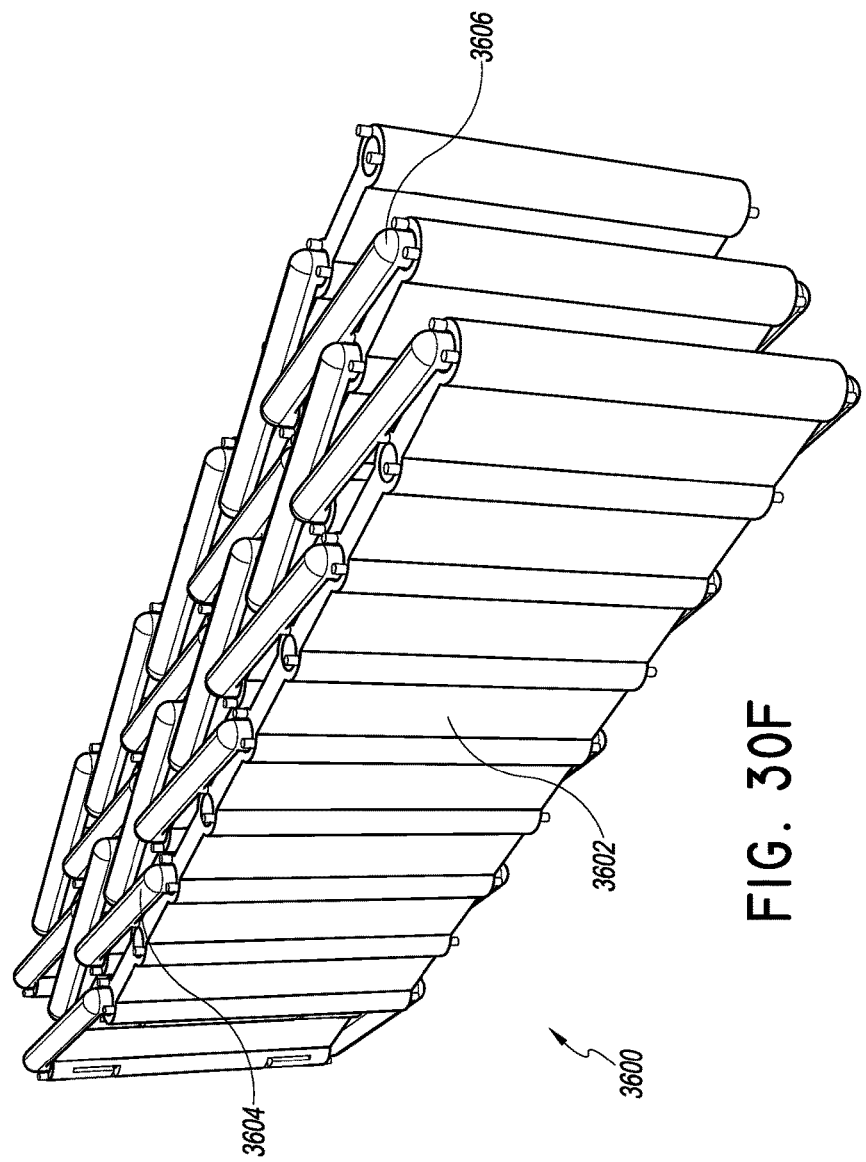
Figure 30G:
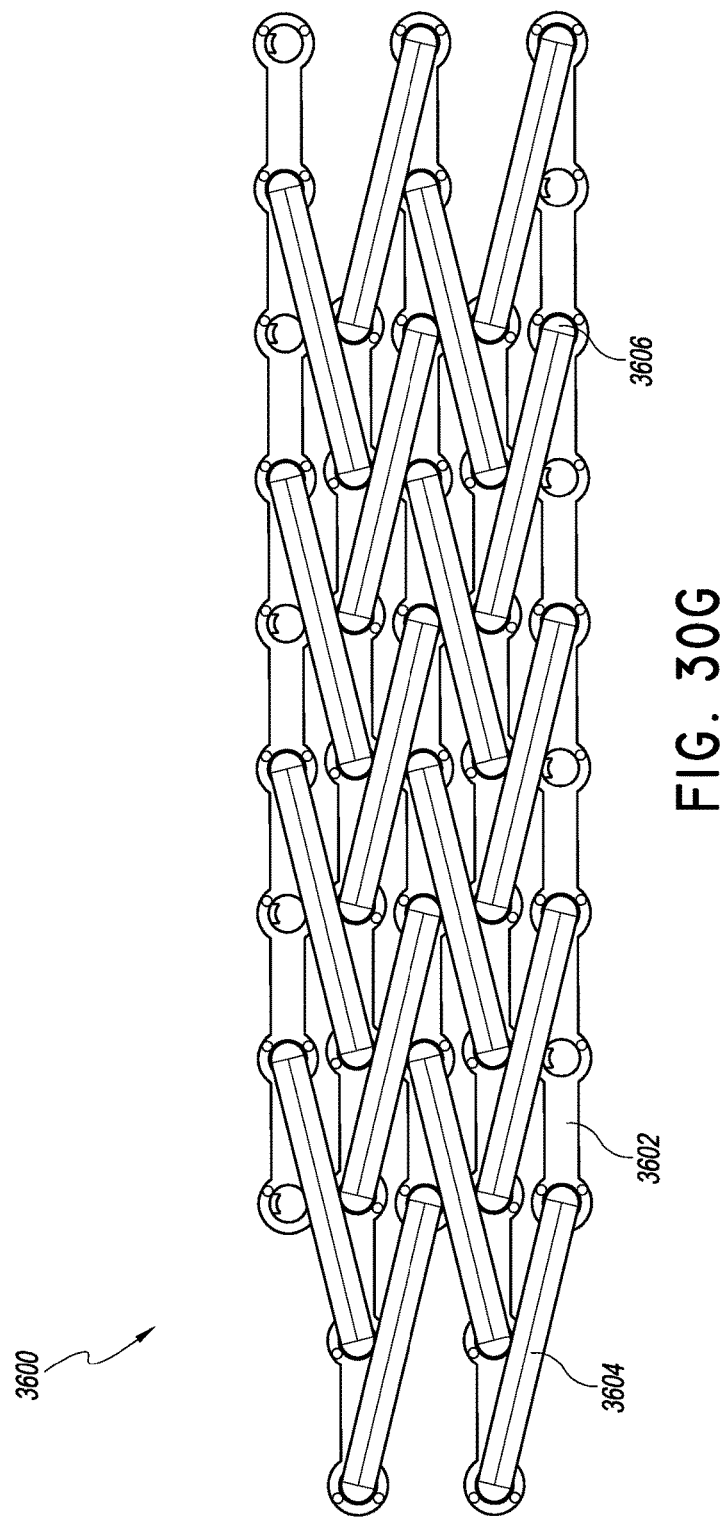

FIGS. 30E-G illustrate the stabilizing structure 3600 in a collapsed configuration. Similar to the structures of FIGS. 29A-C and FIG. 28B, the structure 3600 may be positioned in a wound in an orientation configured to collapse in a direction perpendicular to the longitudinal axis of the wound. As described above, the stabilizing structure may be surrounded by or filled with absorbent material such as foam. In one embodiment, because the vertical space between the upper and lower bars of the structure 3600 are open (as best shown in FIG. 30C), elongate blocks of foam or other compressible material may be placed in between adjacent strips to provide a desired compressibility as the structure collapses.

Figure 31:
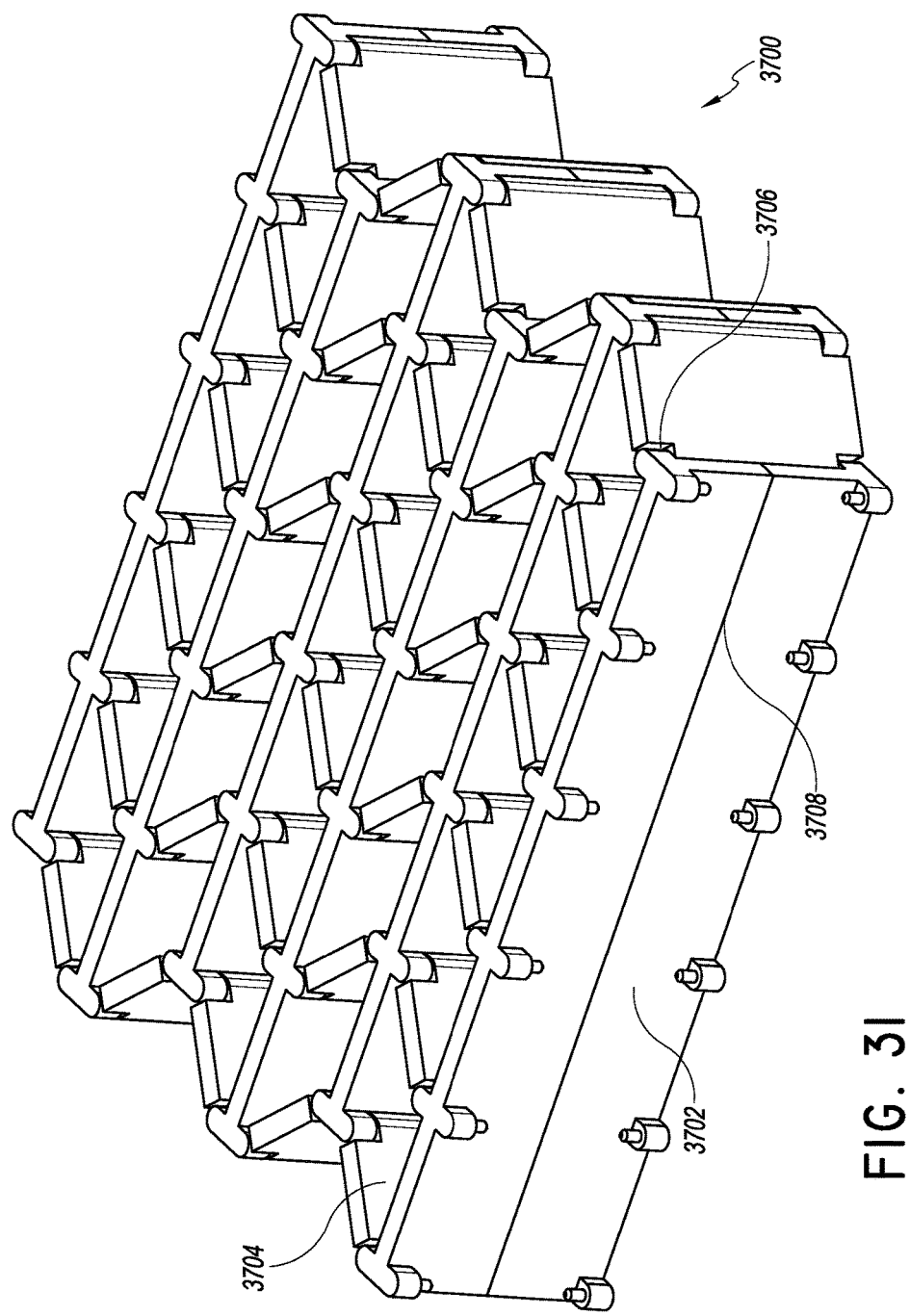
FIG. 31 illustrates one embodiment of a hinged stabilizing structure for closing a wound.

FIG. 31 illustrates an embodiment of a stabilizing structure 3700 that is similar to the structures described above in relation to FIG. 28B, FIGS. 29A-C and FIGS. 30A-G. In certain embodiments, the stabilizing structure 3700 can collapse in any manner described above. The elongated strip 3702 as illustrated is formed in two halves, and can be separated along line 3708. The intervening members 3704 can be in the form of panels as described above. The joints 3706 on the upper half of an elongated strip may comprise pins located on opposite sides of the strip extending downward from the top of the upper half of the strip. The joints 3706 on the lower half of an elongated strip may comprise pins located on opposite sides of the strip extending upward from the bottom of the lower half of the strip. These pins may engage vertical openings located at the four corners of the intervening member 3704. As the upper and lower halves are brought together, the pins may engage the openings in the panels. The upper and lower halves may be secured by any number of mechanisms, such as with adhesive and mechanical connections.

In the FIG. 31 embodiment, with the ability to separate the two halves of 3702 along line 3708, intervening members 3704 may be easily removed or replaced. In some embodiments, only some of the intervening members 3704 are removed. In certain embodiments, alternating intervening members 3704 are removed. In certain preferred embodiments, intervening members are removed in a preferential manner so as to allow the stabilizing structure 3700 to collapse in a controlled manner most appropriate for a particular wound. In some embodiments, the intervening members are replaced or removed to maximize the collapsed length of the structure 3700. In certain embodiments, intervening members are replaced or removed to minimize the collapsed length of structure 3700. In some embodiments, intervening members are replaced or removed to attain a desired length for the collapsed structure.

Figure 33:
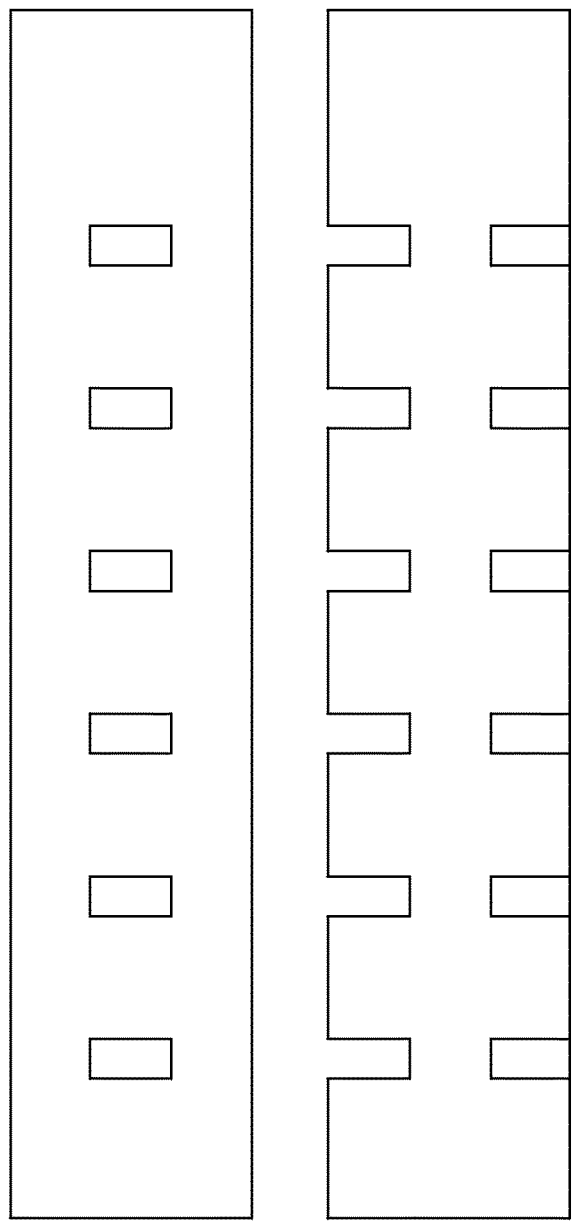
FIG. 33 illustrates one embodiment of a stabilizing structure for a wound.

FIG. 33 illustrates another embodiment of elongate strips that may be used to form a stabilizing structure, similar to that described in FIGS. 8A-D. The first strip illustrated in the upper portion of FIG. 33 may be an elongate strip having a plurality of spaced apart openings extending along a central axis of the strip. The second strip illustrated in the lower portion of FIG. 33 may have a plurality of spaced apart notches extending from the upper and lower edges of the second strip and separate by a middle portion. A plurality of the first strips and a plurality of the second strips can be assembled into a stabilizing structure similar to what's shown in FIGS. 8A, 8C and 8D, wherein the plurality of first strips are arranged in parallel to each other, and the plurality of second strips are arranged in parallel to each other. The plurality of first and second strips engage one another by the middle portions of the second strips positioned through the openings in the first strips, to place the plurality of first strips at an angle to the plurality of second strips. This structure is configured to collapse in a horizontal plane while remaining rigid in the vertical plane.

Figure 34:
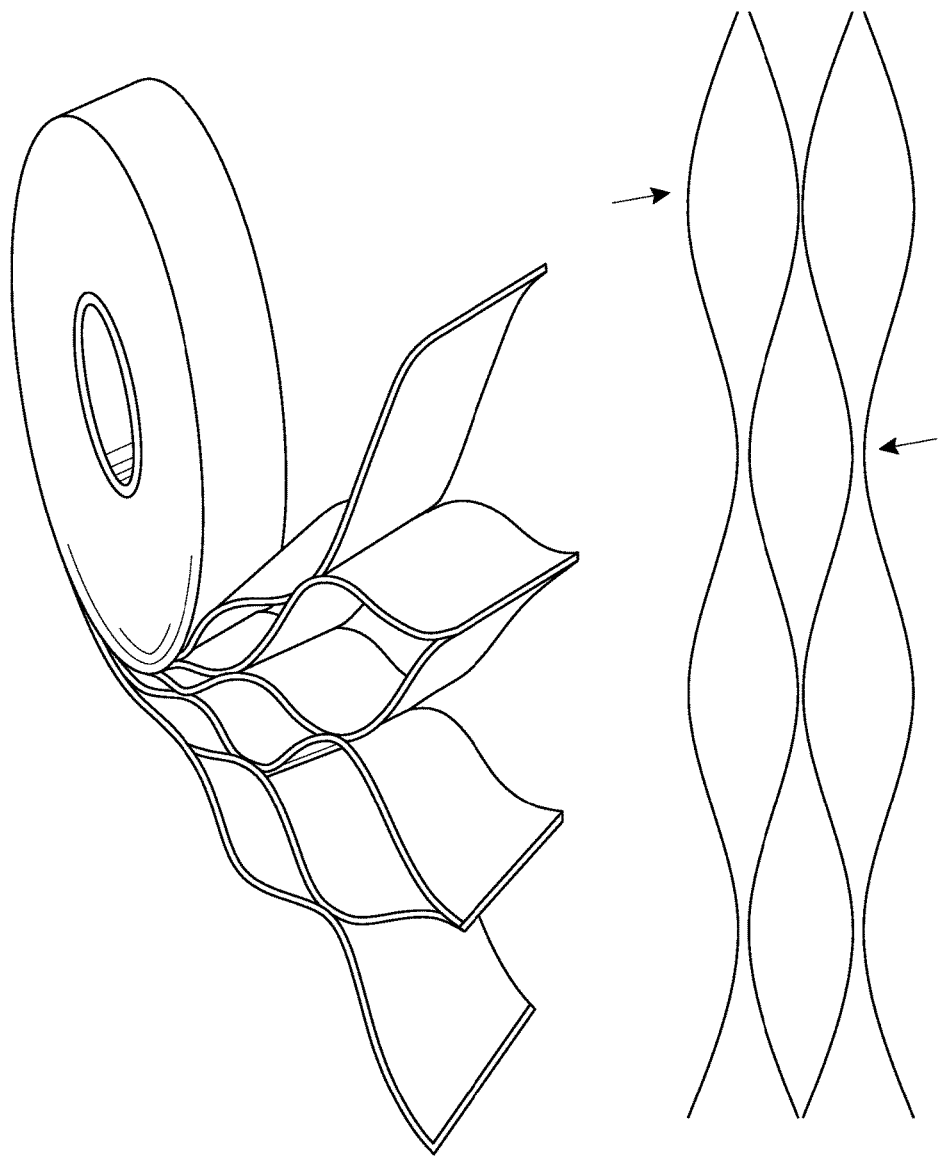
FIG. 34 illustrates an embodiment of a stabilizing structure for a wound cut from a roll.

FIG. 34 illustrates an embodiment of a stabilizing structure similar to the embodiment of FIG. 13 described above. A plurality of longitudinal strips can be provided each in the form of a wavy strip that, when joined face-to-face, form one or more circular or ovoid cells. The entire structure can be collapsed into a substantially flat configuration, and can be contained within a roll. To use the stabilizing structure, a portion of the structure can be unrolled and cut at a desired length. Preferably, as the stabilizing structure is unrolled it expands to its natural, deployed configuration. It will be appreciated that other embodiments of the stabilizing structure, and not just embodiments using the wavy strips of FIG. 13, may be assembled into a rolled configuration.

Figure 35:
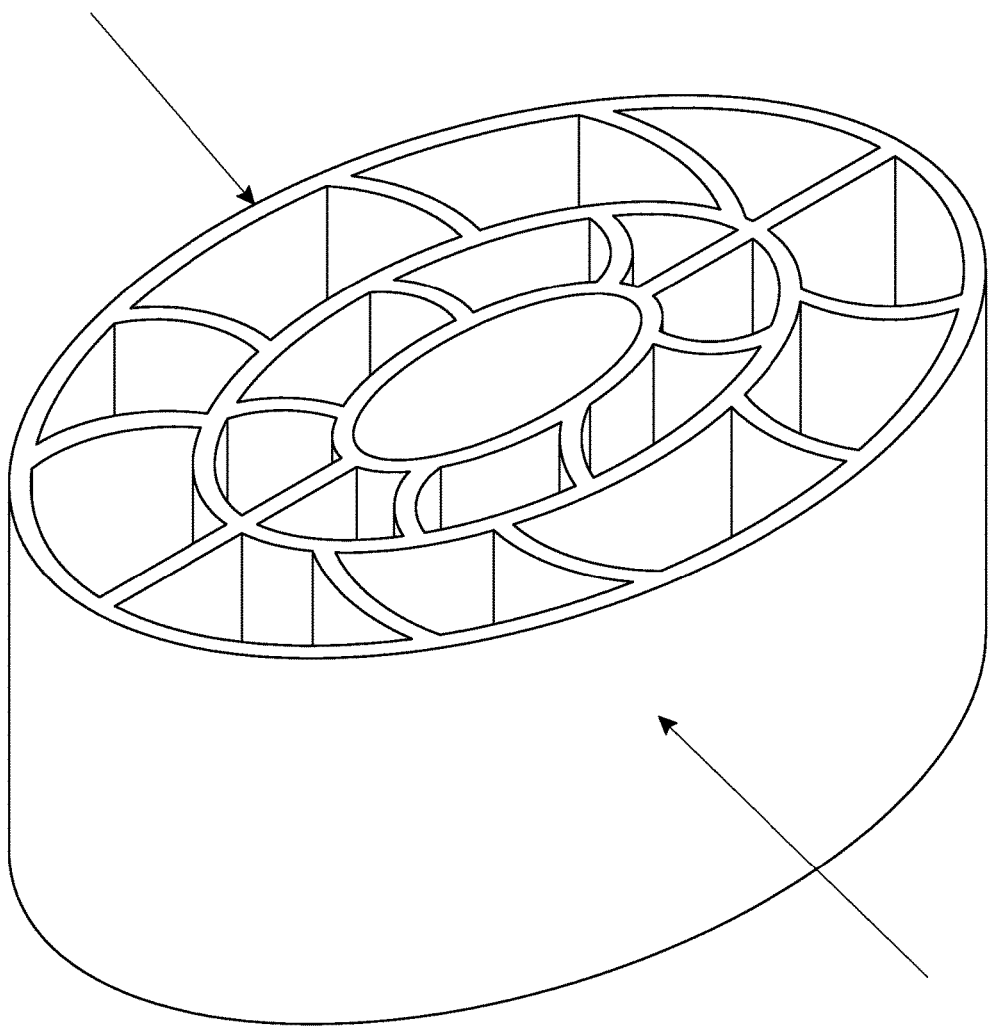
FIG. 35 illustrates an embodiment of a stabilizing structure having an oval shape.

FIG. 35 illustrates another embodiment of a stabilizing structure. In this embodiment, the stabilizing structure has an elongated, preferably oval shape, wherein cells within the oval shape have a plurality of cells arranged in a plurality of concentric rings. In the embodiment illustrated, a central oval cell is surrounded by two oval-shaped rings. Other embodiments, can include more than two oval-shaped rings.

While the invention has been described in connection with specific methods and apparatuses, those skilled in the art will recognize other equivalents to the specific embodiments herein. It is to be understood that the description is by way of example and not as a limitation to the scope of the invention and these equivalents are intended to be encompassed by the claims set forth below.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A wound closure device, comprising:
   a stabilizing structure comprising a plurality of planar support structures, each planar support structure comprising a first plurality of beams intersecting with a second plurality of beams, the plurality of planar support structures being arranged parallel to one another;
   a plurality of spring elements joining adjacent planar support structures, the plurality of spring elements providing for compression of the stabilizing structure so that the planar support structures come closer to one another; and
   wherein the planar support structure comprises one or more standoffs located on an outer plane or perimeter.

2. The device of claim 1, wherein the beams are rigid.

3. The device of claim 1, wherein the first plurality of beams intersects with the second plurality of beams at a right angle.

4. The device of claim 1, wherein the planar support structure is substantially rigid within the plane of the support structure.

5. The device of claim 1, wherein the plurality of spring elements comprise a first and a second plurality of spring elements, the first plurality of spring elements located in a first plurality of parallel planes, the first plurality of parallel planes including a first plurality of rigid beams, and wherein the second plurality of spring elements are located in a second plurality of parallel planes, the second plurality of parallel planes including the second plurality of rigid beams.

6. The device of claim 1, wherein the spring elements are V-shaped members.

7. The device of claim 1, wherein each planar support structure is identical.

8. The device of claim 1, wherein a porous material surrounds one or more of the planar support structures.

9. The device of claim 8, wherein the porous material surrounds the entire device.

10. The device of claim 1, wherein the stabilizing structure comprises 2, 3, 4, 5 or more parallel planar support structures, with spring elements provided between each.

11. The device of claim 10, further comprising an identical arrangement of spring elements between each of the planar support structures.

12. A method of closing a wound, comprising;
placing the wound closure device of claim 1 into a wound;
fluidically connecting the wound to a source of negative pressure; and
applying negative pressure to the wound via the source of negative pressure.

13. The method of claim 12, further comprising collapsing the stabilizing structure or wound closure device in a direction within the plane without significantly collapsing the device in the direction perpendicular to the plane.

14. A negative pressure wound closure system, comprising:
the wound closure device of claim 1;
a drape sized and configured to be placed over the stabilizing structure and to form a substantially fluid-tight seal against a region of skin surrounding the wound; and
a source of negative pressure in fluid communication with the wound.

15. A wound closure device, comprising:
a stabilizing structure comprising a plurality of planar support structures, each planar support structure comprising a first plurality of beams intersecting with a second plurality of beams, the plurality of planar support structures being arranged parallel to one another;
a plurality of spring elements joining adjacent planar support structures, the plurality of spring elements providing for compression of the stabilizing structure so that the planar support structures come closer to one another; and
wherein the planar support structure comprises one or more outer standoffs provided with one or more tissue anchors configured to engage tissue placed into contact with the device.

16. A wound closure device, comprising:
a stabilizing structure comprising a plurality of planar support structures, each planar support structure comprising a first plurality of beams intersecting with a second plurality of beams, the plurality of planar support structures being arranged parallel to one another;
a plurality of spring elements joining adjacent planar support structures, the plurality of spring elements providing for compression of the stabilizing structure so that the planar support structures come closer to one another; and
wherein the plurality of spring elements comprise a first plurality of spring elements located in a first plane perpendicular to the planar support structures, and a second plurality of spring elements located in a second plane perpendicular to both the first plane and to the planar support structures.

17. The device of claim 16, wherein the first plurality of spring elements is located in a first plurality of parallel planes, the first plurality of parallel planes including the first plurality of rigid beams, and wherein the second plurality of spring elements are located in a second plurality of parallel planes, the second plurality of parallel planes including the second plurality of rigid beams.

* * * * *